US012036247B2

(12) United States Patent
Reid et al.

(10) Patent No.: US 12,036,247 B2
(45) Date of Patent: Jul. 16, 2024

(54) # MULTIPLE TRANSGENE RECOMBINANT ADENOVIRUS

(71) Applicant: EpicentRx, Inc., La Jolla, CA (US)

(72) Inventors: Tony R. Reid, San Diego, CA (US); Christopher Larson, San Diego, CA (US); Bryan T. Oronsky, Los Altos Hills, CA (US)

(73) Assignee: EPICENTRX, INC., La Jolla, CA (US)

( * ) Notice: Subject to any disclaimer, the term of this patent is extended or adjusted under 35 U.S.C. 154(b) by 309 days.

(21) Appl. No.: 16/604,675

(22) PCT Filed: Apr. 12, 2018

(86) PCT No.: PCT/US2018/027375

§ 371 (c)(1),
(2) Date: Oct. 11, 2019

(87) PCT Pub. No.: WO2018/191545

PCT Pub. Date: Oct. 18, 2018

(65) Prior Publication Data

US 2020/0078415 A1 Mar. 12, 2020

Related U.S. Application Data

(60) Provisional application No. 62/484,841, filed on Apr. 12, 2017.

(51) Int. Cl.

| | |
|---|---|
| ***A61P 35/00*** | (2006.01) |
| ***A61K 35/74*** | (2015.01) |
| ***A61K 35/768*** | (2015.01) |
| ***A61K 48/00*** | (2006.01) |
| ***C07K 14/54*** | (2006.01) |
| ***C12N 9/64*** | (2006.01) |
| ***C12N 15/86*** | (2006.01) |
| ***C12N 15/861*** | (2006.01) |

(52) U.S. Cl.

CPC ............ *A61K 35/74* (2013.01); *A61K 35/768* (2013.01); *A61K 48/00* (2013.01); *A61P 35/00* (2018.01); *C12N 9/6454* (2013.01); *C12N 15/86* (2013.01); *C12N 15/861* (2013.01); *C07K 2319/50* (2013.01); *C12N 2710/10343* (2013.01); *C12Y 304/21075* (2013.01)

(58) Field of Classification Search

CPC .... C12N 15/86; C12N 15/861; C12N 9/6454; C12N 2710/10332; C12N 2710/10343; A61P 35/00; A61K 35/768; A61K 48/00; C07K 14/54; C07K 14/5434

See application file for complete search history.

(56) References Cited

U.S. PATENT DOCUMENTS

| | | | |
|---|---|---|---|
| 5,670,488 A | 9/1997 | Gregory et al. | |
| 7,498,024 B2 | 3/2009 | Fang et al. | |
| 9,073,980 B2 * | 7/2015 | Reid | C12N 15/86 |
| 2004/0091996 A1 | 5/2004 | Qian et al. | |
| 2004/0234505 A1 | 11/2004 | Naylor et al. | |
| 2005/0042721 A1 | 2/2005 | Fang et al. | |
| 2005/0136035 A1 | 6/2005 | Ko et al. | |
| 2005/0214923 A1 | 9/2005 | Yu et al. | |
| 2009/0270485 A1 | 10/2009 | Ko et al. | |
| 2011/0286999 A1 | 11/2011 | Holm | |
| 2017/0202892 A1 | 7/2017 | Kumon et al. | |
| 2018/0185515 A1 | 7/2018 | Hicklin et al. | |
| 2019/0352616 A1 | 11/2019 | Reid et al. | |
| 2020/0155625 A1 | 5/2020 | Larson et al. | |

FOREIGN PATENT DOCUMENTS

| | | |
|---|---|---|
| CN | 103038343 A | 4/2013 |
| CN | 104271748 A | 1/2015 |
| CN | 105307671 A | 2/2016 |
| CN | 103614416 B | 9/2016 |
| EP | 3029144 A1 | 6/2016 |
| JP | 2006526409 A | 11/2006 |
| JP | 2012519014 A | 8/2012 |
| JP | 2014500004 A | 1/2014 |
| KR | 20090007067 A | 1/2009 |
| KR | 100896483 B1 | 5/2009 |
| KR | 101253276 B1 | 4/2013 |
| WO | WO-1997006826 A1 | 2/1997 |
| WO | WO-1998027216 A1 | 6/1998 |
| WO | WO-2002088173 A2 | 11/2002 |
| WO | WO-2004108893 A2 | 12/2004 |
| WO | WO-2005017149 A1 | 2/2005 |
| WO | WO-2008140173 A1 | 11/2008 |
| WO | WO-2010101921 A2 | 9/2010 |
| WO | WO-2012038606 A1 | 3/2012 |
| WO | WO-2014170389 A1 | 10/2014 |
| WO | WO-2016049201 A1 | 3/2016 |
| WO | WO-2018083259 A1 | 5/2018 |
| WO | WO-2018126282 A1 | 7/2018 |
| WO | WO-2018140973 A1 | 8/2018 |

OTHER PUBLICATIONS

Wang et al., Human Gene Therapy 23: 992-1002, 2012.*
Wu et al, Cell 25(3): 627-635, 1981; abstract only.*
Wu et al, Molecular Therapy 9(5): 674-681, 2004.*
Choi et al, PLoS One 8(7): e67512, 15 pages 2013.*
Wozniak et al, Infection and Immunity 74(1): 557-565, 2006.*
Gaken et al, Gene Therapy 7: 1979-1985, 2000.*
Chen et al, Reconstructive Surgery 23(8): 947-953, 2009; abstract only.*
GenBank NM_003810 (2022).*
GenBank AF262240 (2000).*
GenBank BC067511 (2006).*
GenBank AF180563 (1999).*

(Continued)

*Primary Examiner* — Kevin K Hill
(74) *Attorney, Agent, or Firm* — Morrison & Foerster LLP

(57) ABSTRACT

The invention relates to a recombinant adenovirus comprising two or more therapeutic transgenes, e.g., two components of a heterodimeric cytokine, separated by a cleavable linker.

13 Claims, 10 Drawing Sheets

Specification includes a Sequence Listing.

(56) References Cited

OTHER PUBLICATIONS

Shan et al, Cellular & Molecular Immunology 3(1): 47-52, 2006.*
Overwijk et al, J. Immunol. 176: 5213-5222, 2006.*
Yuan et al., An oncolytic adenovirus that expresses the HAb18 and interleukin 24 genes exhibits enhanced antitumor activity in hepatocellular carcinoma cells, Oncotarget 7(37): 60491-60502, available Aug. 9, 2016.*
GenBank Accession BC009681, *Homo sapiens* IL-24, mRNA; 2006.*
Takayanagi et al, Constitutive Stimulation of Vascular Smooth Muscle Cells by Angiotensin II Derived From an Adenovirus Encoding a Furin-Cleavable Fusion Protein, Am. J. Hypertension 25(3): 280-283, 2012.*
Minskaia et al, Protein Coexpression Using FMDV 2A: Effect of "Linker" Residues, BioMed Res. International, Article ID 291730, 12 pages, doi.org/10.1155/2013/291730, 2013.*
Chan et al, Comparison of IRES and F2A-Based Locus-Specific Multicistronic Expression in Stable Mouse Lines, PLoS One 6(12): e28885, 11 pages, doi.org/10.1371/journal.pone.0028885, 2011.*
Invitrogen, pAd/CMV/V5-DEST™ and pAd/PL-DEST™ Gateway® Vectors, Catalog Nos. V493-20 andV494-20, User Manual, Publication Part No. 25-0544, 2012.*
Finger et al, Replicating retroviral vectors mediating continuous production and secretion of therapeutic gene products from cancer cells, Cancer Gene Therapy 12: 464-474, 2005.*
Genbank NP_002178.2, interleukin-12 subunit beta precursor [*Homo sapiens*], Mar. 15, 2015.*
Genbank NP_057668.1, interleukin-23 subunit alpha precursor [*Homo sapiens*], Mar. 15, 2015.*
Genbank NP_000873, interleukin-12 subunit alpha precursor [*Homo sapiens*], Mar. 15, 2015.*
Jiang et al, Furin-Mediated Sequential Delivery of Anticancer Cytokine and Small-Molecule Drug Shuttled by Graphene, Advanced Materials 27(6): 1021-1028, Feb. 11, 2015.*
Altschul et al., (1994). "Issues in searching molecular sequence databases," Nature Genetics, 6:119-129.
Altschul et al., (1997). "Gapped BLAST and PSI-BLAST: a new generation of protein database search programs," Nucleic Acids Res., 25:3389-402.
Altschul, (1993). "A protein alignment scoring system sensitive at all evolutionary distances," J. Mol. Evol., 36:290-300.
Bukczynski et al., (2005). "Enhancement of HIV-Specific CD8 T Cell Responses by Dual Costimulation with CD80 and CD137L," J. Immunol., 175:6378-6389.
Chaplin et al., (1999). "Production of interleukin-12 as a self-processing 2A polypeptide," Journal of Interferon and Cytokine Research, 19(3):235-241.
Choi et al., (2013). "Oncolytic Adenovirus Expressing IL-23 and p35 Elicits IFN-y- and TNF-a-Co-Producing T Cell-Mediated Antitumor Immunity", PLOS One, 87(7):e67512, 15 pages.
Cody et al., (2009). "Armed replicating adenoviruses for cancer virotherapy," Cancer Gene Ther, 16(6):473-488, 29 pages.
Extended European Search Report and Written Opinion for European Application 18743942.7 dated Dec. 3, 2020, 14 pages.
Extended European Search Report and Written Opinion for European Application 18784495.6 dated Jan. 20, 2021, 10 pages.
Feng et al. (1997). "Stable in vivo gene transduction via a novel adenoviral/retroviral chimeric vector," Nature Biotechnology, 15: 866-870.
Furler et al., (2001). "Recombinant AAV vectors containing the foot and mouth disease virus 2A sequence confer efficient biscistronic gene expression in cultured cells and rat substantia nigra neurons," Gene Therapy, 8:864-873.
Gaken et al., (2000). "Fusagene vectors: A novel strategy for the expression of multiple genes from a single cistron," Gene Therapy, 7(23):1979-1985.
Guinn et al., (1999). "4-1BBL Cooperates with B7-1 and B7-2 in Converting a B Cell Lymphoma Cell Line into a Long-Lasting Antitumor Vaccine," J. Immunol., 162:5003-5010.
Guo et al., (2014). "Assays to examine endothelial cell migration, tube formation, and gene expression profiles," Methods Mol. Biol., 1135:393-402, 9 pages.
Hedjran et al., (2011). "Deletion analysis of Ad5 Ela transcriptional control region: impact on tumor-selective expression of Ela and Elb", Cancer Gene Therapy, 18:717-723.
Henikoff et al., (1992). "Amino Acid Substitution Matrices from Protein Blocks," Proc. Natl. Acad. Sci. USA, 89:10915-10919.
International Search Report and Written Opinion for PCT Patent Application No. PCT/US2018/027375 dated Jul. 18, 2018, 17 pages.
International Search Report and Written Opinion received for International Patent Application No. PCT/US2018/034487 dated Aug. 30, 2018, 17 pages.
International Search Report for PCT/US2018/016032, dated Apr. 11, 2018 (9 pages).
Jing et al., (2005). "Identification of novel insertion sites in the Ad5 genome that utilize the Ad splicing machinery for therapeutic gene expression," Molecular Therapy, 12(6):1052-1063.
Jounaidi et al., (2007). "Conditionally Replicating Adenoviruses for Cancer Treatment," Curr Cancer Drug Targets, 7(3):285-301, 35 pages.
Karlin et al., (1990). "Methods for assessing the statistical significance of molecular sequence features by using general scoring schemes," Proc. Natl. Acad. Sci. USA, 87:2264-2268.
Kirn, (2000). "Replication-selective oncolytic adenoviruses: virotherapy aimed at genetic targets in cancer," Oncogene, 19(56):6660-6669.
Kirn, (2001). "Oncolytic virotherapy for cancer with the adenovirus dl1520 (Onyx-015): results of phase I and II trials," Expert Opinion on Biological Therapy, 1(3):525-538.
Kumar et al., (2008). "Virus combinations and chemotherapy for the treatment of human cancers," Current Opinion in Molecular Therapeutics, 10(4):371-379. (Abstract only).
Melero et al., (1998). "Amplification of tumor immunity by gene transfer of the co-stimulatory 4-1BB ligand: synergy with the CD28 co-stimulatory pathway," Eur. J. Immunol., 28:1116-1121.
Ponnazhagan et al., (2004). "Adeno-associated virus 2-mediated antiangiogenic cancer gene therapy: long-term efficacy of a vector encoding angiostatin and endostatin over vectors encoding a single factor," Canc. Res., 64:1781-1787.
Renaud-Gabardos et al., (2015). "Internal ribosome entry site-based vectors for combined gene therapy," World J Exp Med, 25(1):11-20.
Salucci et al., (2005). "Adenovirus Transduction and Culture Conditions Affect the Immunogenicity of Murine Dendritic Cells," Scand. J. Immunol., 62:206-217.
Small et al., (2014). "Construction and Characterization of E1- and E3-Deleted Adenovirus Vectors Expressing Two Antigens from Two Separate Expression Cassettes," Human Gene Therapy, 25:328-338.
Sunshine et al., (2012). "Endostatin lowers blood pressure via nitric oxide and prevents hypertension associated with VEGF inhibition," PNAS, 109(28):11306-11311.
Velasquez et al., (2014). "T Cells Expressing Engager and Costimulatory Molecules for the Immunotherapy of CD19+ Malignancies," Blood, 124:2433.
Weiping et al., (1997). "Construction of the Dicistronic Adenovirus Vector Expressing Bioactive Human Interleukin-12" Chinese Journal of Cancer Research, 9(4):299-303.
Wen et al., (2001). "Tricistronic viral vectors co-expressing interleukin-12 (1L-12) and CD80 (B7-1) for the immunotherapy of cancer: preclinical studies in myeloma," Cancer Gene Ther., 8(5), 361-370.
Written Opinion for PCT/US2018/016032, dated Apr. 11, 2018 (8 pages).
Extended European Search Report and Written Opinion for European Application 18806701.1 dated Feb. 11, 2021, 8 pages.
Hanaka et al., (1987). "Regulation of in Vitro and in Vivo Transcription of Early-Region IV of Adenovirus Type 5 by Multiple cis-Acting Elements," Molecular and Cellular Biology, 7(7):2578-87.
Rodriguez-Garcia et al., (2015). "Insertion of exogenous epitopes in the E3-19K of oncolytic adenoviruses to enhance TAP-independent presentation and immunogenicity," Gene Therapy, 22:596-601.
Wong et al., (2010). "Oncolytic Viruses for Cancer Therapy: Overcoming the Obstacles," Viruses, 2(1):78-106.

(56) References Cited

OTHER PUBLICATIONS

Zhang et al., (1997). "Construction of the dicistronic adenovirus vector expressing bioactive human interleukin-12," Chinese Journal of Cancer Research, 9(4):299-303.

* cited by examiner

SEQUENCE LISTING

<160> NUMBER OF SEQ ID NOS: 26

<210> SEQ ID NO 1
<211> LENGTH: 35938
<212> TYPE: DNA
<213> ORGANISM: Adenovirus type 5

<400> SEQUENCE: 1
catcatcaat aatatacctt attttggatt gaagccaata tgataatgag ggggtggagt 60

-continued

```
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggactgaaaa tgagacatat tatctgccac ggaggtgtta ttaccgaaga    600
aatggccgcc agtcttttgg accagctgat cgaagaggta ctggctgata atcttccacc    660
tcctagccat tttgaaccac ctacccttca cgaactgtat gatttagacg tgacggcccc    720
cgaagatccc aacgaggagg cggtttcgca gatttttccc gactctgtaa tgttggcggt    780
gcaggaaggg attgacttac tcacttttcc gccggcgccc ggttctccgg agccgcctca    840
cctttcccgg cagcccgagc agccggagca gagagccttg ggtccggttt ctatgccaaa    900
ccttgtaccg gaggtgatcg atcttacctg ccacgaggct ggctttccac ccagtgacga    960
cgaggatgaa gagggtgagg agtttgtgtt agattatgtg gagcaccccg ggcacggttg   1020
caggtcttgt cattatcacc ggaggaatac gggggaccca gatattatgt gttcgctttg   1080
ctatatgagg acctgtggca tgtttgtcta cagtaagtga aaattatggg cagtgggtga   1140
tagagtggtg ggtttggtgt ggtaattttt tttttaattt ttacagtttt gtggtttaaa   1200
gaattttgta ttgtgatttt tttaaaaggt cctgtgtctg aacctgagcc tgagcccgag   1260
ccagaaccgg agcctgcaag acctacccgc cgtcctaaaa tggcgcctgc tatcctgaga   1320
cgcccgacat cacctgtgtc tagagaatgc aatagtagta cggatagctg tgactccggt   1380
ccttctaaca cacctcctga gatacacccg gtggtcccgc tgtgccccat taaaccagtt   1440
gccgtgagag ttggtgggcg tcgccaggct gtggaatgta tcgaggactt gcttaacgag   1500
cctgggcaac ctttggactt gagctgtaaa cgccccaggc cataaggtgt aaacctgtga   1560
ttgcgtgtgt ggttaacgcc tttgtttgct gaatgagttg atgtaagttt aataaagggt   1620
gagataatgt ttaacttgca tggcgtgtta aatggggcgg ggcttaaagg gtatataatg   1680
cgccgtgggc taatcttggt tacatctgac ctcatggagg cttgggagtg tttggaagat   1740
ttttctgctg tgcgtaactt gctggaacag agctctaaca gtacctcttg gttttggagg   1800
tttctgtggg gctcatccca ggcaaagtta gtctgcagaa ttaaggagga ttacaagtgg   1860
gaatttgaag agcttttgaa atcctgtggt gagctgtttg attctttgaa tctgggtcac   1920
caggcgcttt tccaagagaa ggtcatcaag actttggatt tttccacacc ggggcgcgct   1980
gcggctgctg ttgctttttt gagttttata aaggataaat ggagcgaaga aacccatctg   2040
agcggggggt acctgctgga ttttctggcc atgcatctgt ggagagcggt tgtgagacac   2100
aagaatcgcc tgctactgtt gtcttccgtc cgcccggcga taataccgac ggaggagcag   2160
cagcagcagc aggaggaagc caggcggcgg cggcaggagc agagcccatg gaacccgaga   2220
gccggcctgg accctcggga atgaatgttg tacaggtggc tgaactgtat ccagaactga   2280
gacgcatttt gacaattaca gaggatgggc aggggctaaa gggggtaaag agggagcggg   2340
ggcttgtgga ggctacagag gaggctagga atctagcttt tagcttaatg accagacacc   2400
```

-continued

```
gtcctgagtg tattactttt caacagatca aggataattg cgctaatgag cttgatctgc   2460
tggcgcagaa gtattccata gagcagctga ccacttactg gctgcagcca ggggatgatt   2520
ttgaggaggc tattagggta tatgcaaagg tggcacttag gccagattgc aagtacaaga   2580
tcagcaaact tgtaaatatc aggaattgtt gctacatttc tgggaacggg gccgaggtgg   2640
agatagatac ggaggatagg gtggccttta gatgtagcat gataaatatg tggccggggg   2700
tgcttggcat ggacggggtg gttattatga atgtaaggtt tactggcccc aattttagcg   2760
gtacggtttt cctggccaat accaacctta tcctacacgg tgtaagcttc tatgggttta   2820
acaatacctg tgtggaagcc tggaccgatg taagggttcg gggctgtgcc ttttactgct   2880
gctggaaggg ggtggtgtgt cgccccaaaa gcagggcttc aattaagaaa tgcctctttg   2940
aaaggtgtac cttgggtatc ctgtctgagg gtaactccag ggtgcgccac aatgtggcct   3000
ccgactgtgg ttgcttcatg ctagtgaaaa gcgtggctgt gattaagcat aacatggtat   3060
gtggcaactg cgaggacagg gcctctcaga tgctgacctg ctcggacggc aactgtcacc   3120
tgctgaagac cattcacgta gccagccact ctcgcaaggc ctggccagtg tttgagcata   3180
acatactgac ccgctgttcc ttgcatttgg gtaacaggag gggggtgttc ctaccttacc   3240
aatgcaattt gagtcacact aagatattgc ttgagcccga gagcatgtcc aaggtgaacc   3300
tgaacggggt gtttgacatg accatgaaga tctggaaggt gctgaggtac gatgagaccc   3360
gcaccaggtg cagaccctgc gagtgtggcg gtaaacatat taggaaccag cctgtgatgc   3420
tggatgtgac cgaggagctg aggcccgatc acttggtgct ggcctgcacc cgcgctgagt   3480
ttggctctag cgatgaagat acagattgag gtactgaaat gtgtgggcgt ggcttaaggg   3540
tgggaaagaa tatataaggt gggggtctta tgtagttttg tatctgtttt gcagcagccg   3600
ccgccgccat gagcaccaac tcgtttgatg gaagcattgt gagctcatat ttgacaacgc   3660
gcatgccccc atgggccggg gtgcgtcaga atgtgatggg ctccagcatt gatggtcgcc   3720
ccgtcctgcc cgcaaactct actaccttga cctacgagac cgtgtctgga acgccgttgg   3780
agactgcagc ctccgccgcc gcttcagccg ctgcagccac cgcccgcggg attgtgactg   3840
actttgcttt cctgagcccg cttgcaagca gtgcagcttc ccgttcatcc gcccgcgatg   3900
acaagttgac ggctcttttg gcacaattgg attctttgac ccgggaactt aatgtcgttt   3960
ctcagcagct gttggatctg cgccagcagg tttctgccct gaaggcttcc tcccctccca   4020
atgcggttta aaacataaat aaaaaaccag actctgtttg gatttggatc aagcaagtgt   4080
cttgctgtct ttatttaggg gttttgcgcg cgcggtaggc ccgggaccag cggtctcggt   4140
cgttgagggt cctgtgtatt ttttccagga cgtggtaaag gtgactctgg atgttcagat   4200
acatgggcat aagcccgtct ctggggtgga ggtagcacca ctgcagagct tcatgctgcg   4260
gggtggtgtt gtagatgatc cagtcgtagc aggagcgctg ggcgtggtgc ctaaaaatgt   4320
ctttcagtag caagctgatt gccaggggca ggcccttggt gtaagtgttt acaaagcggt   4380
taagctggga tgggtgcata cgtggggata tgagatgcat cttggactgt atttttaggt   4440
tggctatgtt cccagccata tccctccggg gattcatgtt gtgcagaacc accagcacag   4500
tgtatccggt gcacttggga aatttgtcat gtagcttaga aggaaatgcg tggaagaact   4560
tggagacgcc cttgtgacct ccaagatttt ccatgcattc gtccataatg atggcaatgg   4620
gcccacgggc ggcggcctgg gcgaagatat ttctgggatc actaacgtca tagttgtgtt   4680
ccaggatgag atcgtcatag gccattttta caaagcgcgg gcggagggtg ccagactgcg   4740
gtataatggt tccatccggc ccaggggcgt agttaccctc acagatttgc atttcccacg   4800
```

-continued

```
ctttgagttc agatgggggg atcatgtcta cctgcggggc gatgaagaaa acggtttccg   4860
gggtagggga gatcagctgg gaagaaagca ggttcctgag cagctgcgac ttaccgcagc   4920
cggtgggccc gtaaatcaca cctattaccg ggtgcaactg gtagttaaga gagctgcagc   4980
tgccgtcatc cctgagcagg ggggccactt cgttaagcat gtccctgact cgcatgtttt   5040
ccctgaccaa atccgccaga aggcgctcgc cgcccagcga tagcagttct tgcaaggaag   5100
caaagttttt caacggtttg agaccgtccg ccgtaggcat gcttttgagc gtttgaccaa   5160
gcagttccag gcggtcccac agctcggtca cctgctctac ggcatctcga tccagcatat   5220
ctcctcgttt cgcgggttgg ggcggctttc gctgtacggc agtagtcggt gctcgtccag   5280
acgggccagg gtcatgtctt tccacgggcg cagggtcctc gtcagcgtag tctgggtcac   5340
ggtgaagggg tgcgctccgg gctgcgcgct ggccagggtg cgcttgaggc tggtcctgct   5400
ggtgctgaag cgctgccggt cttcgccctg cgcgtcggcc aggtagcatt tgaccatggt   5460
gtcatagtcc agcccctccg cggcgtggcc cttggcgcgc agcttgccct tggaggaggc   5520
gccgcacgag gggcagtgca gacttttgag ggcgtagagc ttgggcgcga gaaataccga   5580
ttccggggag taggcatccg cgccgcaggc cccgcagacg gtctcgcatt ccacgagcca   5640
ggtgagctct ggccgttcgg ggtcaaaaac caggtttccc ccatgctttt tgatgcgttt   5700
cttacctctg gtttccatga gccggtgtcc acgctcggtg acgaaaaggc tgtccgtgtc   5760
cccgtataca gacttgagag gcctgtcctc gagcggtgtt ccgcggtcct cctcgtatag   5820
aaactcggac cactctgaga caaaggctcg cgtccaggcc agcacgaagg aggctaagtg   5880
ggaggggtag cggtcgttgt ccactagggg gtccactcgc tccagggtgt gaagacacat   5940
gtcgccctct tcggcatcaa ggaaggtgat tggtttgtag gtgtaggcca cgtgaccggg   6000
tgttcctgaa ggggggctat aaaagggggt gggggcgcgt tcgtcctcac tctcttccgc   6060
atcgctgtct gcgagggcca gctgttgggg tgagtactcc ctctgaaaag cgggcatgac   6120
ttctgcgcta agattgtcag tttccaaaaa cgaggaggat ttgatattca cctggcccgc   6180
ggtgatgcct ttgagggtgg ccgcatccat ctggtcagaa aagacaatct ttttgttgtc   6240
aagcttggtg gcaaacgacc cgtagagggc gttggacagc aacttggcga tggagcgcag   6300
ggtttggttt ttgtcgcgat cggcgcgctc cttggccgcg atgtttagct gcacgtattc   6360
gcgcgcaacg caccgccatt cgggaaagac ggtggtgcgc tcgtcgggca ccaggtgcac   6420
gcgccaaccg cggttgtgca gggtgacaag gtcaacgctg gtggctacct ctccgcgtag   6480
gcgctcgttg gtccagcaga ggcggccgcc cttgcgcgag cagaatggcg gtagggggtc   6540
tagctgcgtc tcgtccgggg ggtctgcgtc cacggtaaag accccgggca gcaggcgcgc   6600
gtcgaagtag tctatcttgc atccttgcaa gtctagcgcc tgctgccatg cgcgggcggc   6660
aagcgcgcgc tcgtatgggt tgagtggggg accccatggc atggggtggg tgagcgcgga   6720
ggcgtacatg ccgcaaatgt cgtaaacgta gaggggctct ctgagtattc caagatatgt   6780
agggtagcat cttccaccgc ggatgctggc gcgcacgtaa tcgtatagtt cgtgcgaggg   6840
agcgaggagg tcgggaccga ggttgctacg ggcgggctgc tctgctcgga agactatctg   6900
cctgaagatg gcatgtgagt tggatgatat ggttggacgc tggaagacgt tgaagctggc   6960
gtctgtgaga cctaccgcgt cacgcacgaa ggaggcgtag gagtcgcgca gcttgttgac   7020
cagctcggcg gtgacctgca cgtctagggc gcagtagtcc agggtttcct tgatgatgtc   7080
atacttatcc tgtccctttt ttttccacag ctcgcggttg aggacaaact cttcgcggtc   7140
```

-continued

```
tttccagtac tcttggatcg gaaacccgtc ggcctccgaa cggtaagagc ctagcatgta   7200
gaactggttg acggcctggt aggcgcagca tcccttttct acgggtagcg cgtatgcctg   7260
cgcggccttc cggagcgagg tgtgggtgag cgcaaaggtg tccctgacca tgactttgag   7320
gtactggtat ttgaagtcag tgtcgtcgca tccgccctgc tcccagagca aaaagtccgt   7380
gcgctttttg gaacgcggat ttggcagggc gaaggtgaca tcgttgaaga gtatctttcc   7440
cgcgcgaggc ataaagttgc gtgtgatgcg gaagggtccc ggcacctcgg aacggttgtt   7500
aattacctgg gcggcgagca cgatctcgtc aaagccgttg atgttgtggc ccacaatgta   7560
aagttccaag aagcgcggga tgcccttgat ggaaggcaat ttttttaagtt cctcgtaggt   7620
gagctcttca ggggagctga gcccgtgctc tgaaagggcc cagtctgcaa gatgagggtt   7680
ggaagcgacg aatgagctcc acaggtcacg ggccattagc atttgcaggt ggtcgcgaaa   7740
ggtcctaaac tggcgaccta tggccatttt ttctggggtg atgcagtaga aggtaagcgg   7800
gtcttgttcc cagcggtccc atccaaggtt cgcggctagg tctcgcgcgg cagtcactag   7860
aggctcatct ccgccgaact tcatgaccag catgaagggc acgagctgct tcccaaaggc   7920
ccccatccaa gtataggtct ctacatcgta ggtgacaaag agacgctcgg tgcgaggatg   7980
cgagccgatc gggaagaact ggatctcccg ccaccaattg gaggagtggc tattgatgtg   8040
gtgaaagtag aagtccctgc gacgggccga acactcgtgc tggcttttgt aaaaacgtgc   8100
gcagtactgg cagcggtgca cgggctgtac atcctgcacg aggttgacct gacgaccgcg   8160
cacaaggaag cagagtggga atttgagccc ctcgcctggc gggtttggct ggtggtcttc   8220
tacttcggct gcttgtcctt gaccgtctgg ctgctcgagg ggagttacgg tggatcggac   8280
caccacgccg cgcgagccca aagtccagat gtccgcgcgc ggcggtcgga gcttgatgac   8340
aacatcgcgc agatgggagc tgtccatggt ctggagctcc cgcggcgtca ggtcaggcgg   8400
gagctcctgc aggtttacct cgcatagacg ggtcagggcg cgggctagat ccaggtgata   8460
cctaatttcc aggggctggt tggtggcggc gtcgatggct tgcaagaggc cgcatccccg   8520
cggcgcgact acggtaccgc gcggcgggcg gtgggccgcg ggggtgtcct tggatgatgc   8580
atctaaaagc ggtgacgcgg gcgagccccc ggaggtaggg ggggctccgg acccgccggg   8640
agagggggca ggggcacgtc ggcgccgcgc gcgggcagga gctggtgctg cgcgcgtagg   8700
ttgctggcga acgcgacgac gcggcggttg atctcctgaa tctggcgcct ctgcgtgaag   8760
acgacgggcc cggtgagctt gagcctgaaa gagagttcga cagaatcaat ttcggtgtcg   8820
ttgacggcgg cctggcgcaa aatctcctgc acgtctcctg agttgtcttg ataggcgatc   8880
tcggccatga actgctcgat ctcttcctcc tggagatctc cgcgtccggc tcgctccacg   8940
gtggcggcga ggtcgttgga aatgcgggcc atgagctgcg agaaggcgtt gaggcctccc   9000
tcgttccaga cgcggctgta gaccacgccc ccttcggcat cgcgggcgcg catgaccacc   9060
tgcgcgagat tgagctccac gtgccgggcg aagacggcgt agtttcgcag gcgctgaaag   9120
aggtagttga gggtggtggc ggtgtgttct gccacgaaga agtacataac ccagcgtcgc   9180
aacgtggatt cgttgatatc ccccaaggcc tcaaggcgct ccatggcctc gtagaagtcc   9240
acggcgaagt tgaaaaactg ggagttgcgc gccgacacgg ttaactcctc ctccagaaga   9300
cggatgagct cggcgacagt gtcgcgcacc tcgcgctcaa aggctacagg ggcctcttct   9360
tcttcttcaa tctcctcttc cataagggcc tccccttctt cttcttctgg cggcggtggg   9420
ggaggggggga cacggcggcg acgacggcgc accgggaggc ggtcgacaaa gcgctcgatc   9480
atctccccgc ggcgacggcg catggtctcg gtgacggcgc ggccgttctc gcgggggcgc   9540
```

-continued agttggaaga cgccgcccgt catgtcccgg ttatgggttg gcggggggct gccatgcggc 9600
agggatacgg cgctaacgat gcatctcaac aattgttgtg taggtactcc gccgccgagg 9660
gacctgagcg agtccgcatc gaccggatcg gaaaacctct cgagaaaggc gtctaaccag 9720
tcacagtcgc aaggtaggct gagcaccgtg gcgggcggca gcgggcggcg gtcggggttg 9780
tttctggcgg aggtgctgct gatgatgtaa ttaaagtagg cggtcttgag acggcggatg 9840
gtcgacagaa gcaccatgtc cttgggtccg gcctgctgaa tgcgcaggcg gtcggccatg 9900
ccccaggctt cgttttgaca tcggcgcagg tctttgtagt agtcttgcat gagcctttct 9960
accggcactt cttcttctcc ttcctcttgt cctgcatctc ttgcatctat cgctgcggcg 10020
gcggcggagt ttggccgtag gtggcgccct cttcctccca tgcgtgtgac cccgaagccc 10080
ctcatcggct gaagcagggc taggtcggcg acaacgcgct cggctaatat ggcctgctgc 10140
acctgcgtga gggtagactg gaagtcatcc atgtccacaa agcggtggta tgcgcccgtg 10200
ttgatggtgt aagtgcagtt ggccataacg gaccagttaa cggtctggtg acccggctgc 10260
gagagctcgg tgtacctgag acgcgagtaa gccctcgagt caaatacgta gtcgttgcaa 10320
gtccgcacca ggtactggta tcccaccaaa aagtgcggcg gcggctggcg gtagaggggc 10380
cagcgtaggg tggccggggc tccgggggcg agatcttcca acataaggcg atgatatccg 10440
tagatgtacc tggacatcca ggtgatgccg gcggcggtgg tggaggcgcg cggaaagtcg 10500
cggacgcggt tccagatgtt gcgcagcggc aaaaagtgct ccatggtcgg gacgctctgg 10560
ccggtcaggc gcgcgcaatc gttgacgctc tagaccgtgc aaaaggagag cctgtaagcg 10620
ggcactcttc cgtggtctgg tggataaatt cgcaagggta tcatggcgga cgaccggggt 10680
tcgagccccg tatccggccg tccgccgtga tccatgcggt taccgcccgc gtgtcgaacc 10740
caggtgtgcg acgtcagaca acgggggagt gctccttttg gcttccttcc aggcgcggcg 10800
gctgctgcgc tagctttttt ggccactggc cgcgcgcagc gtaagcggtt aggctggaaa 10860
gcgaaagcat taagtggctc gctccctgta gccggagggt tattttccaa gggttgagtc 10920
gcgggacccc cggttcgagt ctcggaccgg ccggactgcg gcgaacgggg gtttgcctcc 10980
ccgtcatgca agaccccgct tgcaaattcc tccggaaaca gggacgagcc ccttttttgc 11040
ttttcccaga tgcatccggt gctgcggcag atgcgccccc ctcctcagca gcggcaagag 11100
caagagcagc ggcagacatg cagggcaccc tcccctcctc ctaccgcgtc aggaggggcg 11160
acatccgcgg ttgacgcggc agcagatggt gattacgaac ccccgcggcg ccgggcccgg 11220
cactacctgg acttggagga gggcgagggc ctggcgcggc taggagcgcc ctctcctgag 11280
cggtacccaa gggtgcagct gaagcgtgat acgcgtgagg cgtacgtgcc gcggcagaac 11340
ctgtttcgcg accgcgaggg agaggagccc gaggagatgc gggatcgaaa gttccacgca 11400
gggcgcgagc tgcggcatgg cctgaatcgc gagcggttgc tgcgcgagga ggactttgag 11460
cccgacgcgc gaaccgggat tagtcccgcg cgcgcacacg tggcggccgc cgacctggta 11520
accgcatacg agcagacggt gaaccaggag attaactttc aaaaaagctt taacaaccac 11580
gtgcgtacgc ttgtggcgcg cgaggaggtg gctataggac tgatgcatct gtgggacttt 11640
gtaagcgcgc tggagcaaaa cccaaatagc aagccgctca tggcgcagct gttccttata 11700
gtgcagcaca gcagggacaa cgaggcattc agggatgcgc tgctaaacat agtagagccc 11760
gagggccgct ggctgctcga tttgataaac atcctgcaga gcatagtggt gcaggagcgc 11820
agcttgagcc tggctgacaa ggtggccgcc atcaactatt ccatgcttag cctgggcaag 11880

-continued

```
ttttacgccc gcaagatata ccatacccct tacgttccca tagacaagga ggtaaagatc  11940
gaggggttct acatgcgcat ggcgctgaag gtgcttacct tgagcgacga cctgggcgtt  12000
tatcgcaacg agcgcatcca caaggccgtg agcgtgagcc ggcggcgcga gctcagcgac  12060
cgcgagctga tgcacagcct gcaaagggcc ctggctggca cgggcagcgg cgatagagag  12120
gccgagtcct actttgacgc gggcgctgac ctgcgctggg ccccaagccg acgcgccctg  12180
gaggcagctg gggccggacc tgggctggcg gtggcacccg cgcgcgctgg caacgtcggc  12240
ggcgtggagg aatatgacga ggacgatgag tacgagccag aggacggcga gtactaagcg  12300
gtgatgtttc tgatcagatg atgcaagacg caacggaccc ggcggtgcgg gcggcgctgc  12360
agagccagcc gtccggcctt aactccacgg acgactggcg ccaggtcatg gaccgcatca  12420
tgtcgctgac tgcgcgcaat cctgacgcgt tccggcagca gccgcaggcc aaccggctct  12480
ccgcaattct ggaagcggtg gtcccggcgc gcgcaaaccc cacgcacgag aaggtgctgg  12540
cgatcgtaaa cgcgctggcc gaaaacaggg ccatccggcc cgacgaggcc ggcctggtct  12600
acgacgcgct gcttcagcgc gtggctcgtt acaacagcgg caacgtgcag accaacctgg  12660
accggctggt gggggatgtg cgcgaggccg tggcgcagcg tgagcgcgcg cagcagcagg  12720
gcaacctggg ctccatggtt gcactaaacg ccttcctgag tacacagccc gccaacgtgc  12780
cgcggggaca ggaggactac accaactttg tgagcgcact gcggctaatg gtgactgaga  12840
caccgcaaag tgaggtgtac cagtctgggc cagactattt tttccagacc agtagacaag  12900
gcctgcagac cgtaaacctg agccaggctt tcaaaaactt gcaggggctg tggggggtgc  12960
gggctcccac aggcgaccgc gcgaccgtgt ctagcttgct gacgcccaac tcgcgcctgt  13020
tgctgctgct aatagcgccc ttcacggaca gtggcagcgt gtcccgggac acatacctag  13080
gtcacttgct gacactgtac cgcgaggcca taggtcaggc gcatgtggac gagcatactt  13140
tccaggagat tacaagtgtc agccgcgcgc tggggcagga ggacacgggc agcctggagg  13200
caaccctaaa ctacctgctg accaaccggc ggcagaagat cccctcgttg cacagtttaa  13260
acagcgagga ggagcgcatt ttgcgctacg tgcagcagag cgtgagcctt aacctgatgc  13320
gcgacggggt aacgcccagc gtggcgctgg acatgaccgc gcgcaacatg gaaccgggca  13380
tgtatgcctc aaaccggccg tttatcaacc gcctaatgga ctacttgcat cgcgcggccg  13440
ccgtgaaccc cgagtatttc accaatgcca tcttgaaccc gcactggcta ccgcccccctg  13500
gtttctacac cgggggattc gaggtgcccg agggtaacga tggattcctc tgggacgaca  13560
tagacgacag cgtgttttcc ccgcaaccgc agaccctgct agagttgcaa cagcgcgagc  13620
aggcagaggc ggcgctgcga aaggaaagct tccgcaggcc aagcagcttg tccgatctag  13680
gcgctgcggc cccgcggtca gatgctagta gcccatttcc aagcttgata gggtctctta  13740
ccagcactcg caccacccgc ccgcgcctgc tgggcgagga ggagtaccta aacaactcgc  13800
tgctgcagcc gcagcgcgaa aaaaacctgc ctccggcatt tcccaacaac gggatagaga  13860
gcctagtgga caagatgagt agatggaaga cgtacgcgca ggagcacagg gacgtgccag  13920
gcccgcgccc gcccacccgt cgtcaaaggc acgaccgtca gcggggtctg gtgtgggagg  13980
acgatgactc ggcagacgac agcagcgtcc tggatttggg agggagtggc aacccgtttg  14040
cgcaccttcg ccccaggctg gggagaatgt tttaaaaaaa aaaaagcatg atgcaaaata  14100
aaaaactcac caaggccatg gcaccgagcg ttggttttct tgtattcccc ttagtatgcg  14160
gcgcgcggcg atgtatgagg aaggtcctcc tccctcctac gagagtgtgg tgagcgcggc  14220
gccagtggcg gcggcgctgg gttctccctt cgatgctccc ctggacccgc cgtttgtgcc  14280
```

tccgcggtac ctgcggccta ccggggggag aaacagcatc cgttactctg agttggcacc 14340
cctattcgac accacccgtg tgtacctggt ggacaacaag tcaacggatg tggcatccct 14400
gaactaccag aacgaccaca gcaactttct gaccacggtc attcaaaaca atgactacag 14460
cccgggggag gcaagcacac agaccatcaa tcttgacgac cggtcgcact ggggcggcga 14520
cctgaaaacc atcctgcata ccaacatgcc aaatgtgaac gagttcatgt ttaccaataa 14580
gtttaaggcg cgggtgatgg tgtcgcgctt gcctactaag gacaatcagg tggagctgaa 14640
atacgagtgg gtggagttca cgctgcccga gggcaactac tccgagacca tgaccataga 14700
ccttatgaac aacgcgatcg tggagcacta cttgaaagtg ggcagacaga acggggttct 14760
ggaaagcgac atcggggtaa agtttgacac ccgcaacttc agactggggt ttgaccccgt 14820
cactggtctt gtcatgcctg ggtatatac aaacgaagcc ttccatccag acatcatttt 14880
gctgccagga tgcggggtgg acttcaccca cagccgcctg agcaacttgt tgggcatccg 14940
caagcggcaa cccttccagg agggctttag gatcacctac gatgatctgg agggtggtaa 15000
cattcccgca ctgttggatg tggacgccta ccaggcgagc ttgaaagatg acaccgaaca 15060
gggcgggggt ggcgcaggcg gcagcaacag cagtggcagc ggcgcggaag agaactccaa 15120
cgcggcagcc gcggcaatgc agccggtgga ggacatgaac gatcatgcca ttcgcggcga 15180
cacctttgcc acacgggctg aggagaagcg cgctgaggcc gaagcagcgg ccgaagctgc 15240
cgcccccgct gcgcaacccg aggtcgagaa gcctcagaag aaaccggtga tcaaacccct 15300
gacagaggac agcaagaaac gcagttacaa cctaataagc aatgacagca ccttcaccca 15360
gtaccgcagc tggtaccttg catacaacta cggcgaccct cagaccggaa tccgctcatg 15420
gaccctgctt tgcactcctg acgtaacctg cggctcggag caggtctact ggtcgttgcc 15480
agacatgatg caagaccccg tgaccttccg ctccacgcgc cagatcagca actttccggt 15540
ggtgggcgcc gagctgttgc ccgtgcactc caagagcttc tacaacgacc aggccgtcta 15600
ctcccaactc atccgccagt ttacctctct gacccacgtg ttcaatcgct ttcccgagaa 15660
ccagattttg gcgcgcccgc cagcccccac catcaccacc gtcagtgaaa acgttcctgc 15720
tctcacagat cacgggacgc taccgctgcg caacagcatc ggaggagtcc agcgagtgac 15780
cattactgac gccagacgcc gcacctgccc ctacgtttac aaggccctgg gcatagtctc 15840
gccgcgcgtc ctatcgagcc gcactttttg agcaagcatg tccatcctta tatcgcccag 15900
caataacaca ggctggggcc tgcgcttccc aagcaagatg tttggcgggg ccaagaagcg 15960
ctccgaccaa cacccagtgc gcgtgcgcgg gcactaccgc gcgccctggg gcgcgcacaa 16020
acgcggccgc actgggcgca ccaccgtcga tgacgccatc gacgcggtgg tggaggaggc 16080
gcgcaactac acgcccacgc cgccaccagt gtccacagtg gacgcggcca ttcagaccgt 16140
ggtgcgcgga gcccggcgct atgctaaaat gaagagacgg cggaggcgcg tagcacgtcg 16200
ccaccgccgc cgacccggca ctgccgccca acgcgcggcg gcggccctgc ttaaccgcgc 16260
acgtcgcacc ggccgacggg cggccatgcg ggccgctcga aggctggccg cgggtattgt 16320
cactgtgccc cccaggtcca ggcgacgagc ggccgccgca gcagccgcgg ccattagtgc 16380
tatgactcag ggtcgcaggg gcaacgtgta ttgggtgcgc gactcggtta gcggcctgcg 16440
cgtgcccgtg cgcacccgcc ccccgcgcaa ctagattgca agaaaaaact acttagactc 16500
gtactgttgt atgtatccag cggcggcggc gcgcaacgaa gctatgtcca agcgcaaaat 16560
caaagaagag atgctccagg tcatcgcgcc ggagatctat ggccccccga agaaggaaga 16620

-continued

```
gcaggattac aagccccgaa agctaaagcg ggtcaaaaag aaaaagaaag atgatgatga  16680
tgaacttgac gacgaggtgg aactgctgca cgctaccgcg cccaggcgac gggtacagtg  16740
gaaaggtcga cgcgtaaaac gtgttttgcg acccggcacc accgtagtct ttacgcccgg  16800
tgagcgctcc acccgcacct acaagcgcgt gtatgatgag gtgtacggcg acgaggacct  16860
gcttgagcag gccaacgagc gcctcgggga gtttgcctac ggaaagcggc ataaggacat  16920
gctggcgttg ccgctggacg agggcaaccc aacacctagc ctaaagcccg taacactgca  16980
gcaggtgctg cccgcgcttg caccgtccga agaaaagcgc ggcctaaagc gcgagtctgg  17040
tgacttggca cccaccgtgc agctgatggt acccaagcgc cagcgactgg aagatgtctt  17100
ggaaaaaatg accgtggaac ctgggctgga gcccgaggtc cgcgtgcggc caatcaagca  17160
ggtggcgccg ggactgggcg tgcagaccgt ggacgttcag atacccacta ccagtagcac  17220
cagtattgcc accgccacag agggcatgga gacacaaacg tccccggttg cctcagcggt  17280
ggcggatgcc gcggtgcagg cggtcgctgc ggccgcgtcc aagacctcta cggaggtgca  17340
aacggacccg tggatgtttc gcgtttcagc cccccggcgc ccgcgcggtt cgaggaagta  17400
cggcgccgcc agcgcgctac tgcccgaata tgccctacat ccttccattg cgcctacccc  17460
cggctatcgt ggctacacct accgccccag aagacgagca actacccgac gccgaaccac  17520
cactggaacc cgccgccgcc gtcgccgtcg ccagcccgtg ctggccccga tttccgtgcg  17580
cagggtggct cgcgaaggag gcaggaccct ggtgctgcca acagcgcgct accaccccag  17640
catcgtttaa aagccggtct ttgtggttct tgcagatatg gccctcacct gccgcctccg  17700
tttcccggtg ccgggattcc gaggaagaat gcaccgtagg aggggcatgg ccggccacgg  17760
cctgacgggc ggcatgcgtc gtgcgcacca ccggcggcgg cgcgcgtcgc accgtcgcat  17820
gcgcggcggt atcctgcccc tccttattcc actgatcgcc gcggcgattg gcgccgtgcc  17880
cggaattgca tccgtggcct tgcaggcgca gagacactga ttaaaaacaa gttgcatgtg  17940
gaaaaatcaa aataaaaagt ctggactctc acgctcgctt ggtcctgtaa ctattttgta  18000
gaatggaaga catcaacttt gcgtctctgg ccccgcgaca cggctcgcgc ccgttcatgg  18060
gaaactggca agatatcggc accagcaata tgagcggtgg cgccttcagc tggggctcgc  18120
tgtggagcgg cattaaaaat ttcggttcca ccgttaagaa ctatggcagc aaggcctgga  18180
acagcagcac aggccagatg ctgagggata agttgaaaga gcaaaatttc caacaaaagg  18240
tggtagatgg cctggcctct ggcattagcg gggtggtgga cctggccaac caggcagtgc  18300
aaaataagat taacagtaag cttgatcccc gccctcccgt agaggagcct ccaccggccg  18360
tggagacagt gtctccagag ggcgtggcg aaaagcgtcc gcgccccgac agggaagaaa  18420
ctctggtgac gcaaatagac gagcctccct cgtacgagga ggcactaaag caaggcctgc  18480
ccaccacccg tcccatcgcg cccatggcta ccggagtgct gggccagcac acacccgtaa  18540
cgctggacct gcctcccccc gccgacaccc agcagaaacc tgtgctgcca ggcccgaccg  18600
ccgttgttgt aacccgtcct agccgcgcgt ccctgcgccg cgccgccagc ggtccgcgat  18660
cgttgcggcc cgtagccagt ggcaactggc aaagcacact gaacagcatc gtgggtctgg  18720
gggtgcaatc cctgaagcgc cgacgatgct tctgaatagc taacgtgtcg tatgtgtgtc  18780
atgtatgcgt ccatgtcgcc gccagaggag ctgctgagcc gccgcgcgcc cgctttccaa  18840
gatggctacc ccttcgatga tgccgcagtg gtcttacatg cacatctcgg gccaggacgc  18900
ctcggagtac ctgagccccg ggctggtgca gtttgcccgc gccaccgaga cgtacttcag  18960
cctgaataac aagtttagaa accccacggt ggcgcctacg cacgacgtga ccacagaccg  19020
```

-continued

```
gtcccagcgt ttgacgctgc ggttcatccc tgtggaccgt gaggatactg cgtactcgta  19080
caaggcgcgg ttcaccctag ctgtgggtga taaccgtgtg ctggacatgg cttccacgta  19140
ctttgacatc cgcggcgtgc tggacagggg ccctactttt aagccctact ctggcactgc  19200
ctacaacgcc ctggctccca agggtgcccc aaatccttgc gaatgggatg aagctgctac  19260
tgctcttgaa ataaacctag aagaagagga cgatgacaac gaagacgaag tagacgagca  19320
agctgagcag caaaaaactc acgtatttgg gcaggcgcct tattctggta taaatattac  19380
aaaggagggt attcaaatag gtgtcgaagg tcaaacacct aaatatgccg ataaaacatt  19440
tcaacctgaa cctcaaatag gagaatctca gtggtacgaa actgaaatta atcatgcagc  19500
tgggagagtc cttaaaaaga ctaccccaat gaaaccatgt tacggttcat atgcaaaacc  19560
cacaaatgaa aatggagggc aaggcattct tgtaaagcaa caaaatggaa agctagaaag  19620
tcaagtggaa atgcaatttt tctcaactac tgaggcgacc gcaggcaatg gtgataactt  19680
gactcctaaa gtggtattgt acagtgaaga tgtagatata gaaaccccag acactcatat  19740
ttcttacatg cccactatta aggaaggtaa ctcacgagaa ctaatgggcc aacaatctat  19800
gcccaacagg cctaattaca ttgcttttag ggacaatttt attggtctaa tgtattacaa  19860
cagcacgggt aatatgggtg ttctggcggg ccaagcatcg cagttgaatg ctgttgtaga  19920
tttgcaagac agaaacacag agctttcata ccagcttttg cttgattcca ttggtgatag  19980
aaccaggtac ttttctatgt ggaatcaggc tgttgacagc tatgatccag atgttagaat  20040
tattgaaaat catggaactg aagatgaact tccaaattac tgctttccac tgggaggtgt  20100
gattaataca gagactctta ccaaggtaaa acctaaaaca ggtcaggaaa atggatggga  20160
aaaagatgct acagaatttt cagataaaaa tgaaataaga gttggaaata attttgccat  20220
ggaaatcaat ctaaatgcca acctgtggag aaatttcctg tactccaaca tagcgctgta  20280
tttgcccgac aagctaaagt acagtccttc caacgtaaaa atttctgata acccaaacac  20340
ctacgactac atgaacaagc gagtggtggc tcccgggtta gtggactgct acattaacct  20400
tggagcacgc tggtcccttg actatatgga caacgtcaac ccatttaacc accaccgcaa  20460
tgctggcctg cgctaccgct caatgttgct gggcaatggt cgctatgtgc ccttccacat  20520
ccaggtgcct cagaagttct ttgccattaa aaacctcctt ctcctgccgg gctcatacac  20580
ctacgagtgg aacttcagga aggatgttaa catggttctg cagagctccc taggaaatga  20640
cctaagggtt gacggagcca gcattaagtt tgatagcatt tgcctttacg ccaccttctt  20700
ccccatggcc cacaacaccg cctccacgct tgaggccatg cttagaaacg acaccaacga  20760
ccagtccttt aacgactatc tctccgccgc caacatgctc taccctatac ccgccaacgc  20820
taccaacgtg cccatatcca tcccctcccg caactgggcg gctttccgcg gctgggcctt  20880
cacgcgcctt aagactaagg aaaccccatc actgggctcg ggctacgacc cttattacac  20940
ctactctggc tctataccct acctagatgg aacctttttac ctcaaccaca cctttaagaa  21000
ggtggccatt acctttgact cttctgtcag ctggcctggc aatgaccgcc tgcttacccc  21060
caacgagttt gaaattaagc gctcagttga cggggagggt tacaacgttg cccagtgtaa  21120
catgaccaaa gactggttcc tggtacaaat gctagctaac tacaacattg gctaccaggg  21180
cttctatatc ccagagagct acaaggaccg catgtactcc ttctttagaa acttccagcc  21240
catgagccgt caggtggtgg atgatactaa atacaaggac taccaacagg tgggcatcct  21300
acaccaacac aacaactctg gatttgttgg ctaccttgcc cccaccatgc gcgaaggaca  21360
```

```
ggcctaccct gctaacttcc cctatccgct tataggcaag accgcagttg acagcattac  21420
ccagaaaaag tttctttgcg atcgcaccct ttggcgcatc ccattctcca gtaactttat  21480
gtccatgggc gcactcacag acctgggcca aaaccttctc tacgccaact ccgcccacgc  21540
gctagacatg acttttgagg tggatcccat ggacgagccc acccttcttt atgttttgtt  21600
tgaagtcttt gacgtggtcc gtgtgcaccg gccgcaccgc ggcgtcatcg aaaccgtgta  21660
cctgcgcacg cccttctcgg ccggcaacgc cacaacataa agaagcaagc aacatcaaca  21720
acagctgccg ccatgggctc cagtgagcag gaactgaaag ccattgtcaa agatcttggt  21780
tgtgggccat attttttggg cacctatgac aagcgctttc caggctttgt ttctccacac  21840
aagctcgcct gcgccatagt caatacggcc ggtcgcgaga ctgggggcgt acactggatg  21900
gcctttgcct ggaacccgca ctcaaaaaca tgctacctct ttgagccctt tggcttttct  21960
gaccagcgac tcaagcaggt ttaccagttt gagtacgagt cactcctgcg ccgtagcgcc  22020
attgcttctt cccccgaccg ctgtataacg ctggaaaagt ccacccaaag cgtacagggg  22080
cccaactcgg ccgcctgtgg actattctgc tgcatgtttc tccacgcctt tgccaactgg  22140
ccccaaactc ccatggatca caaccccacc atgaacctta ttaccggggt acccaactcc  22200
atgctcaaca gtccccaggt acagcccacc ctgcgtcgca accaggaaca gctctacagc  22260
ttcctggagc gccactcgcc ctacttccgc agccacagtg cgcagattag gagcgccact  22320
tctttttgtc acttgaaaaa catgtaaaaa taatgtacta gagacacttt caataaaggc  22380
aaatgctttt atttgtacac tctcgggtga ttatttaccc ccacccttgc cgtctgcgcc  22440
gtttaaaaat caaaggggtt ctgccgcgca tcgctatgcg ccactggcag ggacacgttg  22500
cgatactggt gtttagtgct ccacttaaac tcaggcacaa ccatccgcgg cagctcggtg  22560
aagttttcac tccacaggct gcgcaccatc accaacgcgt ttagcaggtc gggcgccgat  22620
atcttgaagt cgcagttggg gcctccgccc tgcgcgcgcg agttgcgata cacagggttg  22680
cagcactgga acactatcag cgccgggtgg tgcacgctgg ccagcacgct cttgtcggag  22740
atcagatccg cgtccaggtc ctccgcgttg ctcagggcga acggagtcaa ctttggtagc  22800
tgccttccca aaaagggcgc gtgcccaggc tttgagttgc actcgcaccg tagtggcatc  22860
aaaaggtgac cgtgcccggt ctgggcgtta ggatacagcg cctgcataaa agccttgatc  22920
tgcttaaaag ccacctgagc ctttgcgcct tcagagaaga acatgccgca agacttgccg  22980
gaaaactgat tggccggaca ggccgcgtcg tgcacgcagc accttgcgtc ggtgttggag  23040
atctgcacca catttcggcc ccaccggttc ttcacgatct tggccttgct agactgctcc  23100
ttcagcgcgc gctgcccgtt ttcgctcgtc acatccattt caatcacgtg ctccttattt  23160
atcataatgc ttccgtgtag acacttaagc tcgccttcga tctcagcgca gcggtgcagc  23220
cacaacgcgc agcccgtggg ctcgtgatgc ttgtaggtca cctctgcaaa cgactgcagg  23280
tacgcctgca ggaatcgccc catcatcgtc acaaaggtct tgttgctggt gaaggtcagc  23340
tgcaacccgc ggtgctcctc gttcagccag gtcttgcata cggccgccag agcttccact  23400
tggtcaggca gtagtttgaa gttcgccttt agatcgttat ccacgtggta cttgtccatc  23460
agcgcgcgcg cagcctccat gcccttctcc cacgcagaca cgatcggcac actcagcggg  23520
ttcatcaccg taatttcact ttccgcttcg ctgggctctt cctcttcctc ttgcgtccgc  23580
ataccacgcg ccactgggtc gtcttcattc agccgccgca ctgtgcgctt acctcctttg  23640
ccatgcttga ttagcaccgg tgggttgctg aaacccacca tttgtagcgc cacatcttct  23700
ctttcttcct cgctgtccac gattacctct ggtgatggcg ggcgctcggg cttgggagaa  23760
```

gggcgcttct ttttcttctt gggcgcaatg gccaaatccg ccgccgaggt cgatggccgc 23820
gggctgggtg tgcgcggcac cagcgcgtct tgtgatgagt cttcctcgtc ctcggactcg 23880
atacgccgcc tcatccgctt ttttgggggc gcccggggag gcggcggcga cggggacggg 23940
gacgacacgt cctccatggt tgggggacgt cgcgccgcac cgcgtccgcg ctcgggggtg 24000
gtttcgcgct gctcctcttc ccgactggcc atttccttct cctataggca gaaaaagatc 24060
atggagtcag tcgagaagaa ggacagccta accgcccccct ctgagttcgc caccaccgcc 24120
tccaccgatg ccgccaacgc gcctaccacc ttccccgtcg aggcaccccc gcttgaggag 24180
gaggaagtga ttatcgagca ggacccaggt tttgtaagcg aagacgacga ggaccgctca 24240
gtaccaacag aggataaaaa gcaagaccag gacaacgcag aggcaaacga ggaacaagtc 24300
gggcgggggg acgaaaggca tggcgactac ctagatgtgg gagacgacgt gctgttgaag 24360
catctgcagc gccagtgcgc cattatctgc gacgcgttgc aagagcgcag cgatgtgccc 24420
ctcgccatag cggatgtcag ccttgcctac gaacgccacc tattctcacc gcgcgtaccc 24480
cccaaacgcc aagaaaacgg cacatgcgag cccaacccgc gcctcaactt ctaccccgta 24540
tttgccgtgc cagaggtgct tgccacctat cacatctttt tccaaaactg caagataccc 24600
ctatcctgcc gtgccaaccg cagccgagcg gacaagcagc tggccttgcg gcagggcgct 24660
gtcatacctg atatcgcctc gctcaacgaa gtgccaaaaa tctttgaggg tcttggacgc 24720
gacgagaagc gcgcggcaaa cgctctgcaa caggaaaaca gcgaaaatga aagtcactct 24780
ggagtgttgg tggaactcga gggtgacaac gcgcgcctag ccgtactaaa acgcagcatc 24840
gaggtcaccc actttgccta cccggcactt aacctacccc ccaaggtcat gagcacagtc 24900
atgagtgagc tgatcgtgcg ccgtgcgcag cccctggaga gggatgcaaa tttgcaagaa 24960
caaacagagg agggcctacc cgcagttggc gacgagcagc tagcgcgctg gcttcaaacg 25020
cgcgagcctg ccgacttgga ggagcgacgc aaactaatga tggccgcagt gctcgttacc 25080
gtggagcttg agtgcatgca gcggttcttt gctgacccgg agatgcagcg caagctagag 25140
gaaacattgc actacacctt tcgacagggc tacgtacgcc aggcctgcaa gatctccaac 25200
gtggagctct gcaacctggt ctcctacctt ggaattttgc acgaaaaccg ccttgggcaa 25260
aacgtgcttc attccacgct caagggcgag gcgcgccgcg actacgtccg cgactgcgtt 25320
tacttatttc tatgctacac ctggcagacg gccatgggcg tttggcagca gtgcttggag 25380
gagtgcaacc tcaaggagct gcagaaactg ctaaagcaaa acttgaagga cctatggacg 25440
gccttcaacg agcgctccgt ggccgcgcac ctggcggaca tcattttccc cgaacgcctg 25500
cttaaaaccc tgcaacaggg tctgccagac ttcaccagtc aaagcatgtt gcagaacttt 25560
aggaacttta tcctagagcg ctcaggaatc ttgcccgcca cctgctgtgc acttcctagc 25620
gactttgtgc ccattaagta ccgcgaatgc cctccgccgc tttggggcca ctgctacctt 25680
ctgcagctag ccaactacct tgcctaccac tctgacataa tggaagacgt gagcggtgac 25740
ggtctactgg agtgtcactg tcgctgcaac ctatgcaccc cgcaccgctc cctggtttgc 25800
aattcgcagc tgcttaacga aagtcaaatt atcggtacct ttgagctgca gggtccctcg 25860
cctgacgaaa agtccgcggc tccggggttg aaactcactc cggggctgtg gacgtcggct 25920
taccttcgca aatttgtacc tgaggactac cacgcccacg agattaggtt ctacgaagac 25980
caatcccgcc cgccaaatgc ggagcttacc gcctgcgtca ttacccaggg ccacattctt 26040
ggccaattgc aagccatcaa caaagcccgc caagagtttc tgctacgaaa gggacggggg 26100

-continued

```
gtttacttgg acccccagtc cggcgaggag ctcaacccaa tccccccgcc gccgcagccc  26160
tatcagcagc agccgcgggc ccttgcttcc caggatggca cccaaaaaga agctgcagct  26220
gccgccgcca cccacggacg aggaggaata ctgggacagt caggcagagg aggttttgga  26280
cgaggaggag gaggacatga tggaagactg ggagagccta gacgaggaag cttccgaggt  26340
cgaagaggtg tcagacgaaa caccgtcacc ctcggtcgca ttcccctcgc cggcgcccca  26400
gaaatcggca accggttcca gcatggctac aacctccgct cctcaggcgc cgccggcact  26460
gcccgttcgc cgacccaacc gtagatggga caccactgga accagggccg gtaagtccaa  26520
gcagccgccg ccgttagccc aagagcaaca acagcgccaa ggctaccgct catggcgcgg  26580
gcacaagaac gccatagttg cttgcttgca agactgtggg ggcaacatct ccttcgcccg  26640
ccgctttctt ctctaccatc acggcgtggc cttcccccgt aacatcctgc attactaccg  26700
tcatctctac agcccatact gcaccggcgg cagcggcagc ggcagcaaca gcagcggcca  26760
cacagaagca aaggcgaccg gatagcaaga ctctgacaaa gcccaagaaa tccacagcgg  26820
cggcagcagc aggaggagga gcgctgcgtc tggcgcccaa cgaacccgta tcgacccgcg  26880
agcttagaaa caggattttt cccactctgt atgctatatt tcaacagagc aggggccaag  26940
aacaagagct gaaaataaaa aacaggtctc tgcgatccct cacccgcagc tgcctgtatc  27000
acaaaagcga agatcagctt cggcgcacgc tggaagacgc ggaggctctc ttcagtaaat  27060
actgcgcgct gactcttaag gactagtttc gcgccctttc tcaaatttaa gcgcgaaaac  27120
tacgtcatct ccagcggcca cacccggcgc cagcacctgt cgtcagcgcc attatgagca  27180
aggaaattcc cacgccctac atgtggagtt accagccaca aatgggactt gcggctggag  27240
ctgcccaaga ctactcaacc cgaataaact acatgagcgc gggaccccac atgatatccc  27300
gggtcaacgg aatccgcgcc caccgaaacc gaattctctt ggaacaggcg gctattacca  27360
ccacacctcg taataacctt aatccccgta gttggcccgc tgccctggtg taccaggaaa  27420
gtcccgctcc caccactgtg gtacttccca gagacgccca ggccgaagtt cagatgacta  27480
actcaggggc gcagcttgcg ggcggctttc gtcacagggt gcggtcgccc gggcagggta  27540
taactcacct gacaatcaga gggcgaggta ttcagctcaa cgacgagtcg gtgagctcct  27600
cgcttggtct ccgtccggac gggacatttc agatcggcgg cgccggccgt ccttcattca  27660
cgcctcgtca ggcaatccta actctgcaga cctcgtcctc tgagccgcgc tctggaggca  27720
ttggaactct gcaatttatt gaggagtttg tgccatcggt ctactttaac cccttctcgg  27780
gacctcccgg ccactatccg gatcaattta ttcctaactt tgacgcggta aaggactcgg  27840
cggacggcta cgactgaatg ttaagtggag aggcagagca actgcgcctg aaacacctgg  27900
tccactgtcg ccgccacaag tgctttgccc gcgactccgg tgagttttgc tactttgaat  27960
tgcccgagga tcatatcgag ggcccggcgc acggcgtccg gcttaccgcc cagggagagc  28020
ttgcccgtag cctgattcgg gagtttaccc agcgcccccct gctagttgag cgggacaggg  28080
gaccctgtgt tctcactgtg atttgcaact gtcctaacct tggattacat caagatcttt  28140
gttgccatct ctgtgctgag tataataaat acagaaatta aaatatactg gggctcctat  28200
cgccatcctg taaacgccac cgtcttcacc cgcccaagca aaccaaggcg aaccttacct  28260
ggtactttta acatctctcc ctctgtgatt tacaacagtt tcaacccaga cggagtgagt  28320
ctacgagaga acctctccga gctcagctac tccatcagaa aaaacaccac cctccttacc  28380
tgccgggaac gtacgagtgc gtcaccggcc gctgcaccac acctaccgcc tgaccgtaaa  28440
ccagactttt tccggacaga cctcaataac tctgtttacc agaacaggag gtgagcttag  28500
```

-continued

```
aaaacccttta gggtattagg ccaaaggcgc agctactgtg gggtttatga acaattcaag  28560
caactctacg ggctattcta attcaggttt ctctagaatc ggggttgggg ttattctctg  28620
tcttgtgatt ctctttattc ttatactaac gcttctctgc ctaaggctcg ccgcctgctg  28680
tgtgcacatt tgcatttatt gtcagctttt taaacgctgg ggtcgccacc caagatgatt  28740
aggtacataa tcctaggttt actcaccctt gcgtcagccc acggtaccac ccaaaaggtg  28800
gattttaagg agccagcctg taatgttaca ttcgcagctg aagctaatga gtgcaccact  28860
cttataaaat gcaccacaga acatgaaaag ctgcttattc gccacaaaaa caaaattggc  28920
aagtatgctg tttatgctat ttggcagcca ggtgacacta cagagtataa tgttacagtt  28980
ttccagggta aaagtcataa aacttttatg tatacttttc cattttatga aatgtgcgac  29040
attaccatgt acatgagcaa acagtataag ttgtggcccc cacaaaattg tgtggaaaac  29100
actggcactt tctgctgcac tgctatgcta attacagtgc tcgctttggt ctgtacccta  29160
ctctatatta aatacaaaag cagacgcagc tttattgagg aaaagaaaat gccttaattt  29220
actaagttac aaagctaatg tcaccactaa ctgctttact cgctgcttgc aaaacaaatt  29280
caaaaagtta gcattataat tagaatagga tttaaacccc ccggtcattt cctgctcaat  29340
accattcccc tgaacaattg actctatgtg ggatatgctc cagcgctaca accttgaagt  29400
caggcttcct ggatgtcagc atctgacttt ggccagcacc tgtcccgcgg atttgttcca  29460
gtccaactac agcgacccac cctaacagag atgaccaaca caaccaacgc ggccgccgct  29520
accggactta catctaccac aaatacaccc caagtttctg cctttgtcaa taactgggat  29580
aacttgggca tgtggtggtt ctccatagcg cttatgtttg tatgccttat tattatgtgg  29640
ctcatctgct gcctaaagcg caaacgcgcc cgaccaccca tctatagtcc catcattgtg  29700
ctacacccaa acaatgatgg aatccataga ttggacggac tgaaacacat gttcttttct  29760
cttacagtat gattaaatga gacatgattc ctcgagtttt tatattactg acccttgttg  29820
cgctttttttg tgcgtgctcc acattggctg cggtttctca catcgaagta gactgcattc  29880
cagccttcac agtctatttg ctttacggat ttgtcaccct cacgctcatc tgcagcctca  29940
tcactgtggt catcgccttt atccagtgca ttgactgggt ctgtgtgcgc tttgcatatc  30000
tcagacacca tccccagtac agggacagga ctatagctga gcttcttaga attctttaat  30060
tatgaaattt actgtgactt ttctgctgat tatttgcacc ctatctgcgt tttgttcccc  30120
gacctccaag cctcaaagac atatatcatg cagattcact cgtatatgga atattccaag  30180
ttgctacaat gaaaaaagcg atctttccga agcctggtta tatgcaatca tctctgttat  30240
ggtgttctgc agtaccatct tagccctagc tatatatccc taccttgaca ttggctggaa  30300
acgaatagat gccatgaacc acccaacttt ccccgcgccc gctatgcttc cactgcaaca  30360
agttgttgcc ggcggctttg tcccagccaa tcagcctcgc ccccacttctc ccacccccac  30420
tgaaatcagc tactttaatc taacaggagg agatgactga caccctagat ctagaaatgg  30480
acggaattat tacagagcag cgcctgctag aaagacgcag ggcagcggcc gagcaacagc  30540
gcatgaatca agagctccaa gacatggtta acttgcacca gtgcaaaagg ggtatctttt  30600
gtctggtaaa gcaggccaaa gtcacctacg acagtaatac caccggacac cgccttagct  30660
acaagttgcc aaccaagcgt cagaaattgg tggtcatggt gggagaaaag cccattacca  30720
taactcagca ctcggtagaa accgaaggct gcattcactc accttgtcaa ggacctgagg  30780
atctctgcac ccttattaag accctgtgcg gtctcaaaga tcttattccc tttaactaat  30840
```

-continued

```
aaaaaaaaat aataaagcat cacttactta aaatcagtta gcaaatttct gtccagttta  30900
ttcagcagca cctccttgcc ctcctcccag ctctggtatt gcagcttcct cctggctgca  30960
aactttctcc acaatctaaa tggaatgtca gtttcctcct gttcctgtcc atccgcaccc  31020
actatcttca tgttgttgca gatgaagcgc gcaagaccgt ctgaagatac cttcaacccc  31080
gtgtatccat atgacacgga aaccggtcct ccaactgtgc cttttcttac tcctcccttt  31140
gtatccccca atgggtttca agagagtccc cctggggtac tctctttgcg cctatccgaa  31200
cctctagtta cctccaatgg catgcttgcg ctcaaaatgg gcaacggcct ctctctggac  31260
gaggccggca accttacctc ccaaaatgta accactgtga gcccacctct caaaaaaacc  31320
aagtcaaaca taaacctgga aatatctgca cccctcacag ttacctcaga agccctaact  31380
gtggctgccg ccgcacctct aatggtcgcg ggcaacacac tcaccatgca atcacaggcc  31440
ccgctaaccg tgcacgactc caaacttagc attgccaccc aaggacccct cacagtgtca  31500
gaaggaaagc tagccctgca aacatcaggc cccctcacca ccaccgatag cagtaccctt  31560
actatcactg cctcaccccc tctaactact gccactggta gcttgggcat tgacttgaaa  31620
gagcccattt atacacaaaa tggaaaacta ggactaaagt acggggctcc tttgcatgta  31680
acagacgacc taaacacttt gaccgtagca actggtccag gtgtgactat taataatact  31740
tccttgcaaa ctaaagttac tggagccttg ggttttgatt cacaaggcaa tatgcaactt  31800
aatgtagcag gaggactaag gattgattct caaaacagac gccttatact tgatgttagt  31860
tatccgtttg atgctcaaaa ccaactaaat ctaagactag gacagggccc tctttttata  31920
aactcagccc acaacttgga tattaactac aacaaaggcc tttacttgtt tacagcttca  31980
aacaattcca aaaagcttga ggttaaccta agcactgcca aggggttgat gtttgacgct  32040
acagccatag ccattaatgc aggagatggg cttgaatttg gttcacctaa tgcaccaaac  32100
acaaatcccc tcaaaacaaa aattggccat ggcctagaat ttgattcaaa caaggctatg  32160
gttcctaaac taggaactgg ccttagtttt gacagcacag gtgccattac agtaggaaac  32220
aaaaataatg ataagctaac tttgtggacc acaccagctc catctcctaa ctgtagacta  32280
aatgcagaga aagatgctaa actcactttg gtcttaacaa aatgtggcag tcaaatactt  32340
gctacagttt cagttttggc tgttaaaggc agtttggctc caatatctgg aacagttcaa  32400
agtgctcatc ttattataag atttgacgaa aatggagtgc tactaaacaa ttccttcctg  32460
gacccagaat attggaactt tagaaatgga gatcttactg aaggcacagc ctatacaaac  32520
gctgttggat ttatgcctaa cctatcagct tatccaaaat ctcacggtaa aactgccaaa  32580
agtaacattg tcagtcaagt ttacttaaac ggagacaaaa ctaaacctgt aacactaacc  32640
attacactaa acggtacaca ggaaacagga gacacaactc caagtgcata ctctatgtca  32700
ttttcatggg actggtctgg ccacaactac attaatgaaa tatttgccac atcctcttac  32760
actttttcat acattgccca agaataaaga atcgtttgtg ttatgtttca acgtgtttat  32820
ttttcaattg cagaaaattt caagtcattt ttcattcagt agtatagccc caccaccaca  32880
tagcttatac agatcaccgt accttaatca aactcacaga accctagtat tcaacctgcc  32940
acctccctcc caacacacag agtacacagt cctttctccc cggctggcct taaaaagcat  33000
catatcatgg gtaacagaca tattcttagg tgttatattc cacacggttt cctgtcgagc  33060
caaacgctca tcagtgatat taataaactc cccgggcagc tcacttaagt tcatgtcgct  33120
gtccagctgc tgagccacag gctgctgtcc aacttgcggt tgcttaacgg gcggcgaagg  33180
agaagtccac gcctacatgg gggtagagtc ataatcgtgc atcaggatag ggcggtggtg  33240
```

-continued

```
ctgcagcagc gcgcgaataa actgctgccg ccgccgctcc gtcctgcagg aatacaacat  33300
ggcagtggtc tcctcagcga tgattcgcac cgcccgcagc ataaggcgcc ttgtcctccg  33360
ggcacagcag cgcaccctga tctcacttaa atcagcacag taactgcagc acagcaccac  33420
aatattgttc aaaatcccac agtgcaaggc gctgtatcca aagctcatgg cggggaccac  33480
agaacccacg tggccatcat accacaagcg caggtagatt aagtggcgac ccctcataaa  33540
cacgctggac ataaacatta cctcttttgg catgttgtaa ttcaccacct cccggtacca  33600
tataaacctc tgattaaaca tggcgccatc caccaccatc ctaaaccagc tggccaaaac  33660
ctgcccgccg gctatacact gcagggaacc gggactggaa caatgacagt ggagagccca  33720
ggactcgtaa ccatggatca tcatgctcgt catgatatca atgttggcac aacacaggca  33780
cacgtgcata cacttcctca ggattacaag ctcctcccgc gttagaacca tatcccaggg  33840
aacaacccat tcctgaatca gcgtaaatcc cacactgcag ggaagacctc gcacgtaact  33900
cacgttgtgc attgtcaaag tgttacattc gggcagcagc ggatgatcct ccagtatggt  33960
agcgcgggtt tctgtctcaa aaggaggtag acgatcccta ctgtacggag tgcgccgaga  34020
caaccgagat cgtgttggtc gtagtgtcat gccaaatgga acgccggacg tagtcatatt  34080
tcctgaagca aaaccaggtg cgggcgtgac aaacagatct gcgtctccgg tctcgccgct  34140
tagatcgctc tgtgtagtag ttgtagtata tccactctct caaagcatcc aggcgccccc  34200
tggcttcggg ttctatgtaa actccttcat gcgccgctgc cctgataaca tccaccaccg  34260
cagaataagc cacacccagc caacctacac attcgttctg cgagtcacac acgggaggag  34320
cgggaagagc tggaagaacc atgttttttt ttttattcca aaagattatc caaaacctca  34380
aaatgaagat ctattaagtg aacgcgctcc cctccggtgg cgtggtcaaa ctctacagcc  34440
aaagaacaga taatggcatt tgtaagatgt tgcacaatgg cttccaaaag gcaaacggcc  34500
ctcacgtcca agtggacgta aaggctaaac ccttcagggt gaatctcctc tataaacatt  34560
ccagcacctt caaccatgcc caaataattc tcatctcgcc accttctcaa tatatctcta  34620
agcaaatccc gaatattaag tccggccatt gtaaaaatct gctccagagc gccctccacc  34680
ttcagcctca agcagcgaat catgattgca aaaattcagg ttcctcacag acctgtataa  34740
gattcaaaag cggaacatta acaaaaatac cgcgatcccg taggtccctt cgcagggcca  34800
gctgaacata atcgtgcagg tctgcacgga ccagcgcggc cacttccccg ccaggaacca  34860
tgacaaaaga acccacactg attatgacac gcatactcgg agctatgcta accagcgtag  34920
ccccgatgta agcttgttgc atgggcggcg atataaaatg caaggtgctg ctcaaaaaat  34980
caggcaaagc ctcgcgcaaa aaagaaagca catcgtagtc atgctcatgc agataaaggc  35040
aggtaagctc cggaaccacc acagaaaaag acaccatttt tctctcaaac atgtctgcgg  35100
gtttctgcat aaacacaaaa taaaataaca aaaaaacatt taaacattag aagcctgtct  35160
tacaacagga aaaacaaccc ttataagcat aagacggact acggccatgc cggcgtgacc  35220
gtaaaaaaac tggtcaccgt gattaaaaag caccaccgac agctcctcgg tcatgtccgg  35280
agtcataatg taagactcgg taaacacatc aggttgattc acatcggtca gtgctaaaaa  35340
gcgaccgaaa tagcccgggg gaatacatac ccgcaggcgt agagacaaca ttacagcccc  35400
cataggaggt ataacaaaat taataggaga gaaaaacaca taaacacctg aaaaaccctc  35460
ctgcctaggc aaaatagcac cctcccgctc cagaacaaca tacagcgctt ccacagcggc  35520
agccataaca gtcagcctta ccagtaaaaa agaaaaccta ttaaaaaaac accactcgac  35580
```

-continued

```
acggcaccag ctcaatcagt cacagtgtaa aaaagggcca agtgcagagc gagtatatat    35640

aggactaaaa aatgacgtaa cggttaaagt ccacaaaaaa cacccagaaa accgcacgcg    35700

aacctacgcc cagaaacgaa agccaaaaaa cccacaactt cctcaaatcg tcacttccgt    35760

tttcccacgt tacgtaactt cccattttaa gaaaactaca attcccaaca catacaagtt    35820

actccgccct aaaacctacg tcacccgccc cgttcccacg ccccgcgcca cgtcacaaac    35880

tccaccccct cattatcata ttggcttcaa tccaaaataa ggtatattat tgatgatg     35938
```

<210> SEQ ID NO 2
<211> LENGTH: 8
<212> TYPE: DNA
<213> ORGANISM: Adenovirus type 5

<400> SEQUENCE: 2 ctgacctc                                                                8

<210> SEQ ID NO 3
<211> LENGTH: 8
<212> TYPE: DNA
<213> ORGANISM: Adenovirus type 5

<400> SEQUENCE: 3 tcaccagg                                                                8

<210> SEQ ID NO 4
<211> LENGTH: 10
<212> TYPE: DNA
<213> ORGANISM: Artificial Sequence
<220> FEATURE:
<223> OTHER INFORMATION: Sequence resulting from TAV-255 deletion

<400> SEQUENCE: 4
ggtgttttgg                                                             10

<210> SEQ ID NO 5
<211> LENGTH: 9
<212> TYPE: DNA
<213> ORGANISM: Artificial Sequence
<220> FEATURE:
<223> OTHER INFORMATION: Sequence resulting from exemplary E1A promoter
      TATA box deletion

<400> SEQUENCE: 5 ctaggactg                                                               9

<210> SEQ ID NO 6
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be Lys or Arg

<400> SEQUENCE: 6

Arg Xaa Xaa Arg
1

<210> SEQ ID NO 7
<211> LENGTH: 4
<212> TYPE: PRT
<213> ORGANISM: Artificial Sequence
<220> FEATURE:
<223> OTHER INFORMATION: Furin cleavage site

<400> SEQUENCE: 7

Arg Ala Lys Arg
1

<210> SEQ ID NO 8
<211> LENGTH: 1622
<212> TYPE: DNA
<213> ORGANISM: Artificial Sequence
<220> FEATURE:
<223> OTHER INFORMATION: IL-12B/p40 - furin - IL-12A/p35 in modified E1b-19k region

<400> SEQUENCE: 8

```
atctgacctc gtcgacatgt gtcaccagca gttggtcatc tcttggtttt ccctggtttt     60
tctggcatct cccctcgtgg ccatatggga actgaagaaa gatgtttatg tcgtagaatt    120
ggattggtat ccggatgccc ctggagaaat ggtggtcctc acctgtgaca cccctgaaga    180
agatggtatc acctggacct tggaccagag cagtgaggtc ttaggctctg gcaaaaccct    240
gaccatccaa gtcaaagagt ttggagatgc tggccagtac acctgtcaca aaggaggcga    300
ggttctaagc cattcgctcc tgctgcttca caaaaaggaa gatggaattt ggtccactga    360
tattttaaag gaccagaaag aacccaaaaa taagaccttt ctaagatgcg aggccaagaa    420
ttattctgga cgtttcacct gctggtggct gacgacaatc agtactgatt tgacattcag    480
tgtcaaaagc agcagaggct cttctgaccc ccaaggggtg acgtgcggag ctgctacact    540
ctctgcagag agagtcagag gggacaacaa ggagtatgag tactcagtgg agtgccagga    600
ggacagtgcc tgcccagctg ctgaggagag tctgcccatt gaggtcatgg tggatgccgt    660
tcacaagctc aagtatgaaa actacaccag cagcttcttc atcagggaca tcatcaaacc    720
tgacccaccc aagaacttgc agctgaagcc attaaagaat tctcggcagg tggaggtcag    780
ctgggagtac cctgacacct ggagtactcc acattcctac ttctccctga cattctgcgt    840
tcaggtccag ggcaagagca agagagaaaa gaaagataga gtcttcacgg acaagacctc    900
agccacggtc atctgccgca aaaatgccag cattagcgtg cgggcccagg accgctacta    960
tagctcatct tggagcgaat gggcatctgt gccctgcagt cgtgctaagc gaagaaacct   1020
ccccgtggcc actccagacc caggaatgtt cccatgcctt caccactccc aaaacctgct   1080
gagggccgtc agcaacatgc tccagaaggc cagacaaact ctagaatttt acccttgcac   1140
ttctgaagag attgatcatg aagatatcac aaaagataaa accagcacag tggaggcctg   1200
tttaccattg gaattaacca agaatgagag ttgcctaaat tccagagaga cctctttcat   1260
aactaatggg agttgcctgg cctccagaaa gacctctttt atgatggccc tgtgccttag   1320
tagtatttat gaagacttga agatgtacca ggtggagttc aagaccatga atgcaaagct   1380
tctgatggat cctaagaggc agatctttct agatcaaaac atgctggcag ttattgatga   1440
gctgatgcag gccctgaatt tcaacagtga gactgtgcca caaaaatcct cccttgaaga   1500
accggatttt tataaaacta aaatcaagct ctgcatactt cttcatgctt tcagaattcg   1560
ggcagtgact attgatagag tgatgagcta tctgaatgct tcctaactcg agtcaccagg   1620
cg                                                                  1622
```

<210> SEQ ID NO 9
<211> LENGTH: 1598
<212> TYPE: DNA
<213> ORGANISM: Artificial Sequence
<220> FEATURE:
<223> OTHER INFORMATION: IL-12B/p40 - furin - IL-23A/p19 in modified
E1b-19k region

<400> SEQUENCE: 9

```
atctgacctc gtcgacatgt gtcaccagca gttggtcatc tcttggtttt ccctggtttt     60
tctggcatct cccctcgtgg ccatatggga actgaagaaa gatgtttatg tcgtagaatt    120
ggattggtat ccggatgccc ctggagaaat ggtggtcctc acctgtgaca cccctgaaga    180
agatggtatc acctggacct tggaccagag cagtgaggtc ttaggctctg gcaaaaccct    240
gaccatccaa gtcaaagagt ttggagatgc tggccagtac acctgtcaca aaggaggcga    300
ggttctaagc cattcgctcc tgctgcttca caaaaaggaa gatggaattt ggtccactga    360
tattttaaag gaccagaaag aacccaaaaa taagaccttt ctaagatgcg aggccaagaa    420
ttattctgga cgtttcacct gctggtggct gacgacaatc agtactgatt tgacattcag    480
tgtcaaaagc agcagaggct cttctgaccc ccaaggggtg acgtgcggag ctgctacact    540
ctctgcagag agagtcagag gggacaacaa ggagtatgag tactcagtgg agtgccagga    600
ggacagtgcc tgcccagctg ctgaggagag tctgcccatt gaggtcatgg tggatgccgt    660
tcacaagctc aagtatgaaa actacaccag cagcttcttc atcagggaca tcatcaaacc    720
tgacccaccc aagaacttgc agctgaagcc attaaagaat tctcggcagg tggaggtcag    780
ctgggagtac cctgacacct ggagtactcc acattcctac ttctccctga cattctgcgt    840
tcaggtccag ggcaagagca agagagaaaa gaaagataga gtcttcacgg acaagacctc    900
agccacggtc atctgccgca aaaatgccag cattagcgtg cgggcccagg accgctacta    960
tagctcatct tggagcgaat gggcatctgt gccctgcagt cgtgctaagc gaatgctggg   1020
gagcagagct gtaatgctgc tgttgctgct gccctggaca gctcagggca gagctgtgcc   1080
tgggggcagc agccctgcct ggactcagtg ccagcagctt tcacagaagc tctgcacact   1140
ggcctggagt gcacatccac tagtgggaca catggatcta agagaagagg gagatgaaga   1200
gactacaaat gatgttcccc atatccagtg tggagatggc tgtgaccccc aaggactcag   1260
ggacaacagt cagttctgct tgcaaaggat ccaccagggt ctgatttttt atgagaagct   1320
gctaggatcg gatattttca caggggagcc ttctctgctc cctgatagcc ctgtgggcca   1380
gcttcatgcc tccctactgg gcctcagcca actcctgcag cctgagggtc accactggga   1440
gactcagcag attccaagcc tcagtcccag ccagccatgg cagcgtctcc ttctccgctt   1500
caaaatcctt cgcagcctcc aggcctttgt ggctgtagcc gcccgggtct ttgcccatgg   1560
agcagcaacc ctgagtccct aactcgagtc accaggcg                           1598
```

<210> SEQ ID NO 10
<211> LENGTH: 46
<212> TYPE: DNA
<213> ORGANISM: Artificial Sequence
<220> FEATURE:
<223> OTHER INFORMATION: Exempalry modified E1b-19k region

<400> SEQUENCE: 10

```
atcttggtta catctgacct cgtcgagtca ccaggcgctt ttccaa                     46
```

<210> SEQ ID NO 11

<211> LENGTH: 2340
<212> TYPE: DNA
<213> ORGANISM: Artificial Sequence
<220> FEATURE:
<223> OTHER INFORMATION: IL-12B/p40 - IRES- IL-12A/p35 in modified
E1b-19k region

<400> SEQUENCE: 11

```
atctgacctc gtcgacatgt ggccccctgg gtcagcctcc cagccaccgc cctcacctgc     60
cgcggccaca ggtctgcatc cagcggctcg ccctgtgtcc ctgcagtgcc ggctcagcat    120
gtgtccagcg cgcagcctcc tccttgtggc taccctggtc ctcctggacc acctcagttt    180
ggccagaaac ctccccgtgg ccactccaga cccaggaatg ttcccatgcc ttcaccactc    240
ccaaaacctg ctgagggccg tcagcaacat gctccagaag gccagacaaa ctctagaatt    300
ttacccttgc acttctgaag agattgatca tgaagatatc acaaaagata aaaccagcac    360
agtggaggcc tgtttaccat tggaattaac caagaatgag agttgcctaa attccagaga    420
gacctctttc ataactaatg ggagttgcct ggcctccaga aagacctctt ttatgatggc    480
cctgtgcctt agtagtattt atgaagactt gaagatgtac caggtggagt tcaagaccat    540
gaatgcaaag cttctgatgg atcctaagag gcagatcttt ctagatcaaa acatgctggc    600
agttattgat gagctgatgc aggccctgaa tttcaacagt gagactgtgc cacaaaaatc    660
ctcccttgaa gaaccggatt tttataaaac taaaatcaag ctctgcatac ttcttcatgc    720
tttcagaatt cgggcagtga ctattgatag agtgatgagc tatctgaatg cttcctaata    780
ataacgttac tggccgaagc cgcttggaat aaggccggtg tgcgtttgtc tatatgttat    840
tttccaccat attgccgtct tttggcaatg tgagggcccg gaaacctggc cctgtcttct    900
tgacgagcat tcctaggggt ctttcccctc tcgccaaagg aatgcaaggt ctgttgaatg    960
tcgtgaagga agcagttcct ctggaagctt cttgaagaca aacaacgtct gtagcgaccc   1020
tttgcaggca gcggaacccc ccacctggcg acaggtgcct ctgcggccaa aagccacgtg   1080
tataagatac acctgcaaag gcggcacaac cccagtgcca cgttgtgagt tggatagttg   1140
tggaaagagt caaatggctc tcctcaagcg tattcaacaa ggggctgaag gatgcccaga   1200
aggtacccca ttgtatggga tctgatctgg ggcctcggtg cacatgcttt acatgtgttt   1260
agtcgaggtt aaaaaaacgtc taggccccccc gaaccacggg gacgtggttt tcctttgaaa   1320
aacacgatga taatatgtgt caccagcagt tggtcatctc ttggttttcc ctggtttttc   1380
tggcatctcc cctcgtggcc atatgggaac tgaagaaaga tgtttatgtc gtagaattgg   1440
attggtatcc ggatgcccct ggagaaatgg tggtcctcac ctgtgacacc cctgaagaag   1500
atggtatcac ctggaccttg gaccagagca gtgaggtctt aggctctggc aaaaccctga   1560
ccatccaagt caaagagttt ggagatgctg gccagtacac ctgtcacaaa ggaggcgagg   1620
ttctaagcca ttcgctcctg ctgcttcaca aaaaggaaga tggaatttgg tccactgata   1680
ttttaaagga ccagaaagaa cccaaaaata agacctttct aagatgcgag gccaagaatt   1740
attctggacg tttcacctgc tggtggctga cgacaatcag tactgatttg acattcagtg   1800
tcaaaagcag cagaggctct tctgaccccc aaggggtgac gtgcggagct gctacactct   1860
ctgcagagag agtcagaggg gacaacaagg agtatgagta ctcagtggag tgccaggagg   1920
acagtgcctg cccagctgct gaggagagtc tgcccattga ggtcatggtg gatgccgttc   1980
acaagctcaa gtatgaaaac tacaccagca gcttcttcat cagggacatc atcaaacctg   2040
acccacccaa gaacttgcag ctgaagccat taaagaattc tcggcaggtg gaggtcagct   2100
```

-continued

```
gggagtaccc tgacacctgg agtactccac attcctactt ctccctgaca ttctgcgttc   2160

aggtccaggg caagagcaag agagaaaaga aagatagagt cttcacggac aagacctcag   2220

ccacggtcat ctgccgcaaa aatgccagca ttagcgtgcg ggcccaggac cgctactata   2280

gctcatcttg gagcgaatgg gcatctgtgc cctgcagtta gtaactcgag tcaccaggcg   2340
```

<210> SEQ ID NO 12
<211> LENGTH: 1667
<212> TYPE: DNA
<213> ORGANISM: Artificial Sequence
<220> FEATURE:
<223> OTHER INFORMATION: IL-12B/p40 - 2A - IL-12A/p35 in modified E1b-19k region

<400> SEQUENCE: 12

```
atctgacctc gtcgacatgt gtcaccagca gttggtcatc tcttggtttt ccctggtttt     60

tctggcatct cccctcgtgg ccatatggga actgaagaaa gatgtttatg tcgtagaatt    120

ggattggtat ccggatgccc ctggagaaat ggtggtcctc acctgtgaca cccctgaaga    180

agatggtatc acctggacct tggaccagag cagtgaggtc ttaggctctg gcaaaaccct    240

gaccatccaa gtcaaagagt ttggagatgc tggccagtac acctgtcaca aaggaggcga    300

ggttctaagc cattcgctcc tgctgcttca caaaaaggaa gatggaattt ggtccactga    360

tattttaaag gaccagaaag aacccaaaaa taagaccttt ctaagatgcg aggccaagaa    420

ttattctgga cgtttcacct gctggtggct gacgacaatc agtactgatt tgacattcag    480

tgtcaaaagc agcagaggct cttctgaccc ccaaggggtg acgtgcggag ctgctacact    540

ctctgcagag agagtcagag gggacaacaa ggagtatgag tactcagtgg agtgccagga    600

ggacagtgcc tgcccagctg ctgaggagag tctgcccatt gaggtcatgg tggatgccgt    660

tcacaagctc aagtatgaaa actacaccag cagcttcttc atcagggaca tcatcaaacc    720

tgacccaccc aagaacttgc agctgaagcc attaaagaat tctcggcagg tggaggtcag    780

ctgggagtac cctgacacct ggagtactcc acattcctac ttctccctga cattctgcgt    840

tcaggtccag ggcaagagca agagagaaaa gaaagataga gtcttcacgg acaagacctc    900

agccacggtc atctgccgca aaaatgccag cattagcgtg cgggcccagg accgctacta    960

tagctcatct tggagcgaat gggcatctgt gccctgcagt cttctgaact tcgacctcct   1020

caagttggcg ggagacgttg agtccaaccc cgggcccaga aacctccccg tggccactcc   1080

agacccagga atgttcccat gccttcacca ctcccaaaac ctgctgaggg ccgtcagcaa   1140

catgctccag aaggccagac aaactctaga attttaccct tgcacttctg aagagattga   1200

tcatgaagat atcacaaaag ataaaaccag cacagtggag gcctgtttac cattggaatt   1260

aaccaagaat gagagttgcc taaattccag agagacctct ttcataacta atgggagttg   1320

cctggcctcc agaaagacct cttttatgat ggccctgtgc cttagtagta tttatgaaga   1380

cttgaagatg taccaggtgg agttcaagac catgaatgca aagcttctga tggatcctaa   1440

gaggcagatc tttctagatc aaaacatgct ggcagttatt gatgagctga tgcaggccct   1500

gaatttcaac agtgagactg tgccacaaaa atcctccctt gaagaaccgg atttttataa   1560

aactaaaatc aagctctgca tacttcttca tgctttcaga attcgggcag tgactattga   1620

tagagtgatg agctatctga atgcttccta actcgagtca ccaggcg                 1667
```

<210> SEQ ID NO 13
<211> LENGTH: 50
<212> TYPE: DNA

<213> ORGANISM: Artificial Sequence
<220> FEATURE:
<223> OTHER INFORMATION: Exempalry modified E3 region

<400> SEQUENCE: 13
tcttttctct tacagtatga taataaaaaa aaataataaa gcatcactta 50

<210> SEQ ID NO 14
<211> LENGTH: 1022
<212> TYPE: DNA
<213> ORGANISM: Artificial Sequence
<220> FEATURE:
<223> OTHER INFORMATION: IL-12B/p40 in modified E1b-19k region

<400> SEQUENCE: 14
atctgacctc gtcgacatgt gtcaccagca gttggtcatc tcttggtttt ccctggtttt 60
tctggcatct cccctcgtgg ccatatggga actgaagaaa gatgtttatg tcgtagaatt 120
ggattggtat ccggatgccc ctggagaaat ggtggtcctc acctgtgaca cccctgaaga 180
agatggtatc acctggacct tggaccagag cagtgaggtc ttaggctctg gcaaaaccct 240
gaccatccaa gtcaaagagt ttggagatgc tggccagtac acctgtcaca aaggaggcga 300
ggttctaagc cattcgctcc tgctgcttca caaaaaggaa gatggaattt ggtccactga 360
tattttaaag gaccagaaag aacccaaaaa taagaccttt ctaagatgcg aggccaagaa 420
ttattctgga cgtttcacct gctggtggct gacgacaatc agtactgatt tgacattcag 480
tgtcaaaagc agcagaggct cttctgaccc ccaaggggtg acgtgcggag ctgctacact 540
ctctgcagag agagtcagag gggacaacaa ggagtatgag tactcagtgg agtgccagga 600
ggacagtgcc tgcccagctg ctgaggagag tctgcccatt gaggtcatgg tggatgccgt 660
tcacaagctc aagtatgaaa actacaccag cagcttcttc atcagggaca tcatcaaacc 720
tgacccaccc aagaacttgc agctgaagcc attaaagaat tctcggcagg tggaggtcag 780
ctgggagtac cctgacacct ggagtactcc acattcctac ttctccctga cattctgcgt 840
tcaggtccag ggcaagagca agagagaaaa gaaagataga gtcttcacgg acaagacctc 900
agccacggtc atctgccgca aaaatgccag cattagcgtg cgggcccagg accgctacta 960
tagctcatct tggagcgaat gggcatctgt gccctgcagt tagtaactcg agtcaccagg 1020
cg 1022

<210> SEQ ID NO 15
<211> LENGTH: 834
<212> TYPE: DNA
<213> ORGANISM: Artificial Sequence
<220> FEATURE:
<223> OTHER INFORMATION: IL-12A/p35 in modified E3 region

<400> SEQUENCE: 15
atgttctttt ctcttacagt atgattaaat gagacatgtg gccccctggg tctgcctccc 60
aaccaccgcc ctcacctgcc gcggccactg gtctgcatcc tgcggctcgc cctgtgtccc 120
tgcaatgccg gctctccatg tgtcctgcgc gctccctcct ccttgtggct accctggtcc 180
tcctggacca cctctctttg gcccgaaacc tccccgtggc cactcctgac cctggaatgt 240
tcccatgcct tcaccactcc caaaacctgc tgcgggccgt ctccaacatg ctccaaaaag 300
cccgacaaac tcttgaattt tacccttgca cttctgaaga aattgatcat gaagatatca 360
caaaagataa aacctccact gtggaagcct gtttaccatt ggaattaacc aaaaatgaat 420
cttgcctaaa ttcccgagaa acctctttca taactaatgg gtcttgcctg gcctcccgaa 480
aaacctcttt tatgatggcc ctgtgccttt cttctattta tgaagacttg aaaatgtacc 540
aagtggaatt caaaaccatg aatgcaaaac ttctgatgga tcctaaacgg caaatctttc 600
ttgatcaaaa catgctggct gttattgatg aactgatgca agccctgaat ttcaactctg 660
aaactgtgcc acaaaaatcc tcccttgaag aaccggattt ttataaaact aaaatcaaac 720
tctgcatact tcttcatgct ttccgaattc gggctgtgac tattgatcga gtgatgtcct 780
atctgaatgc ttcctaatga ggtctcaaag atcttattcc ctttaactaa taaa 834

<210> SEQ ID NO 16
<211> LENGTH: 8
<212> TYPE: DNA
<213> ORGANISM: Artificial Sequence
<220> FEATURE:
<223> OTHER INFORMATION: Sequence resulting from exemplary E1A promoter
TATA box deletion

<400> SEQUENCE: 16 agtgcccg 8

<210> SEQ ID NO 17
<211> LENGTH: 8
<212> TYPE: DNA
<213> ORGANISM: Artificial Sequence
<220> FEATURE:
<223> OTHER INFORMATION: Sequence resulting from exemplary E1A promoter
TATA box deletion

<400> SEQUENCE: 17 tattcccg 8

<210> SEQ ID NO 18
<211> LENGTH: 10
<212> TYPE: DNA
<213> ORGANISM: Artificial Sequence
<220> FEATURE:
<223> OTHER INFORMATION: Sequence resulting from exemplary E1A promoter
CAAT box deletion

<400> SEQUENCE: 18
ttccgtggcg 10

<210> SEQ ID NO 19
<211> LENGTH: 8
<212> TYPE: DNA
<213> ORGANISM: Adenovirus type 5

<400> SEQUENCE: 19 cagtatga 8

<210> SEQ ID NO 20
<211> LENGTH: 10
<212> TYPE: DNA
<213> ORGANISM: Adenovirus type 5

<400> SEQUENCE: 20
taataaaaaa 10

<210> SEQ ID NO 21
<211> LENGTH: 8
<212> TYPE: DNA
<213> ORGANISM: Adenovirus type 5

<400> SEQUENCE: 21

-continued tgccttaa 8

<210> SEQ ID NO 22
<211> LENGTH: 11
<212> TYPE: DNA
<213> ORGANISM: Adenovirus type 5

<400> SEQUENCE: 22
taaaaaaaaa t 11

<210> SEQ ID NO 23
<211> LENGTH: 2242
<212> TYPE: DNA
<213> ORGANISM: Artificial Sequence
<220> FEATURE:
<223> OTHER INFORMATION: mouse IL-12A - IRES - mouse IL-12B in modified E1b-19k region

<400> SEQUENCE: 23
ctgacctcgt cgacatgtgt caatcacgct acctcctctt tttggccacc cttgccctcc 60
taaaccacct cagtttggcc agagtgatcc ctgtgtccgg ccctgccaga tgcctgagcc 120
agagcagaaa cctgctgaaa accaccgacg acatggtgaa aaccgccaga gagaagctga 180
agcactacag ctgcacagcc gaggacatcg accacgagga catcacccgg gaccagacct 240
ccaccctgaa aacctgcctg cccctggaac tgcataagaa cgagagctgc ctggccaccc 300
gcgagacaag cagcaccacc agaggcagct gtctgccccc ccagaaaacc agcctgatga 360
tgaccctgtg cctgggcagc atctacgagg acctgaagat gtaccagacc gagttccagg 420
ccatcaacgc cgccctgcag aaccacaacc accagcagat catcctggac aagggcatgc 480
tggtggccat cgacgagctg atgcagagcc tgaaccacaa cggcgaaacc ctgagacaga 540 aacccccgt gggcgaggcc gacccctaca gagtgaagat gaagctgtgc atcctgctgc 600
acgccttcag caccagagtg gtgacaatca acagagtgat gggctacctg agcagcgcct 660
gataacgtta ctggccgaag ccgcttggaa taaggccggt gtgcgtttgt ctatatgtta 720
ttttccacca tattgccgtc ttttggcaat gtgagggccc ggaaacctgg ccctgtcttc 780
ttgacgagca ttcctagggg tctttcccct ctcgccaaag gaatgcaagg tctgttgaat 840
gtcgtgaagg aagcagttcc tctggaagct tcttgaagac aaacaacgtc tgtagcgacc 900
ctttgcaggc agcggaaccc cccacctggc gacaggtgcc tctgcggcca aaagccacgt 960
gtataagata cacctgcaaa ggcggcacaa ccccagtgcc acgttgtgag ttggatagtt 1020
gtggaaagag tcaaatggct ctcctcaagc gtattcaaca aggggctgaa ggatgcccag 1080
aaggtacccc attgtatggg atctgatctg gggcctcggt gcacatgctt tacatgtgtt 1140
tagtcgaggt taaaaaacgt ctaggccccc cgaaccacgg ggacgtggtt ttcctttgaa 1200
aaacacgatg ataatatgtg cccccagaag ctgaccatca gttggttcgc catcgtgctg 1260
ctggtgtccc ccctgatggc catgtgggag ctggaaaagg acgtgtacgt ggtggaagtg 1320
gactggaccc ccgacgcccc tggcgagaca gtgaacctga cctgcgacac ccccgaagag 1380
gacgacatca cctggaccag cgaccagaga cacggcgtga tcggcagcgg caagaccctg 1440
acaatcaccg tgaaagagtt tctggacgcc ggccagtaca cctgtcacaa gggcggcgag 1500
acactgagcc actcccatct gctgctgcac aagaaagaga acggcatctg gtccaccgag 1560
atcctgaaga acttcaagaa caagaccttc ctgaagtgcg aggcccccaa ctacagcggc 1620
agattcacct gtagctggct ggtgcagaga aacatggacc tgaagttcaa catcaagagc 1680
agcagcagct cccccgacag cagagccgtg acctgtggca tggccagcct gagcgccgag 1740
aaagtgaccc tggaccagag agactacgag aagtacagcg tgtcctgcca ggaagatgtc 1800
acctgcccca ccgccgagga aaccctgcct atcgagctgg ccctggaagc cagacagcag 1860
aacaaatacg agaactactc taccagcttc ttcatccggg acatcatcaa gcccgacccc 1920
cccaagaacc tgcagatgaa gcccctgaag aacagccagg tggaagtgtc ctgggagtac 1980
cccgacagct ggtccacccc ccacagctac ttcagcctga agttcttcgt gcggatccag 2040
cgcaagaaag aaaagatgaa ggaaaccgag gaaggctgca accagaaagg cgctttcctg 2100
gtggaaaaga ccagcaccga ggtgcagtgc aagggcggca acgtgtgcgt gcaggcccag 2160
gaccggtact acaacagcag ctgcagcaag tgggcctgcg tgccctgtag agtgcgctct 2220
tgactcgagt caccaggcgc tt 2242

<210> SEQ ID NO 24
<211> LENGTH: 1631
<212> TYPE: DNA
<213> ORGANISM: Artificial Sequence
<220> FEATURE:
<223> OTHER INFORMATION: mouse IL-12B - furin - mouse IL-12A in modified E1b-19k region

<400> SEQUENCE: 24
atctgacctc gtcgacatgt gtcctcagaa gctaaccatc tcctggtttg ccatcgtttt 60
gctggtgtct ccactcatgg ccatgtggga gctggagaaa gacgtttatg ttgtagaggt 120
ggactggact cccgatgccc ctggagaaac agtgaacctc acctgtgaca cgcctgaaga 180
agatgacatc acctggacct cagaccagag acatggagtc ataggctctg gaaagaccct 240
gaccatcact gtcaaagagt ttctagatgc tggccagtac acctgccaca aaggaggcga 300
gactctgagc cactcacatc tgctgctcca caagaaggaa aatggaattt ggtccactga 360
aattttaaaa aatttcaaaa acaagacttt cctgaagtgt gaagcaccaa attactccgg 420
acggttcacg tgctcatggc tggtgcaaag aaacatggac ttgaagttca acatcaagag 480
cagtagcagt tcccctgact ctcgggcagt gacatgtgga atggcgtctc tgtctgcaga 540
gaaggtcaca ctggaccaaa gggactatga gaagtattca gtgtcctgcc aggaggatgt 600
cacctgccca actgccgagg agaccctgcc cattgaactg gcgttggaag cacggcagca 660
gaataaatat gagaactaca gcaccagctt cttcatcagg gacatcatca aaccagaccc 720
gcccaagaac ttgcagatga agcctttgaa gaactcacag gtggaggtca gctgggagta 780
ccctgactcc tggagcactc cccattccta cttctccctc aagttctttg ttcgaatcca 840
gcgcaagaaa gaaaagatga aggagacaga ggaggggtgt aaccagaaag gtgcgttcct 900
cgtagagaag acatctaccg aagtccaatg caaaggcggg aatgtctgcg tgcaagctca 960
ggatcgctat tacaattcct catgcagcaa gtgggcatgt gttccctgca gggtccgatc 1020
ccgtgctaag cgaagggtca ttccagtctc tggacctgcc aggtgtctta gccagtcccg 1080
aaacctgctg aagaccacag atgacatggt gaagacggcc agagaaaaac tgaaacatta 1140
ttcctgcact gctgaagaca tcgatcatga agacatcaca cgggaccaaa ccagcacatt 1200
gaagacctgt ttaccactgg aactacacaa gaacgagagt tgcctggcta ctagagagac 1260
ttcttccaca acaagaggga gctgcctgcc cccacagaag acgtctttga tgatgaccct 1320
gtgccttggt agcatctatg aggacttgaa gatgtaccag acagagttcc aggccatcaa 1380
cgcagcactt cagaatcaca accatcagca gatcattcta gacaagggca tgctggtggc 1440
catcgatgag ctgatgcagt ctctgaatca taatggcgag actctgcgcc agaaacctcc 1500
tgtgggagaa gcagaccctt acagagtgaa aatgaagctc tgcatcctgc ttcacgcctt 1560
cagcacccgc gtcgtgacca tcaacagggt gatgggctat ctgagctccg cctgactcga 1620
gtcaccaggc g 1631

<210> SEQ ID NO 25
<211> LENGTH: 1577
<212> TYPE: DNA
<213> ORGANISM: Artificial Sequence
<220> FEATURE:
<223> OTHER INFORMATION: mouse IL-12B - furin - mouse IL-23A in modified E1b-19k region

<400> SEQUENCE: 25
atctgacctc gtcgacatgt gtcctcagaa gctaaccatc tcctggtttg ccatcgtttt 60
gctggtgtct ccactcatgg ccatgtggga gctggagaaa gacgtttatg ttgtagaggt 120
ggactggact cccgatgccc ctggagaaac agtgaacctc acctgtgaca cgcctgaaga 180
agatgacatc acctggacct cagaccagag acatggagtc ataggctctg gaaagaccct 240
gaccatcact gtcaaagagt ttctagatgc tggccagtac acctgccaca aaggaggcga 300
gactctgagc cactcacatc tgctgctcca caagaaggaa aatggaattt ggtccactga 360
aattttaaaa aatttcaaaa acaagacttt cctgaagtgt gaagcaccaa attactccgg 420
acggttcacg tgctcatggc tggtgcaaag aaacatggac ttgaagttca acatcaagag 480
cagtagcagt tcccctgact ctcgggcagt gacatgtgga atggcgtctc tgtctgcaga 540
gaaggtcaca ctggaccaaa gggactatga gaagtattca gtgtcctgcc aggaggatgt 600
cacctgccca actgccgagg agaccctgcc cattgaactg gcgttggaag cacggcagca 660
gaataaatat gagaactaca gcaccagctt cttcatcagg gacatcatca aaccagaccc 720
gcccaagaac ttgcagatga agcctttgaa gaactcacag gtggaggtca gctgggagta 780
ccctgactcc tggagcactc cccattccta cttctccctc aagttctttg ttcgaatcca 840
gcgcaagaaa gaaaagatga aggagacaga ggaggggtgt aaccagaaag gtgcgttcct 900
cgtagagaag acatctaccg aagtccaatg caaaggcggg aatgtctgcg tgcaagctca 960
ggatcgctat tacaattcct catgcagcaa gtgggcatgt gttccctgca gggtccgatc 1020
ccgtgctaag cgagtgccta ggagtagcag tcctgactgg gctcagtgcc agcagctctc 1080
tcggaatctc tgcatgctag cctggaacgc acatgcacca gcgggacata tgaatctact 1140
aagagaagaa gaggatgaag agactaaaaa taatgtgccc cgtatccagt gtgaagatgg 1200
ttgtgaccca caaggactca aggacaacag ccagttctgc ttgcaaagga tccgccaagg 1260
tctggctttt tataagcacc tgcttgactc tgacatcttc aaaggggagc ctgctctact 1320
ccctgatagc cccatggagc aacttcacac ctccctacta ggactcagcc aactcctcca 1380
gccagaggat cacccccggg agacccaaca gatgcccagc ctgagttcta gtcagcagtg 1440
gcagcgcccc cttctccgtt ccaagatcct tcgaagcctc caggcctttt tggccatagc 1500
tgcccgggtc tttgcccacg gagcagcaac tctgactgag cccttagtgc caacagctta 1560
actcgagtca ccaggcg 1577

<210> SEQ ID NO 26
<211> LENGTH: 1349
<212> TYPE: DNA
<213> ORGANISM: Artificial Sequence -continued

```
<220> FEATURE:
<223> OTHER INFORMATION: mouse IL-27B - furin - mouse IL-27A in modified
      E1b-19k region

<400> SEQUENCE: 26

atctgacctc gtcgacatgt ccaagctgct cttcctgtca cttgccctct gggccagccg     60

ctcccctggt tacactgaaa cagctctcgt ggctctaagc cagcccagag tgcaatgcca    120

tgcttctcgg tatcccgtgg ccgtggactg ctcctggact cctctccagg ctcccaactc    180

caccagatcc acgtccttca ttgccactta caggctcggt gtggccaccc agcagcagag    240

ccagccctgc ctacaacgga gcccccaggc ctcccgatgc accatccccg acgtgcacct    300

gttctccacg gtgccctaca tgctaaatgt cactgcagtg cacccaggcg gcgccagcag    360

cagcctccta gcctttgtgg ctgagcgaat catcaagccg gaccctccgg aaggcgtgcg    420

cctgcgcaca gcgggacagc gcctgcaggt gctctggcat ccccctgctt cctggccctt    480

cccggacatc ttctctctca agtaccgact ccgctaccgg cgccgaggag cctctcactt    540

ccgccaggtg ggacccattg aagccacgac tttcaccctc aggaactcga aaccccatgc    600

caagtattgc atccaggtgt cagctcagga cctcacagat tatgggaaac caagtgactg    660

gagcctccct gggcaagtag aaagtgcacc ccataagccc cgtgctaagc gattcccaac    720

agacccccctg agccttcaag agctgcgcag ggaattcaca gtcagcctgt accttgccag    780

gaagctgctc tctgaggttc agggctatgt ccacagcttt gctgaatctc gattgccagg    840

agtgaacctg gacctcctgc ccctgggata ccatcttccc aatgtttccc tgactttcca    900

ggcatggcat cacctctctg actctgagag actctgcttc ctcgctacca cacttcggcc    960

cttccctgcc atgctgggag ggctggggac ccaggggacc tggaccagct cagagaggga   1020

gcagctgtgg gccatgaggc tggatctccg ggacctgcac aggcacctcc gctttcaggt   1080

gctggctgca ggattcaaat gttcaaagga agaggaagac aaggaggaag aggaagagga   1140

ggaagaagaa gaaaagaagc tgcccctagg ggctctgggt ggccccaatc aggtgtcatc   1200

ccaagtgtcc tggccccagc tgctctatac ctaccagctc cttcactccc tggagcttgt   1260

cctgtctcgg gctgttcggg acctgctgct gctgtccctg cccaggcgcc caggctcagc   1320

ctgggattcc taactcgagt caccaggcg                                     1349
```

MULTIPLE TRANSGENE RECOMBINANT ADENOVIRUS

CROSS-REFERENCE TO RELATED APPLICATIONS

This application is a § 371 National Stage of International (PCT) Patent Application No. PCT/US2018/027375, filed Apr. 12, 2018, which claims the benefit of, and priority to, U.S. Provisional Patent Application No. 62/484,841 filed Apr. 12, 2017, the entire disclosures of each of which are hereby incorporated by reference herein for all purposes.

FIELD OF THE INVENTION

The field of the invention is molecular biology and virology, specifically recombinant viruses that express two or more therapeutic transgenes.

BACKGROUND

Despite extensive knowledge of the underlying molecular mechanisms that cause cancer, most advanced cancers remain incurable with current chemotherapy and radiation protocols. Oncolytic viruses have emerged as a platform technology that has the potential to significantly augment current standard treatment for a variety of malignancies (Kumar, S. et al. (2008) Current Opinion In Molecular Therapeutics 10(4):371-379; Kim, D. (2001) Expert Opinion On Biological Therapy 1(3):525-538; Kim D. (2000) Oncogene 19(56):6660-6669). These viruses have shown promise as oncolytic agents that not only directly destroy malignant cells via an infection-to-reproduction-to-lysis chain reaction but also indirectly induce anti-tumor immunity. These immune stimulatory properties have been augmented with the insertion of therapeutic transgenes that are copied and expressed each time the virus replicates.

Previously developed oncolytic viruses include the oncolytic serotype 5 adenovirus (Ad5) referred to as TAV-255 that is transcriptionally attenuated in normal cells but transcriptionally active in cancer cells (see, PCT Publication No. WO2010101921). It is believed that the mechanism by which the TAV-255 vector achieves this tumor selectivity is through targeted deletion of three transcriptional factor (TF) binding sites for the transcription factors Pea3 and E2F, proteins that regulate adenovirus expression of E1a, the earliest gene to be transcribed after virus entry into the host cell, through binding to specific DNA sequences.

Despite the efforts to date, there is a need for improved recombinant viruses, e.g., recombinant oncolytic viruses, for treating cancers and hyperproliferative disorders in human patients.

SUMMARY OF THE INVENTION

The invention is based, in part, upon the discovery that for certain recombinant adenoviruses, such as recombinant oncolytic adenoviruses, that express two therapeutic transgenes, the expression of each therapeutic transgene can be greatly enhanced when the two therapeutic transgenes are expressed as a single polypeptide chain with an intervening cleavage site, for example, a proteolytic cleavage site. The cleavage site can then be cleaved posttranslationally by one or more cleavage agents, for example, endogenous or exogenous cleavage agents, to produce the mature protein products encoded by each therapeutic transgene. Such an approach has the additional benefit of ensuring stoichiometric expression and simultaneous delivery of each therapeutic transgene.

In one aspect, the invention provides a recombinant adenovirus comprising a first nucleotide sequence encoding a first therapeutic transgene, a second nucleotide sequence encoding a second therapeutic transgene, and a third nucleotide sequence encoding a cleavage site disposed between the first nucleotide sequence and the second nucleotide sequence. In certain embodiments, the recombinant adenovirus comprises a recombinant polynucleotide sequence comprising, in a 5' to 3' orientation, the first nucleotide sequence, the third nucleotide sequence, and the second nucleotide sequence. In certain embodiments, the recombinant adenovirus comprises a recombinant polynucleotide sequence comprising, consecutively, in a 5' to 3' orientation, the first nucleotide sequence, the third nucleotide sequence, and the second nucleotide sequence, e.g. there are no intervening nucleotide sequences (for example, sequences containing another transgene or regulatory sequence) disposed between the first nucleotide sequence and the third nucleotide sequence and/or between the third nucleotide sequence and the second nucleotide sequence. In certain embodiments, the first nucleotide sequence, the third nucleotide sequence, and the second nucleotide sequence are operably linked to a single promoter (optionally positioned 5' to the first nucleotide of the first nucleotide sequence) and expressed as a single polypeptide chain.

The cleavage site may be a proteolytic cleavage site, e.g., a proteolytic cleavage site that is cleaved by a protease present in an endoplasmic reticulum or golgi of a eukaryotic cell. In certain embodiments, the proteolytic cleavage site is a furin cleavage site, e.g., a furin cleavage site comprising the sequence $RX_1X_2R$ (SEQ ID NO: 6), wherein $X_1$ is any amino acid, and $X_2$ is Lys or Arg, e.g., a furin cleavage site comprising the sequence RAKR (SEQ ID NO: 7).

In certain embodiments, the recombinant adenovirus is a type 5 adenovirus (Ad5) or a type 2 adenovirus (Ad2).

In certain embodiments, the first, second, and third nucleotide sequences are inserted into an E1b-19k insertion site located between the start site of E1b-19K and the stop site of E1b-19K. In certain embodiments, the E1b-19K insertion site is located between the start site of E1b-19K and the start site of E1b-55K. In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent the start site of E1b-19K. In certain embodiments, the E1b-19K insertion site comprises a deletion of about 200 nucleotides, e.g., 202 or 203 nucleotides adjacent the start site of E1b-19K. In certain embodiments, the E1b-19K insertion site comprises a deletion corresponding to nucleotides 1714-1917 or 1714-1916 of the Ad5 genome (SEQ ID NO: 1). In certain embodiments, the first, second, and third nucleotide sequences are inserted between nucleotides corresponding to 1714 and 1917 or between nucleotides corresponding to 1714 and 1916 of the Ad5 genome (SEQ ID NO: 1). In certain embodiments, first, second, and third nucleotide sequences are inserted between CTGACCTC (SEQ ID NO: 2) and TCACCAGG (SEQ ID NO: 3), e.g., the recombinant adenovirus comprises, in a 5' to 3' orientation, CTGACCTC (SEQ ID NO: 2), the first nucleotide sequence, the third nucleotide sequence, the second nucleotide sequence, and TCACCAGG (SEQ ID NO: 3).

In certain embodiments, the recombinant adenovirus comprises an E1a promoter having a deletion of a functional Pea3 binding site. For example, the virus may comprise a deletion of nucleotides corresponding to about −300 to about −250 upstream of the initiation site of E1a, e.g., a deletion of nucleotides corresponding to −305 to −255 or −304 to −255 upstream of the initiation site of E1a. In certain embodiments, the deletion comprises a deletion of nucleotides corresponding to 195-244 of the Ad5 genome (SEQ ID NO: 1), and/or the E1a promoter comprises the sequence GGTGTTTTGG (SEQ ID NO: 4).

In certain embodiments, the recombinant adenovirus comprises an E1a promoter having a deletion of a functional TATA box, e.g., the deletion of an entire TATA box. For example, in certain embodiments, the virus comprises a deletion of nucleotides corresponding to −27 to −24, −31 to −24, −44 to +54, or −146 to +54 of the adenovirus type 5 E1a promoter, which correspond, respectively, to nucleotides 472 to 475, 468 to 475, 455 to 552, and 353 to 552 of the Ad5 genome (SEQ ID NO: 1). In certain embodiments, the virus comprises a polynucleotide deletion that results in a virus comprising the sequence CTAGGACTG (SEQ ID NO: 5), AGTGCCCG (SEQ ID NO: 16), or TATTCCCG (SEQ ID NO: 17), which result from joining the two polynucleotide sequences that would otherwise flank the deleted polynucleotide sequence.

In certain embodiments, the recombinant adenovirus comprises a deletion of nucleotides corresponding to −29 to −26, −33 to −26, −44 to +52, or −148 to +52 of the adenovirus type 5 E1a promoter. In certain embodiments, the virus comprises a deletion of nucleotides corresponding to 353 to 552 of the Ad5 genome (SEQ ID NO: 1). In certain embodiments, the virus comprises a polynucleotide deletion that results in a virus comprising the sequence CTAGGACTG (SEQ ID NO: 5), which results from joining the two polynucleotide sequences that would otherwise flank the deleted polynucleotide sequence.

In certain embodiments, the recombinant adenovirus comprises an E1a promoter having a deletion of a functional CAAT box, e.g., the deletion of an entire CAAT box. For example, in certain embodiments, the virus comprises a deletion of nucleotides corresponding to −76 to −68 of the adenovirus type 5 E1a promoter, which corresponds to nucleotides 423 to 431 of the Ad5 genome (SEQ ID NO: 1). In certain embodiments, the virus comprises a polynucleotide deletion that results in a virus comprising the sequence TTCCGTGGCG (SEQ ID NO: 18), which results from joining the two polynucleotide sequences that would otherwise flank the deleted polynucleotide sequence.

In certain embodiments the recombinant adenovirus comprises an E3 deletion. In certain embodiments, the E3 deletion comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or from about 3000 to about 3185 nucleotides. In certain embodiments, the E3 deletion site is located between the stop site of pVIII and the start site of Fiber. In certain embodiments, the E3 deletion site is located between the stop site of E3-10.5K and the stop site of E3-14.7K. In certain embodiments, the E3 deletion comprises a deletion of from about 500 to about 1551, from about 500 to about 1500, from about 500 to about 1000, from about 1000 to about 1551, from about 1000 to about 1500, or from about 1500 to about 1551 nucleotides adjacent the stop site of E3-10.5K. In certain embodiments, the E3 deletion comprises a deletion of about 1050 nucleotides adjacent the stop site of E3-10.5K, e.g., the E3 deletion comprises a deletion of 1063 or 1064 nucleotides adjacent the stop site of E3-10.5K. In certain embodiments, the E3 deletion comprises a deletion corresponding to the Ad5 dl309 E3 deletion. In certain embodiments, the E3 deletion comprises a deletion corresponding to nucleotides 29773-30836 of the Ad5 genome (SEQ ID NO: 1).

In certain embodiments, the E3 deletion is located between stop site of E3-19K and the stop site of E3-14.7K. In certain embodiments, the E3 deletion comprises a deletion of from about 500 to about 1824, from about 500 to about 1500, from about 500 to about 1000, from about 1000 to about 1824, from about 1000 to about 1500, or from about 1500 to about 1824 nucleotides adjacent the stop site of E3-gp19K. In certain embodiments, the E3 deletion comprises a deletion of about 1600 nucleotides adjacent the stop site of E3-gp19K, e.g., the E3 deletion comprises a deletion of 1622 nucleotides adjacent the stop site of E3-19K. In certain embodiments, the E3 deletion comprises a deletion corresponding to nucleotides 29218-30839 of the Ad5 genome (SEQ ID NO: 1).

In certain embodiments, the recombinant adenovirus further comprises an E4 deletion. In certain embodiments, the E4 deletion is located between the start site of E4-ORF6/7 and the right inverted terminal repeat (ITR). In certain embodiments, the E4 deletion is located between the start site of E4-ORF6/7 and the start site of E4-ORF1. In certain embodiments, the E4 deletion comprises a deletion of from about 500 to about 2500, from about 500 to about 2000, from about 500 to about 1500, from about 500 to about 1000, from about 1000 to about 2500, from about 1000 to about 2000, from about 1000 to about 1500, from about 1500 to about 2500, from about 1500 to about 2000, or from about 2000 to about 2500 nucleotides. In certain embodiments, the E4 deletion comprises a deletion of from about 250 to about 1500, from about 250 to about 1250, from about 250 to about 1000, from about 250 to about 750, from about 250 to about 500, from 500 to about 1500, from about 500 to about 1250, from about 500 to about 1000, from about 500 to about 750, from 750 to about 1500, from about 750 to about 1250, from about 750 to about 1000, from about 1000 to about 1500, or from about 1000 to about 1250 nucleotides adjacent the start site of E4-ORF6/7. In certain embodiments, the E4 deletion comprises a deletion of about 1450 nucleotides adjacent the start site of E4-ORF6/7, e.g., the E4 deletion comprises a deletion of about 1449 nucleotides adjacent the start site of E4-ORF6/7. In certain embodiments, the E4 deletion comprises a deletion corresponding to nucleotides 34078-35526 of the Ad5 genome (SEQ ID NO: 1).

In certain embodiments, the first and/or second therapeutic transgene encodes a polypeptide selected from acetylcholine, an anti-CTLA-4 antibody heavy chain or light chain, an anti-PD-1 antibody heavy chain or light chain, an anti-PD-L1 antibody heavy chain or light, BORIS/CTCFL, CD19, CD20, CD40L, CD70, CD80, CD86, CD137, CD137L, CD154, DKK1/Wnt, FGF, GITRL, GM-CSF, ICAM, IL-1, IL-2, IL-3, IL-4, IL-5, IL-6, IL-7, IL-8, IL-9, an IL-10 trap, IL-15, an IL-15 IL-15 receptor fusion protein, IL-17, IL-23, IL-23A/p19, IL-12B/p40, IL-24, IL-27, IL-27A/p28, IL-27B/EBI3, IL-35, interferon-gamma, MAGE, NY-ESO-1, Ox40L, p53, secreted flagellin, TGF-β, a TGF-β trap, thymidine kinase, and TNF-alpha.

In certain embodiments, the first and/or second therapeutic transgene encodes a polypeptide selected from acetylcholine, an anti-CTLA-4 antibody heavy chain or light chain, an anti-PD-1 antibody heavy chain or light chain, an anti-PD-L1 antibody heavy chain or light, BORIS/CTCFL, CD19, CD20, CD40L, CD70, CD80, CD86, CD137, CD137L, CD154, DKK1/Wnt, FGF, GITRL, GM-CSF, ICAM, IL-1, IL-2, IL-3, IL-4, IL-5, IL-6, IL-7, IL-8, IL-9, an IL-10 trap, IL-12, IL-12A/p35, IL-12B/p40, IL-15, an IL-15 IL-15 receptor fusion protein, IL-23A/p19, interferon-gamma, MAGE, NY-ESO-1, Ox40L, p53, secreted flagellin, TGF-β, a TGF-β trap, thymidine kinase, and TNF-alpha.

In certain embodiments, the first and second therapeutic transgene encode a first and second subunit, respectively, of a heterodimeric protein, e.g., a heterodimeric cytokine. For example, in certain embodiments, in any of the foregoing recombinant adenoviruses, the first and/or second therapeutic transgenes are selected from IL-12A/p35 and IL-12B/p40, e.g., the first therapeutic transgene encodes IL-12B/p40 and the second therapeutic transgene encodes IL-12A/p35. In certain embodiments, the recombinant adenovirus comprises a nucleotide sequence encoding an amino acid sequence that is encoded by nucleotides 17-1000 of SEQ ID NO: 8, nucleotides 1013-1606 of SEQ ID NO: 8, and/or nucleotides 17-1606 of SEQ ID NO: 8. In certain embodiments, the recombinant adenovirus comprises the nucleotide sequence of SEQ ID NO: 8, or comprises a sequence having 80%, 85%, 86%, 87%, 88%, 89%, 90%, 91%, 92%, 93%, 94%, 95%, 96%, 97%, 98%, or 99% sequence identity to SEQ ID NO: 8.

In certain embodiments, in any of the foregoing recombinant adenoviruses, the first and/or second therapeutic transgenes are selected from IL-23A/p19 and IL-12B/p40, e.g., the first therapeutic transgene encodes IL-12B/p40 and the second therapeutic transgene encodes IL-23A/p19. In certain embodiments, the recombinant adenovirus comprises a nucleotide sequence encoding an amino acid sequence that is encoded by nucleotides 17-1000 of SEQ ID NO: 9, nucleotides 1013-1582 of SEQ ID NO: 9, and/or nucleotides 17-1582 of SEQ ID NO: 9. In certain embodiments, the recombinant adenovirus comprises the nucleotide sequence of SEQ ID NO: 9, or comprises a sequence having 80%, 85%, 86%, 87%, 88%, 89%, 90%, 91%, 92%, 93%, 94%, 95%, 96%, 97%, 98%, or 99% sequence identity to SEQ ID NO: 9.

In certain embodiments, any of the foregoing recombinant viruses may selectively replicate in a hyperproliferative cell. In certain embodiments, any of the foregoing recombinant viruses may selectively express two or more therapeutic transgenes in a hyperproliferative cell. The hyperproliferative cell may be a cancer cell, e.g., a lung cancer cell, a colon cancer cell, and a pancreatic cancer cell. In certain embodiments, any of the foregoing recombinant viruses may be an oncolytic virus.

In certain embodiments, in any of the foregoing recombinant adenoviruses, the first and/or second therapeutic transgenes are not operably linked to an exogenous promoter sequence. In certain embodiments, the size of the first and second therapeutic transgenes when combined comprises from about 500 to about 5000, from about 500 to about 4000, from about 500 to about 3000, from about 500 to about 2000, from about 500 to about 1000, from about 1000 to about 5000, from about 1000 to about 4000, from about 1000 to about 3000, from about 1000 to about 2000, from about 2000 to about 5000, from about 2000 to about 4000, from about 2000 to about 3000, from about 3000 to about 5000, from about 3000 to about 4000, or from about 4000 to 5000 nucleotides. In certain embodiments, the size of the first and second therapeutic transgenes when combined comprises from about 500 to about 7000, from about 500 to about 6000, from about 500 to about 5000, from about 500 to about 4000, from about 500 to about 3000, from about 500 to about 2000, from about 500 to about 1000, from about 1000 to about 7000, from about 1000 to about 6000, from about 1000 to about 5000, from about 1000 to about 4000, from about 1000 to about 3000, from about 1000 to about 2000, from about 2000 to about 7000, from about 2000 to about 6000, from about 2000 to about 5000, from about 2000 to about 4000, from about 2000 to about 3000, from about 3000 to about 7000, from about 3000 to about 6000, from about 3000 to about 5000, from about 3000 to about 4000, from about 4000 to about 7000, from about 4000 to about 6000, from about 4000 to about 5000 nucleotides, from about 5000 to about 7000, from about 5000 to about 6000, or from about 6000 to about 7000 nucleotides.

In certain embodiments, the size of the first and second therapeutic transgenes when combined comprises at least from about 500 to about 5000, from about 500 to about 4000, from about 500 to about 3000, from about 500 to about 2000, from about 500 to about 1000, from about 1000 to about 5000, from about 1000 to about 4000, from about 1000 to about 3000, from about 1000 to about 2000, from about 2000 to about 5000, from about 2000 to about 4000, from about 2000 to about 3000, from about 3000 to about 5000, from about 3000 to about 4000, or from about 4000 to 5000 nucleotides. In certain embodiments, the size of the first and second therapeutic transgenes when combined comprises at least from about 500 to about 7000, from about 500 to about 6000, from about 500 to about 5000, from about 500 to about 4000, from about 500 to about 3000, from about 500 to about 2000, from about 500 to about 1000, from about 1000 to about 7000, from about 1000 to about 6000, from about 1000 to about 5000, from about 1000 to about 4000, from about 1000 to about 3000, from about 1000 to about 2000, from about 2000 to about 7000, from about 2000 to about 6000, from about 2000 to about 5000, from about 2000 to about 4000, from about 2000 to about 3000, from about 3000 to about 7000, from about 3000 to about 6000, from about 3000 to about 5000, from about 3000 to about 4000, from about 4000 to about 7000, from about 4000 to about 6000, from about 4000 to about 5000 nucleotides, from about 5000 to about 7000, from about 5000 to about 6000, or from about 6000 to about 7000 nucleotides.

In certain embodiments, the size of the first and second therapeutic transgenes when combined comprises at least about 500, about 1000, about 2000, about 3000, about 4000, or about 5000 nucleotides. In certain embodiments, the size of the first and second therapeutic transgenes when combined comprises at least about 500, about 1000, about 2000, about 3000, about 4000, about 5000 nucleotides, about 6000, or about 7000 nucleotides. In certain embodiments, the size of the first and second therapeutic transgenes when combined comprises about 1600 nucleotides, about 1650 nucleotides, or about 3100 nucleotides.

In another aspect, the invention provides a pharmaceutical composition comprising each of the foregoing recombinant adenoviruses and at least one pharmaceutically acceptable carrier or diluent.

In another aspect, the invention provides a method of treating cancer in a subject. The method comprises administering to the subject an effective amount of a recombinant adenovirus described herein to treat the cancer disease in the subject. In certain embodiments, the cancer is selected from anal cancer, basal cell carcinoma, bladder cancer, bone cancer, brain cancer, breast cancer, carcinoma, cholangiocarcinoma, cervical cancer, colon cancer, colorectal cancer, endometrial cancer, gastroesophageal cancer, gastrointestinal (GI) cancer, gastrointestinal stromal tumor, hepatocellular carcinoma, gynecologic cancer, head and neck cancer, hematologic cancer, kidney cancer, leukemia, liver cancer, lung cancer, lymphoma, melanoma, merkel cell carcinoma, mesothelioma, neuroendocrine cancer, non-small cell lung cancer, ovarian cancer, pancreatic cancer, pediatric cancer, prostate cancer, renal cell carcinoma, sarcoma, skin cancer, small cell lung cancer, squamous cell carcinoma of the skin, stomach cancer, testicular cancer and thyroid cancer.

In another aspect, the invention provides a method of inhibiting proliferation of a tumor cell in a subject. The method comprises administering to the subject an effective amount of a recombinant adenovirus described herein to inhibit proliferation of the tumor cell.

In another aspect, the invention provides a method of inhibiting tumor growth in a subject. The method comprises administering to the subject an effective amount of a recombinant adenovirus described herein to inhibit proliferation of the tumor cell.

In each of the foregoing methods, the recombinant adenovirus can, e.g., be administered in combination with one or more therapies selected from surgery, radiation, chemotherapy, immunotherapy, hormone therapy, and virotherapy. In each of the foregoing methods, the effective amount of the recombinant adenovirus can be, e.g., $10^2$-$10^{15}$ plaque forming units (pfus). In certain embodiments of any of the foregoing methods, the subject can be a human, e.g., a pediatric human.

In another aspect, the invention provides a method of expressing two or more therapeutic transgenes in a target cell. The method comprises delivering to the cell, e.g., exposing the cell, to an effective amount of a recombinant adenovirus described herein to express the target transgenes. In certain embodiments, the two therapeutic transgenes, when expressed, produce a single polypeptide chain, which may be cleaved posttranslationally into two polypeptide chains.

These and other aspects and advantages of the invention are illustrated by the following figures, detailed description and claims.

DESCRIPTION OF THE DRAWINGS

The invention can be more completely understood with reference to the following drawings.

DETAILED DESCRIPTION

Figure 1:
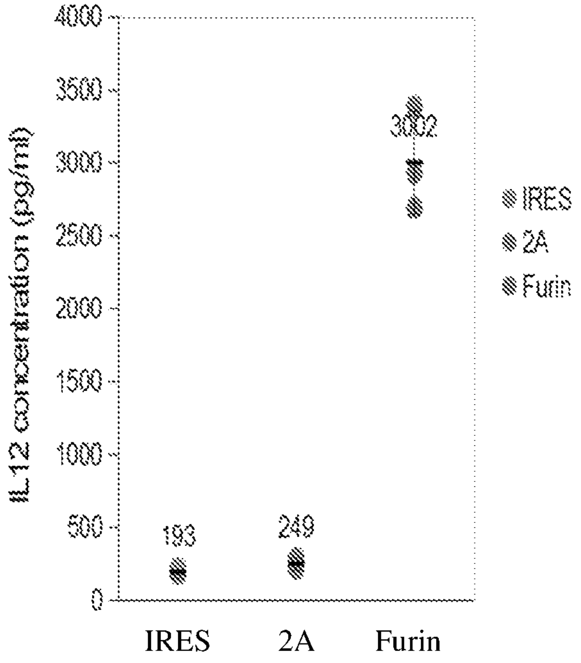
FIG. 1 is a graph depicting IL-12 expression by HEK-293 cells transiently transfected with plasmids encoding IL-12 with different linkers, as determined by ELISA. Dots represent concentrations measured in triplicates, thick bars represent mean, and error bars represent standard deviation.

The invention is based, in part, upon the discovery that for certain recombinant adenoviruses, such as recombinant oncolytic adenoviruses, that express two therapeutic transgenes, the expression of each therapeutic transgene can be greatly enhanced when the two therapeutic transgenes are expressed as a single polypeptide chain with an intervening cleavage site, for example, a proteolytic cleavage site. The cleavage site can then be cleaved posttranslationally by one or more cleavage agents, for example, endogenous or exogenous cleavage agents, to produce the mature protein products encoded by each therapeutic transgene. Such an approach has the additional benefit of ensuring stoichiometric expression and simultaneous delivery of each therapeutic transgene.

Accordingly, in one aspect, the invention provides a recombinant adenovirus comprising a first nucleotide sequence encoding a first therapeutic transgene, a second nucleotide sequence encoding a second therapeutic transgene, and a third nucleotide sequence encoding a cleavage site disposed between the first nucleotide sequence and the second nucleotide sequence. In certain embodiments, the recombinant adenovirus comprises a recombinant polynucleotide sequence comprising, in a 5' to 3' orientation, the first nucleotide sequence, the third nucleotide sequence, and the second nucleotide sequence. In certain embodiments, the recombinant adenovirus comprises a recombinant polynucleotide sequence comprising, consecutively, in a 5' to 3' orientation, the first nucleotide sequence, the third nucleotide sequence, and the second nucleotide sequence, e.g. there are no intervening nucleotide sequences (for example, sequences containing another transgene or regulatory sequence) disposed between the first nucleotide sequence and the third nucleotide sequence and/or between the third nucleotide sequence and the second nucleotide sequence. In certain embodiments, the first nucleotide sequence, the third nucleotide sequence, and the second nucleotide sequence are operably linked to a single promoter (optionally positioned 5' to the first nucleotide of the first nucleotide sequence) and expressed as a single polypeptide chain.

In certain embodiments, the recombinant adenovirus is an oncolytic virus, e.g., a virus that exhibits tumor-selective replication and/or viral mediated lysis. In certain embodiments, the oncolytic virus allows for selective expression of a therapeutic transgene, e.g., the virus permits expression of the therapeutic transgene in neoplastic cells, but attenuates expression in normal cells. In certain embodiments, the expression of the therapeutic transgene in a non-hyperproliferative cell is about 90%, about 80%, about 70%, about 60%, about 50%, about 40%, about 30%, about 20%, about 10%, or about 5% of the expression in a hyperproliferative cell. In certain embodiments, the virus exhibits no detectable expression of the therapeutic transgene in a non-hyperproliferative cell. Therapeutic transgene expression may be determined by any appropriate method known in the art, e.g., Western blot or ELISA. The hyperproliferative cell may be a cancer cell, e.g., a carcinoma, sarcoma, leukemia, lymphoma, prostate cancer, lung cancer, gastrointestinal tract cancer, colorectal cancer, pancreatic cancer, breast cancer, ovarian cancer, cervical cancer, stomach cancer, thyroid cancer, mesothelioma, liver cancer, kidney cancer, skin cancer, head and neck cancer, or brain cancer cell.

I. Viruses

The term "virus" is used herein to refer any of the obligate intracellular parasites having no protein-synthesizing or energy-generating mechanism. The viral genome may be RNA or DNA. The viruses useful in the practice of the present invention include recombinantly modified enveloped or non-enveloped DNA and RNA viruses, preferably selected from baculoviridiae, parvoviridiae, picornoviridiae, herpesviridiae, poxyiridae, or adenoviridiae. A recombinantly modified virus is referred to herein as a "recombinant virus." A recombinant virus may, e.g., be modified by recombinant DNA techniques to be replication deficient, conditionally replicating, or replication competent, and/or be modified by recombinant DNA techniques to include expression of exogenous transgenes. Chimeric viral vectors which exploit advantageous elements of each of the parent vector properties (See, e.g., Feng et al. (1997) Nature Biotechnology 15:866-870) may also be useful in the practice of the present invention. Although it is generally favored to employ a virus from the species to be treated, in some instances it may be advantageous to use vectors derived from different species that possess favorable pathogenic features. For example, equine herpes virus vectors for human gene therapy are described in PCT Publication No. WO 98/27216. The vectors are described as useful for the treatment of humans as the equine virus is not pathogenic to humans. Similarly, ovine adenoviral vectors may be used in human gene therapy as they are claimed to avoid the antibodies against the human adenoviral vectors. Such vectors are described in PCT Publication No. WO 97/06826.

Preferably, the recombinant virus is an adenovirus. Adenoviruses are medium-sized (90-100 nm), non-enveloped (naked), icosahedral viruses composed of a nucleocapsid and a double-stranded linear DNA genome. Adenoviruses replicate in the nucleus of mammalian cells using the host's replication machinery. The term "adenovirus" refers to any virus in the genus Adenoviridiae including, but not limited to, human, bovine, ovine, equine, canine, porcine, murine, and simian adenovirus subgenera. In particular, human adenoviruses includes the A-F subgenera as well as the individual serotypes thereof, the individual serotypes and A-F subgenera including but not limited to human adenovirus types 1, 2, 3, 4, 4a, 5, 6, 7, 8, 9, 10, 11 (Ad11a and Ad11p), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. Preferred are recombinant viruses derived from human adenovirus types 2 and 5. Unless stated otherwise, all adenovirus type 5 nucleotide numbers are relative to the NCBI reference sequence AC_000008.1, which is depicted herein in SEQ ID NO: 1.

The adenovirus replication cycle has two phases: an early phase, during which 4 transcription units E1, E2, E3, and E4 are expressed, and a late phase which occurs after the onset of viral DNA synthesis when late transcripts are expressed primarily from the major late promoter (MLP). The late messages encode most of the virus's structural proteins. The gene products of E1, E2 and E4 are responsible for transcriptional activation, cell transformation, viral DNA replication, as well as other viral functions, and are necessary for viral growth.

The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a gene if it affects the transcription of the gene. Operably linked nucleotide sequences are typically contiguous. However, as enhancers generally function when separated from the promoter by several kilobases and intronic sequences may be of variable lengths, some polynucleotide elements may be operably linked but not directly flanked and may even function in trans from a different allele or chromosome.

In certain embodiments, the recombinant adenovirus has one or more modifications to a regulatory sequence or promoter. A modification to a regulatory sequence or promoter comprises a deletion, substitution, or addition of one or more nucleotides compared to the wild-type sequence of the regulatory sequence or promoter.

In certain embodiments, the modification of a regulatory sequence or promoter comprises a modification of the sequence of a transcription factor binding site to reduce affinity for the transcription factor, for example, by deleting a portion thereof, or by inserting a single point mutation into the binding site. In certain embodiments, the modified regulatory sequence enhances expression in neoplastic cells and/or attenuates expression in normal cells.

In certain embodiments, the modified regulatory sequence is operably linked to a sequence encoding a protein. In certain embodiments, at least one of the adenoviral E1a and E1b genes (coding regions) is operably linked to a modified regulatory sequence. In certain embodiments, the E1a gene is operably linked to a modified regulatory sequence.

The E1a regulatory sequence contains five binding sites for the transcription factor Pea3, designated Pea3 I, Pea3 II, Pea3 III, Pea3 IV, and Pea3 V, where Pea3 I is the Pea3 binding site most proximal to the E1a start site, and Pea3 V is most distal. The E1a regulatory sequence also contains binding sites for the transcription factor E2F, hereby designated E2F I and E2F II, where E2F I is the E2F binding site most proximal to the E1a start site, and E2F II is more distal. From the E1a start site, the binding sites are arranged: Pea3 I, E2F I, Pea3 II, E2F II, Pea3 III, Pea3 IV, and Pea3 V.

In certain embodiments, at least one of these seven binding sites, or at least one of seven functional binding sites, is deleted. As used herein, a "functional binding site" refers to a binding site that is capable of binding to a respective binding partner, e.g., a transcription factor, e.g., a binding site that has at least 100%, at least 90%, at least 80%, at least 70%, at least 60%, at least 50%, or at least 40%, of the binding activity of a corresponding wild-type binding site sequence. As used herein, a "non-functional binding site" refers to a binding site that, e.g., has less than 30%, less than 20%, less than 10%, or 0% of the binding activity of a corresponding wild-type binding site sequence.

In certain embodiments, the recombinant adenovirus comprises an E1a promoter having a deletion of a functional Pea3 binding site, e.g., the deletion of an entire Pea3 binding site. As used herein, a "functional Pea3 binding site" refers to a Pea3 binding site that is capable of binding to its respective transcription factor (e.g., Pea3), e.g., a Pea3 binding site that has at least 100%, at least 90%, at least 80%, at least 70%, at least 60%, at least 50%, or at least 40%, of the Pea3 binding activity of a corresponding wild-type Pea3 binding site sequence. As used herein, a "non-functional Pea3 binding site" refers to a Pea3 binding site that, e.g., has less than 30%, less than 20%, less than 10%, or 0% of the Pea3 binding activity of a corresponding wild-type Pea3 binding site sequence. Assays for determining whether a Pea3 binding site binds to Pea3 are known in the art. Exemplary binding assays include electrophoretic mobility shift assays, chromatin immunoprecipitation assays, and DNAse footprinting assays.

In certain embodiments, at least one Pea3 binding site, or a functional Pea3 binding site, is deleted. The deleted Pea3 binding site can be Pea3 I, Pea3 II, Pea3 III, Pea3 IV, and/or Pea3 V. In certain embodiments, the deleted Pea3 binding site is Pea3 II, Pea3 III, Pea3 IV, and/or Pea3 V. In certain embodiments, the deleted Pea3 binding site is Pea3 IV and/or Pea3 V. In certain embodiments, the deleted Pea3 binding site is Pea3 II and/or Pea3 III. In certain embodiments, the deleted Pea3 binding site is both Pea3 II and Pea3 III. In certain embodiments, the Pea3 I binding site, or a functional Pea3 I binding site, is retained.

In certain embodiments, at least one E2F binding site, or a functional E2F binding site, is deleted. In certain embodiments, at least one E2F binding site, or a functional E2F binding site, is retained. In certain embodiments, the retained E2F binding site is E2F I and/or E2F II. In certain embodiments, the retained E2F binding site is E2F II. In certain embodiments, the total deletion consists essentially of one or more of Pea3 II, Pea3 III, Pea3 IV, and/or Pea3 V.

In certain embodiments, the recombinant adenovirus comprises a deletion of at least one E2F binding site, or a functional portion thereof. In certain embodiments, the recombinant adenovirus comprises a deletion of at least one E2F binding site, or a functional portion thereof, and does not comprise a deletion of a Pea3 binding site.

In certain embodiments, the virus has a deletion of a 50 base pair region located from −304 to −255 upstream of the E1a initiation site, e.g., corresponding to 195-244 of the Ad5 genome (SEQ ID NO: 1), hereafter referred to as the TAV-255 deletion. In certain embodiments, the TAV-255 deletion results in an E1a promoter that comprises the sequence GGTGTTTTGG (SEQ ID NO: 4).

In certain embodiments, the recombinant adenovirus comprises an E1a promoter having a deletion of a functional TATA box, e.g., the deletion of an entire TATA box. As used herein, a "functional TATA box" refers to a TATA box that is capable of binding to a TATA box binding protein (TBP), e.g., a TATA box that has at least 100%, at least 90%, at least 80%, at least 70%, at least 60%, at least 50%, or at least 40%, of the TBP binding activity of a corresponding wild-type TATA box sequence. As used herein, a "non-functional TATA box" refers to a TATA box that, e.g., has less than 30%, less than 20%, less than 10%, or 0% of the TBP binding activity of a corresponding wild-type TATA box sequence. Assays for determining whether a TBP binds to a TATA box are known in the art. Exemplary binding assays include electrophoretic mobility shift assays, chromatin immunoprecipitation assays, and DNAse footprinting assays.

For example, in certain embodiments, the recombinant adenovirus comprises a deletion of nucleotides corresponding to −27 to −24, −31 to −24, −44 to +54, or −146 to +54 of the adenovirus type 5 E1a promoter, which correspond, respectively, to nucleotides 472 to 475, 468 to 475, 455 to 552, and 353 to 552 of the Ad5 genome (SEQ ID NO: 1). In certain embodiments, the virus comprises a deletion of nucleotides corresponding to −29 to −26, −33 to −26, −44 to +52, or −148 to +52 of the adenovirus type 5 E1a promoter. In certain embodiments, the virus comprises a deletion of nucleotides corresponding to 353 to 552 of the Ad5 genome (SEQ ID NO: 1). In certain embodiments, the virus comprises a polynucleotide deletion that results in a virus comprising the sequence CTAGGACTG (SEQ ID NO: 5), AGTGCCCG (SEQ ID NO: 16), or TATTCCCG (SEQ ID NO: 17), which result from joining the two polynucleotide sequences that would otherwise flank the deleted polynucleotide sequence. In certain embodiments, the virus comprises a polynucleotide deletion that results in a virus comprising the sequence CTAGGACTG (SEQ ID NO: 5).

In certain embodiments, the recombinant adenovirus comprises an E1a promoter having a deletion of a functional CAAT box, e.g., the deletion of an entire CAAT box. As used herein, a "functional CAAT box" refers to a CAAT box that is capable of binding to a C/EBP or NF—Y protein, e.g., a CAAT box that has at least 100%, at least 90%, at least 80%, at least 70%, at least 60%, at least 50%, or at least 40%, of the a C/EBP or NF—Y binding activity of a corresponding wild-type CAAT box sequence. As used herein, a "non-functional CAAT box" refers to a CAAT box that, e.g., has less than 30%, less than 20%, less than 10%, or 0% of the a C/EBP or NF—Y binding activity of a corresponding wild-type CAAT box sequence. Assays for determining whether a C/EBP or NF—Y protein binds to a CAAT box are known in the art. Exemplary binding assays include electrophoretic mobility shift assays, chromatin immunoprecipitation assays, and DNAse footprinting assays.

For example, in certain embodiments, a recombinant adenovirus comprises a deletion of nucleotides corresponding to −76 to −68 of the adenovirus type 5 E1a promoter, which corresponds to nucleotides 423 to 431 of the Ad5 genome (SEQ ID NO: 1). In certain embodiments, the virus comprises a polynucleotide deletion that results in a virus comprising the sequence TTCCGTGGCG (SEQ ID NO: 18), which results from joining the two polynucleotide sequences that would otherwise flank the deleted polynucleotide sequence.

The adenoviral E1b-19k gene functions primarily as an anti-apoptotic gene and is a homolog of the cellular anti-apoptotic gene, BCL-2. Since host cell death prior to maturation of the progeny viral particles would restrict viral replication, E1b-19k is expressed as part of the E1 cassette to prevent premature cell death thereby allowing the infection to proceed and yield mature virions. Accordingly, in certain embodiments, a recombinant adenovirus is provided that includes an E1b-19K insertion site, e.g., the recombinant adenovirus has a nucleotide sequence encoding a transgene inserted into an E1b-19K insertion site. In certain embodiments, the insertion site is located between the start site of E1b-19K (i.e., the nucleotide sequence encoding the start codon of E1b-19k, e.g., corresponding to nucleotides 1714-1716 of SEQ ID NO: 1) and the start site of E1b-55K (i.e., the nucleotide sequence encoding the start codon of E1b-55k, e.g., corresponding to nucleotides 2019-2021 of SEQ ID NO: 1). In certain embodiments, the E1b-19K insertion site is located between the start site of E1b-19K (i.e., the nucleotide sequence encoding the start codon of E1b-19k, e.g., corresponding to nucleotides 1714-1716 of SEQ ID NO: 1) and the stop site of E1b-19K (i.e., the nucleotide sequence encoding the stop codon of E1b-19k, e.g., corresponding to nucleotides 2242-2244 of SEQ ID NO: 1).

Throughout the description and claims, an insertion between two sites, for example, an insertion between (i) a start site of a first gene (e.g., E1b-19k) and a start site of a second gene, (e.g., E1b-55K), (ii) a start site of a first gene and a stop site of a second gene, (iii) a stop site of a first gene and start site of a second gene, or (iv) a stop site of first gene and a stop site of a second gene, is understood to mean that all or a portion of the nucleotides constituting a given start site or a stop site surrounding the insertion may be present or absent in the final virus. Similarly, an insertion between two nucleotides is understood to mean that the nucleotides surrounding the insertion may be present or absent in the final virus.

In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent the start site of E1b-19K. In certain embodiments, the E1b-19K insertion site comprises a deletion of about 200 nucleotides, e.g., 202 or 203 nucleotides adjacent the start site of E1b-19K. In certain embodiments, the E1b-19K insertion site comprises a deletion corresponding to nucleotides 1714-1917 or 1714-1916 of the Ad5 genome (SEQ ID NO: 1). In certain embodiments, the first nucleotide sequence, the third nucleotide sequence, and the second nucleotide sequence is inserted between nucleotides corresponding to 1714 and 1917 or between nucleotides corresponding to 1714 and 1916 of the Ad5 genome (SEQ ID NO: 1). In certain embodiments, the first nucleotide sequence, the third nucleotide sequence, and the second nucleotide sequence is inserted between CTGACCTC (SEQ ID NO: 2) and TCACCAGG (SEQ ID NO: 3), e.g., the recombinant adenovirus comprises, in a 5' to 3' orientation, CTGACCTC (SEQ ID NO: 2), the first nucleotide sequence, the third nucleotide sequence, the second nucleotide sequence, and TCACCAGG (SEQ ID NO: 3). CTGACCTC (SEQ ID NO: 2) and TCACCAGG (SEQ ID NO: 3) define unique boundary sequences for an E1b-19K insertion site within the Ad5 genome (SEQ ID NO: 1). Throughout the description and claims, a deletion adjacent a site, for example, a deletion adjacent a start site of a gene or a deletion adjacent a stop site of a gene, is understood to mean that the deletion may include a deletion of all, a portion, or none of the nucleotides constituting a given start site or a stop site.

In certain embodiments the recombinant adenovirus comprises an E3 deletion. In certain embodiments, the E3 deletion comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or from about 3000 to about 3185 nucleotides. In certain embodiments the E3 deletion is located between the stop site of pVIII (i.e., the nucleotide sequence encoding the stop codon of pVIII, e.g., corresponding to nucleotides 27855-27857 of SEQ ID NO: 1) and the start site of Fiber (i.e., the nucleotide sequence encoding the start codon of Fiber, e.g., corresponding to nucleotides 31042-31044 of SEQ ID NO: 1). In certain embodiments, the E3 deletion is located between the stop site of E3-10.5K (i.e., the nucleotide sequence encoding the stop codon of E3-10.5K, e.g., corresponding to nucleotides 29770-29772 of SEQ ID NO: 1) and the stop site of E3-14.7K (i.e., the nucleotide sequence encoding the stop codon of E3-14.7K, e.g., corresponding to nucleotides 30837-30839 of SEQ ID NO: 1). In certain embodiments, the E3 deletion comprises a deletion of from about 500 to about 1551, from about 500 to about 1500, from about 500 to about 1000, from about 1000 to about 1551, from about 1000 to about 1500, or from about 1500 to about 1551 nucleotides adjacent the stop site of E3-10.5K. In certain embodiments, the E3 deletion comprises a deletion of about 1050 nucleotides adjacent the stop site of E3-10.5K, e.g., the E3 deletion comprises a deletion of 1063 or 1064 nucleotides adjacent the stop site of E3-10.5K. In certain embodiments, the E3 deletion comprises a deletion corresponding to the Ad5 dl309 E3 deletion. In certain embodiments, the E3 deletion comprises a deletion corresponding to nucleotides 29773-30836 of the Ad5 genome (SEQ ID NO: 1).

In certain embodiments, the E3 deletion is located between stop site of E3-19K (i.e., the nucleotide sequence encoding the stop codon of E3-gp19K, e.g., corresponding to nucleotides 29215-29217 of SEQ ID NO: 1) and the stop site of E3-14.7K (i.e., the nucleotide sequence encoding the stop codon of E3-14.7K, e.g., corresponding to nucleotides 30837-30839 of SEQ ID NO: 1). In certain embodiments, the E3 deletion comprises a deletion of from about 500 to about 1824, from about 500 to about 1500, from about 500 to about 1000, from about 1000 to about 1824, from about 1000 to about 1500, or from about 1500 to about 1824 nucleotides adjacent the stop site of E3-gp19K. In certain embodiments, the E3 deletion comprises a deletion of about 1600 nucleotides adjacent the stop site of E3-gp19K. e.g., the E3 deletion comprises a deletion of 1622 nucleotides adjacent the stop site of E3-19K. In certain embodiments, the E3 deletion comprises a deletion corresponding to nucleotides 29218-30839 of the Ad5 genome (SEQ ID NO: 1).

In certain embodiments, a recombinant adenovirus is provided that includes an E3 insertion site, e.g., the recombinant adenovirus has a nucleotide sequence encoding a therapeutic transgene inserted into an E3 insertion site. In certain embodiments the recombinant adenovirus comprises an E3 deletion. In certain embodiments, the E3 deletion comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or from about 3000 to about 3185 nucleotides. In certain embodiments the E3 deletion is located between the stop site of pVIII (i.e., the nucleotide sequence encoding the stop codon of pVIII, e.g., corresponding to nucleotides 27855-27857 of SEQ ID NO: 1) and the start site of Fiber (i.e., the nucleotide sequence encoding the start codon of Fiber, e.g., corresponding to nucleotides 31042-31044 of SEQ ID NO: 1). In certain embodiments, the E3 deletion is located between the stop site of E3-10.5K (i.e., the nucleotide sequence encoding the stop codon of E3-10.5K, e.g., corresponding to nucleotides 29770-29772 of SEQ ID NO: 1) and the stop site of E3-14.7K (i.e., the nucleotide sequence encoding the stop codon of E3-14.7K, e.g., corresponding to nucleotides 30837-30839 of SEQ ID NO: 1). In certain embodiments, the E3 deletion comprises a deletion of from about 500 to about 1551, from about 500 to about 1500, from about 500 to about 1000, from about 1000 to about 1551, from about 1000 to about 1500, or from about 1500 to about 1551 nucleotides adjacent the stop site of E3-10.5K. In certain embodiments, the E3 deletion comprises a deletion of about 1050 nucleotides adjacent the stop site of E3-10.5K, e.g., the E3 deletion comprises a deletion of 1063 or 1064 nucleotides adjacent the stop site of E3-10.5K. In certain embodiments, the E3 deletion comprises a deletion corresponding to the Ad5 dl309 E3 deletion. In certain embodiments, the E3 deletion comprises a deletion corresponding to nucleotides 29773-30836 of the Ad5 genome (SEQ ID NO: 1). In certain embodiments, the first nucleotide sequence, the third nucleotide sequence, and the second nucleotide sequence are inserted between nucleotides corresponding to 29773 and 30836 of the Ad5 genome (SEQ ID NO: 1). In certain embodiments, the first nucleotide sequence, the third nucleotide sequence, and the second nucleotide sequence are inserted between CAGTATGA (SEQ ID NO: 19) and TAATAAAAAA (SEQ ID NO: 20), e.g., the recombinant adenovirus comprises, in a 5' to 3' orientation, CAGTATGA (SEQ ID NO: 19), the first nucleotide sequence, the third nucleotide sequence, the second nucleotide sequence, and TAATAAAAAA (SEQ ID NO: 20). CAGTATGA (SEQ ID NO: 19) and TAATAAAAAA (SEQ ID NO: 20) define unique boundary sequences for an E3 insertion site within the Ad5 genome (SEQ ID NO: 1).

In certain embodiments, the E3 insertion site is located between stop site of E3-gp19K (i.e., the nucleotide sequence encoding the stop codon of E3-gp19K, e.g., corresponding to nucleotides 29215-29217 of SEQ ID NO: 1) and the stop site of E3-14.7K (i.e., the nucleotide sequence encoding the stop codon of E3-14.7K, e.g., corresponding to nucleotides 30837-30839 of SEQ ID NO: 1). In certain embodiments, the E3 insertion site comprises a deletion of from about 500 to about 1824, from about 500 to about 1500, from about 500 to about 1000, from about 1000 to about 1824, from about 1000 to about 1500, or from about 1500 to about 1824 nucleotides adjacent the stop site of E3-gp19K. In certain embodiments, the E3 insertion site comprises a deletion of about 1600 nucleotides adjacent the stop site of E3-gp19K. e.g., the E3 insertion site comprises a deletion of 1622 nucleotides adjacent the stop site of E3-gp19K. In certain embodiments, the E3 insertion site comprises a deletion corresponding to nucleotides 29218-30839 of the Ad5 genome (SEQ ID NO: 1). In certain embodiments, the first nucleotide sequence, the third nucleotide sequence, and the second nucleotide sequence are inserted between nucleotides corresponding to 29218 and 30839 of the Ad5 genome (SEQ ID NO: 1). In certain embodiments, the first nucleotide sequence, the third nucleotide sequence, and the second nucleotide sequence are inserted between TGCCTTAA (SEQ ID NO: 21) and TAAAAAAAAAT (SEQ ID NO: 22), e.g., the recombinant adenovirus comprises, in a 5' to 3' orientation, TGCCTTAA (SEQ ID NO: 21), the first nucleotide sequence, the third nucleotide sequence, the second nucleotide sequence, and TAAAAAAAAAT (SEQ ID NO: 22). TGCCTTAA (SEQ ID NO: 21) and TAAAAAAAAAT (SEQ ID NO: 22) define unique boundary sequences for an E3 insertion site within the Ad5 genome (SEQ ID NO: 1).

In certain embodiments, a recombinant adenovirus comprises an E4 deletion. In certain embodiments, the E4 deletion is located between the start site of E4-ORF6/7 (i.e., the nucleotide sequence encoding the start codon of E4-ORF6/7, e.g., corresponding to nucleotides 34075-34077 of SEQ ID NO: 1) and the right inverted terminal repeat (ITR; e.g., corresponding to nucleotides 35836-35938 of SEQ ID NO: 1). In certain embodiments, the E4 deletion is located between the start site of E4-ORF6/7 and the start site of E4-ORF1 (i.e., the nucleotide sequence encoding the start codon of E4-ORF1, e.g., corresponding to nucleotides 35524-35526 of SEQ ID NO: 1). In certain embodiments, the E4 deletion comprises a deletion of a nucleotide sequence between the start site of E4-ORF6/7 and the start site of E4-ORF1. In certain embodiments, the E4 deletion comprises a deletion of from about 500 to about 2500, from about 500 to about 2000, from about 500 to about 1500, from about 500 to about 1000, from about 1000 to about 2500, from about 1000 to about 2000, from about 1000 to about 1500, from about 1500 to about 2500, from about 1500 to about 2000, or from about 2000 to about 2500 nucleotides. In certain embodiments, the E4 deletion comprises a deletion of from about 250 to about 1500, from about 250 to about 1250, from about 250 to about 1000, from about 250 to about 750, from about 250 to about 500, from 500 to about 1500, from about 500 to about 1250, from about 500 to about 1000, from about 500 to about 750, from 750 to about 1500, from about 750 to about 1250, from about 750 to about 1000, from about 1000 to about 1500, or from about 1000 to about 1250 nucleotides adjacent the start site of E4-ORF6/7. In certain embodiments, the E4 deletion comprises a deletion of about 1450 nucleotides adjacent the start site of E4-ORF6/7, e.g., the E4 deletion comprises a deletion of about 1449 nucleotides adjacent the start site of E4-ORF6/7. In certain embodiments, the E4 deletion comprises a deletion corresponding to nucleotides 34078-35526 of the Ad5 genome (SEQ ID NO: 1).

II. Methods of Viral Production

Methods for producing recombinant viruses of the invention are known in the art. Typically, a disclosed virus is produced in a suitable host cell line using conventional techniques including culturing a transfected or infected host cell under suitable conditions so as to allow the production of infectious viral particles. Nucleic acids encoding viral genes can be incorporated into plasmids and introduced into host cells through conventional transfection or transformation techniques. Exemplary suitable host cells for production of disclosed viruses include human cell lines such as HeLa, Hela-S3, HEK293, 911, A549, HER96, or PER-C6 cells. Specific production and purification conditions will vary depending upon the virus and the production system employed. For adenovirus, the traditional method for the generation of viral particles is co-transfection followed by subsequent in vivo recombination of a shuttle plasmid (usually containing a small subset of the adenoviral genome and optionally containing a potential transgene an expression cassette) and an adenoviral helper plasmid (containing most of the entire adenoviral genome).

Alternative technologies for the generation of adenovirus include utilization of the bacterial artificial chromosome (BAC) system, in vivo bacterial recombination in a recA+ bacterial strain utilizing two plasmids containing complementary adenoviral sequences, and the yeast artificial chromosome (YAC) system.

Following production, infectious viral particles are recovered from the culture and optionally purified. Typical purification steps may include plaque purification, centrifugation, e.g., cesium chloride gradient centrifugation, clarification, enzymatic treatment, e.g., benzonase or protease treatment, chromatographic steps, e.g., ion exchange chromatography or filtration steps.

III. Therapeutic Transgenes

A disclosed recombinant adenovirus may comprise a nucleotide sequence that encodes for a therapeutic transgene. In certain embodiments, a disclosed recombinant adenovirus may comprise a first nucleotide sequence and a second nucleotide sequence that encode for a first and a second therapeutic transgene, respectively.

A therapeutic transgene may encode a therapeutic nucleic acid, e.g., an antisense RNA or ribozyme RNA. The therapeutic transgene may encode a therapeutic peptide or polypeptide, e.g., an apoptotic agent, antibody, CTL responsive peptide, cytokine, cytolytic agent, cytotoxic agent, enzyme, heterologous antigen expressed on the surface of a tumor cell to elicit an immune response, immunostimulatory or immunomodulatory agent, interferon, lytic peptide, oncoprotein, polypeptide which catalyzes processes leading to cell death, polypeptide which complements genetic defects in somatic cells, tumor suppressor protein, vaccine antigen, or any combination thereof.

In certain embodiments, the first and/or second therapeutic transgene encodes a polypeptide selected from acetylcholine, an anti-CTLA-4 antibody heavy chain or light chain, an anti-PD-1 antibody heavy chain or light chain, an anti-PD-L1 antibody heavy chain or light, BORIS/CTCFL, CD19, CD20, CD40L, CD70, CD80, CD86, CD137, CD137L, CD154, DKK1/Wnt, FGF, GITRL, GM-CSF, ICAM, IL-1, IL-2, IL-3, IL-4, IL-5, IL-6, IL-7, IL-8, IL-9, an IL-10 trap, IL-15, an IL-15 IL-15 receptor fusion protein, IL-17, IL-23, IL-23A/p19, IL-12B/p40, IL-24, IL-27, IL-27A/p28, IL-27B/EBI3, IL-35, interferon-gamma, MAGE, NY-ESO-1, Ox40L, p53, secreted flagellin, TGF-β, a TGF-β trap, thymidine kinase, and TNF-alpha.

In certain embodiments, the first and/or second therapeutic transgene encodes a polypeptide selected from acetylcholine, an anti-CTLA-4 antibody heavy chain or light chain, an anti-PD-1 antibody heavy chain or light chain, an anti-PD-L1 antibody heavy chain or light, BORIS/CTCFL, CD19, CD20, CD40L, CD70, CD80, CD86, CD137, CD137L, CD154, DKK1/Wnt, FGF, GITRL, GM-CSF, ICAM, IL-1, IL-2, IL-3, IL-4, IL-5, IL-6, IL-7, IL-8, IL-9, an IL-10 trap, IL-12, IL-12A/p35, IL-12B/p40, IL-15, an IL-15 IL-15 receptor fusion protein, IL-23A/p19, interferon-gamma, MAGE, NY-ESO-1, Ox40L, p53, secreted flagellin, TGF-β, a TGF-β trap, thymidine kinase, and TNF-alpha.

In certain embodiments, the first and second therapeutic transgene encode a first and second subunit, respectively, of a heterodimeric protein, e.g., a heterodimeric cytokine. For example, in certain embodiments the first and/or second therapeutic transgenes are selected from IL-12A/p35 and IL-12B/p40, which make up the heterodimeric cytokine IL-12. For example the first therapeutic transgene may encode IL-12B/p40 and the second therapeutic transgene may encode IL-12A/p35. In certain embodiments, the recombinant adenovirus comprises a nucleotide sequence encoding an amino acid sequence that is encoded by nucleotides 17-1000 of SEQ ID NO: 8, nucleotides 1013-1606 of SEQ ID NO: 8, and/or nucleotides 17-1606 of SEQ ID NO: 8. In certain embodiments, the recombinant adenovirus comprises the nucleotide sequence of SEQ ID NO: 8, or comprises a sequence having 80%, 85%, 86%, 87%, 88%, 89%, 90%, 91%, 92%, 93%, 94%, 95%, 96%, 97%, 98%, or 99% sequence identity to SEQ ID NO: 8.

Additionally, in certain embodiments, the first and/or second therapeutic transgenes are selected from IL-23A/p19 and IL-12B/p40, which make up the heterodimeric cytokine IL-23. For example the first therapeutic transgene may encode IL-12B/p40 and the second therapeutic transgene may encode IL-23A/p19. In certain embodiments, the recombinant adenovirus comprises a nucleotide sequence encoding an amino acid sequence that is encoded by nucleotides 17-1000 of SEQ ID NO: 9, nucleotides 1013-1582 of SEQ ID NO: 9, and/or nucleotides 17-1582 of SEQ ID NO: 9. In certain embodiments, the recombinant adenovirus comprises the nucleotide sequence of SEQ ID NO: 9, or comprises a sequence having 80%, 85%, 86%, 87%, 88%, 89%, 90%, 91%, 92%, 93%, 94%, 95%, 96%, 97%, 98%, or 99% sequence identity to SEQ ID NO: 9.

Additionally, in certain embodiments, the first and/or second therapeutic transgenes are selected from IL-27A/p28 and IL-27B/EBI3, which make up the heterodimeric cytokine IL-23.

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) Proc. Natl. Acad. Sci. USA 87:2264-2268; Altschul, (1993) J. Mol. Evol. 36, 290-300; Altschul et al., (1997) Nucleic Acids Res. 25:3389-3402, incorporated by reference) are tailored for sequence similarity searching. For a discussion of basic issues in searching sequence databases see Altschul et al., (1994) Nature Genetics 6:119-129, which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89:10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: —G, Cost to open gap [Integer]: default=5 for nucleotides/11 for proteins; —E, Cost to extend gap [Integer]: default=2 for nucleotides/1 for proteins; —q, Penalty for nucleotide mismatch [Integer]: default=−3; —r, reward for nucleotide match [Integer]: default=1; —e, expect value [Real]: default=10; —W, wordsize [Integer]: default=11 for nucleotides/28 for megablast/3 for proteins; —y, Dropoff (X) for blast extensions in bits: default=20 for blastn/7 for others; —X, X dropoff value for gapped alignment (in bits): default=15 for all programs, not applicable to blastn; and —Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In certain embodiments, the size of the first and second therapeutic transgenes when combined comprises from about 500 to about 5000, from about 500 to about 4000, from about 500 to about 3000, from about 500 to about 2000, from about 500 to about 1000, from about 1000 to about 5000, from about 1000 to about 4000, from about 1000 to about 3000, from about 1000 to about 2000, from about 2000 to about 5000, from about 2000 to about 4000, from about 2000 to about 3000, from about 3000 to about 5000, from about 3000 to about 4000, or from about 4000 to 5000 nucleotides. In certain embodiments, the size of the first and second therapeutic transgenes when combined comprises from about 500 to about 7000, from about 500 to about 6000, from about 500 to about 5000, from about 500 to about 4000, from about 500 to about 3000, from about 500 to about 2000, from about 500 to about 1000, from about 1000 to about 7000, from about 1000 to about 6000, from about 1000 to about 5000, from about 1000 to about 4000, from about 1000 to about 3000, from about 1000 to about 2000, from about 2000 to about 7000, from about 2000 to about 6000, from about 2000 to about 5000, from about 2000 to about 4000, from about 2000 to about 3000, from about 3000 to about 7000, from about 3000 to about 6000, from about 3000 to about 5000, from about 3000 to about 4000, from about 4000 to about 7000, from about 4000 to about 6000, from about 4000 to about 5000 nucleotides, from about 5000 to about 7000, from about 5000 to about 6000, or from about 6000 to about 7000 nucleotides.

In certain embodiments, the size of the first and second therapeutic transgenes when combined comprises at least from about 500 to about 5000, from about 500 to about 4000, from about 500 to about 3000, from about 500 to about 2000, from about 500 to about 1000, from about 1000 to about 5000, from about 1000 to about 4000, from about 1000 to about 3000, from about 1000 to about 2000, from about 2000 to about 5000, from about 2000 to about 4000, from about 2000 to about 3000, from about 3000 to about 5000, from about 3000 to about 4000, or from about 4000 to 5000 nucleotides. In certain embodiments, the size of the first and second therapeutic transgenes when combined comprises at least from about 500 to about 7000, from about 500 to about 6000, from about 500 to about 5000, from about 500 to about 4000, from about 500 to about 3000, from about 500 to about 2000, from about 500 to about 1000, from about 1000 to about 7000, from about 1000 to about 6000, from about 1000 to about 5000, from about 1000 to about 4000, from about 1000 to about 3000, from about 1000 to about 2000, from about 2000 to about 7000, from about 2000 to about 6000, from about 2000 to about 5000, from about 2000 to about 4000, from about 2000 to about 3000, from about 3000 to about 7000, from about 3000 to about 6000, from about 3000 to about 5000, from about 3000 to about 4000, from about 4000 to about 7000, from about 4000 to about 6000, from about 4000 to about 5000 nucleotides, from about 5000 to about 7000, from about 5000 to about 6000, or from about 6000 to about 7000 nucleotides.

In certain embodiments, the size of the first and second therapeutic transgenes when combined comprises at least about 500, about 1000, about 2000, about 3000, about 4000, or about 5000 nucleotides. In certain embodiments, the size of the first and second therapeutic transgenes when combined comprises at least about 500, about 1000, about 2000, about 3000, about 4000, about 5000 nucleotides, about 6000, or about 7000 nucleotides. In certain embodiments, the size of the first and second therapeutic transgenes when combined comprises about 1600 nucleotides, about 1650 nucleotides, or about 3100 nucleotides.

In certain embodiments the first and second therapeutic transgenes are separated by a linker. The linker may comprise a cleavage site, e.g., a proteolytic or a non-proteolytic cleavage site, or a ribosome skipping sequence, e.g., a T2A sequence. In certain embodiments, the first and second therapeutic transgenes are separated by a proteolytic cleavage site. In certain embodiments, the proteolytic cleavage site is cleaved by a protease present in a specific tissue, organelle or intracellular compartment. In certain embodiments, the linker comprises a proteolytic cleavage site and two cysteine residues that result in a disulfide linkage following proteolytic cleavage. In certain embodiments, the proteolytic cleavage site is cleaved by a protease selected from a matrix metalloproteinase (MMP), furin, PC1, PC2, PC3, cathepsin B, proteinase 3, and caspase 3.

In certain embodiments, the cleavage site is a proteolytic cleavage site that is cleaved by a protease that is present in an endoplasmic reticulum or golgi of a eukaryotic cell. In certain embodiments, the proteolytic cleavage site is a furin cleavage site. Furin is a protease that is ubiquitously expressed and is localized to the Golgi, where it recognizes the consensus sequence $RX_1X_2R$ (SEQ ID NO: 6), wherein $X_1$ is any amino acid, and $X_2$ is Lys or Arg, and cleaves after the final Arg. Furin plays a biological role in cleaving propeptides of proteins that are trafficked through the Golgi. Accordingly, in certain embodiments the proteolytic cleavage site is a furin cleavage site comprising the sequence $RX_1X_2R$ (SEQ ID NO: 6), wherein $X_1$ is any amino acid, and $X_2$ is Lys or Arg, e.g., a furin cleavage site comprising the sequence RAKR (SEQ ID NO: 7).

III. Pharmaceutical Compositions

For therapeutic use, a recombinant adenovirus disclosed herein is preferably combined with a pharmaceutically acceptable carrier. As used herein, “pharmaceutically acceptable carrier” means buffers, carriers, and excipients suitable for use in contact with the tissues of human beings and animals without excessive toxicity, irritation, allergic response, or other problem or complication, commensurate with a reasonable benefit/risk ratio. The carrier(s) should be “acceptable” in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing recombinant adenoviruses can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. Useful formulations can be prepared by methods known in the pharmaceutical art. For example, see *Reming-*

*ton's Pharmaceutical Sciences,* 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The term "effective amount" as used herein refers to the amount of an active component (e.g., the amount of a recombinant adenovirus) sufficient to effect beneficial or desired results. An effective amount can be administered in one or more administrations, applications or dosages and is not intended to be limited to a particular formulation or administration route.

In certain embodiments, a therapeutically effective amount of active component is in the range of 0.1 mg/kg to 100 mg/kg, e.g., 1 mg/kg to 100 mg/kg, 1 mg/kg to 10 mg/kg. In certain embodiments, a therapeutically effective amount of the recombinant adenovirus is in the range of $10^2$ to $10^{15}$ plaque forming units (pfus), e.g., $10^2$ to $10^{10}$, $10^2$ to $10^5$, $10^5$ to $10^{15}$, $10^5$ to $10^{10}$, or $10^{10}$ to $10^{15}$ plaque forming units. The amount administered will depend on variables such as the type and extent of disease or indication to be treated, the overall health of the patient, the in vivo potency of the active component, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the recombinant adenovirus, and the disease being treated. Exemplary dosing frequencies are once per day, once per week and once every two weeks.

IV. Therapeutic Uses

The recombinant adenoviruses disclosed herein can be used to treat various medical indications, for example, cancers. As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodyplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma).

In certain embodiments, the cancer is selected from anal cancer, basal cell carcinoma, bladder cancer, bone cancer, brain cancer, breast cancer, carcinoma, cholangiocarcinoma, cervical cancer, colon cancer, colorectal cancer, endometrial cancer, gastroesophageal cancer, gastrointestinal (GI) cancer, gastrointestinal stromal tumor, hepatocellular carcinoma, gynecologic cancer, head and neck cancer, hematologic cancer, kidney cancer, leukemia, liver cancer, lung cancer, lymphoma, melanoma, merkel cell carcinoma, mesothelioma, neuroendocrine cancer, non-small cell lung cancer, ovarian cancer, pancreatic cancer, pediatric cancer, prostate cancer, renal cell carcinoma, sarcoma, skin cancer, small cell lung cancer, squamous cell carcinoma of the skin, stomach cancer, testicular cancer and thyroid cancer.

In certain embodiments, the cancer is selected from nasopharyngeal cancer, basal cell carcinoma, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, neuroendocrine, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

In certain embodiments, a recombinant adenovirus is administered to the subject in combination with one or more therapies, e.g., surgery, radiation, chemotherapy, immunotherapy, hormone therapy, or virotherapy. In certain embodiments, a recombinant adenovirus is administered in combination with a tyrosine kinase inhibitor, e.g., erlotinib. In certain embodiments, a recombinant adenovirus is administered in combination with a checkpoint inhibitor, e.g., an anti-CTLA-4 antibody, an anti-PD-1 antibody, or an anti-PD-L1 antibody. Exemplary anti-PD-1 antibodies include, for example, nivolumab (Opdivo®, Bristol-Myers Squibb Co.), pembrolizumab (Keytruda®, Merck Sharp & Dohme Corp.), PDR001 (Novartis Pharmaceuticals), and pidilizumab (CT-011, Cure Tech). Exemplary anti-PD-L1 antibodies include, for example, atezolizumab (Tecentriq®, Genentech), duvalumab (AstraZeneca), MEDI4736, avelumab, and BMS 936559 (Bristol Myers Squibb Co.).

The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In certain embodiments, the effective amount of the recombinant virus is identified by measuring an immune response to an antigen in the subject and/or the method of treating the subject further comprises measuring an immune response to an antigen in the subject. Cancers may be characterized by immunosuppression, and measuring an immune response to an antigen in the subject may be indicative of the level of immunosuppression in the subject. Accordingly, measuring an immune response to an antigen in the subject may be indicative of the efficacy of the treatment and/or the effective amount of the recombinant virus. The immune response to the antigen in the subject may be measured by any method known in the art. In certain embodiments, the immune response to the antigen is measured by injecting the subject with the antigen at an injection site on the skin of the subject and measuring the size of an induration or amount of inflammation at the injection site. In certain embodiments, the immune response to the antigen is measured by release of a cytokine from a cell of the subject (e.g., interferon gamma, IL-4 and/or IL-5) upon exposure to the antigen.

Throughout the description, where viruses, compositions and systems are described as having, including, or comprising specific components, or where processes and methods are described as having, including, or comprising specific steps, it is contemplated that, additionally, there are compositions, devices, and systems of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a virus, a composition, a system, a method, or a process described herein can be combined in a variety of ways without departing from the spirit and scope of the present invention, whether explicit or implicit herein. For example, where reference is made to a particular virus, that virus can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

At various places in the present specification, viruses, compositions, systems, processes and methods, or features thereof, are disclosed in groups or in ranges. It is specifically intended that the description include each and every individual subcombination of the members of such groups and ranges. By way of other examples, an integer in the range of 1 to 20 is specifically intended to individually disclose 1, 2, 3, 4, 5, 6, 7, 8, 9, 10, 11, 12, 13, 14, 15, 16, 17, 18, 19, and 20.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1: Expression of Heterodimeric IL-12

Interleukin 12 (IL-12) is a cytokine that promotes cell-mediated immunity. IL-12 contains two separate protein chains, IL-12A/p35 and IL-12B/p40, which combine to form the active heterodimer denoted IL-12p70. This Example describes the expression of a human IL-12 heterodimer including both of the IL-12 subunits IL-12A/p35 and IL-12B/p40.

The plasmid pAd1, which carries a portion of the adenovirus type 5 genome, was modified to carry a Sa1I site at the start site of the E1b-19k region and an XhoI site 200 base pairs 3' of the Sa1I site to facilitate insertion of therapeutic transgenes. The resulting plasmid is hereafter referred to as pAd1-Δ19k.

The nucleotide sequence of the modified E1b-19k region is as follows, with the residual bases from the fused Sa1I and XhoI sites underlined:

```
                                                 (SEQ ID NO: 10)
ATCTTGGTTACATCTGACCTCGTCGAGTCACCAGGCGCTTTTCCAA.
```

A nucleotide sequence encoding human IL-12A/p35 followed by an encephalomyocarditis virus (EMCV) IRES followed by a nucleotide sequence encoding human IL-12B/p40 was cloned into the modified E1b-19k region of pAd1-Δ19k. The resulting plasmid is hereafter referred to as pAd1-hIL-12-IRES. The nucleotide sequence encoding human IL-12A/p35 followed by the EMCV IRES followed by the nucleotide sequence encoding human IL-12B/p40 inserted into the E1b-19k region is as follows, where the IL-12A/p35 and IL-12B/p40 coding regions are capitalized, the IRES is lowercase, and the flanking E1b-19k sequences including the Sa1I and XhoI restriction sites are underlined:

```
                                                 (SEQ ID NO: 11)
ATCTGACCTCGTCGACATGTGGCCCCCTGGGTCAGCCTCCCAGCCACCGCCCTCACCTGCCGC
GGCCACAGGTCTGCATCCAGCGGCTCGCCCTGTGTCCCTGCAGTGCCGGCTCAGCATGTGTCC
AGCGCGCAGCCTCCTCCTTGTGGCTACCCTGGTCCTCCTGGACCACCTCAGTTTGGCCAGAAA
CCTCCCCGTGGCCACTCCAGACCCAGGAATGTTCCCATGCCTTCACCACTCCCAAAACCTGCT
GAGGGCCGTCAGCAACATGCTCCAGAAGGCCAGACAAACTCTAGAATTTTACCCTTGCACTTC
TGAAGAGATTGATCATGAAGATATCACAAAAGATAAAACCAGCACAGTGGAGGCCTGTTTACC
ATTGGAATTAACCAAGAATGAGAGTTGCCTAAATTCCAGAGAGACCTCTTTCATAACTAATGG
GAGTTGCCTGGCCTCCAGAAAGACCTCTTTTATGATGGCCCTGTGCCTTAGTAGTATTTATGA
AGACTTGAAGATGTACCAGGTGGAGTTCAAGACCATGAATGCAAAGCTTCTGATGGATCCTAA
GAGGCAGATCTTTCTAGATCAAAACATGCTGGCAGTTATTGATGAGCTGATGCAGGCCCTGAA
TTTCAACAGTGAGACTGTGCCACAAAAATCCTCCCTTGAAGAACCGGATTTTTATAAAACTAA
AATCAAGCTCTGCATACTTCTTCATGCTTTCAGAATTCGGGCAGTGACTATTGATAGAGTGAT
GAGCTATCTGAATGCTTCCTAATAAtaacgttactggccgaagccgcttggaataaggccggt
gtgcgtttgtctatatgttattttccaccatattgccgtcttttggcaatgtgagggcccgga
aacctggccctgtcttcttgacgagcattcctaggggtctttcccctctcgccaaaggaatgc
aaggtctgttgaatgtcgtgaaggaagcagttcctctggaagcttcttgaagacaaacaacgt
ctgtagcgaccctttgcaggcagcggaaccccccacctggcgacaggtgcctctgcggccaaa
agccacgtgtataagatacacctgcaaaggcggcacaaccccagtgccacgttgtgagttgga
tagttgtggaaagagtcaaatggctctcctcaagcgtattcaacaaggggctgaaggatgccc
agaaggtaccccattgtatgggatctgatctggggcctcggtgcacatgctttacatgtgttt
agtcgaggttaaaaaacgtctaggccccccgaaccacggggacgtggttttcctttgaaaaac
acgatgataatATGTGTCACCAGCAGTTGGTCATCTCTTGGTTTTCCCTGGTTTTTCTGGCAT
```

-continued

CTCCCCTCGTGGCCATATGGGAACTGAAGAAAGATGTTTATGTCGTAGAATTGGATTGGTATC

CGGATGCCCCTGGAGAAATGGTGGTCCTCACCTGTGACACCCCTGAAGAAGATGGTATCACCT

GGACCTTGGACCAGAGCAGTGAGGTCTTAGGCTCTGGCAAAACCCTGACCATCCAAGTCAAAG

AGTTTGGAGATGCTGGCCAGTACACCTGTCACAAAGGAGGCGAGGTTCTAAGCCATTCGCTCC

TGCTGCTTCACAAAAAGGAAGATGGAATTTGGTCCACTGATATTTTAAAGGACCAGAAAGAAC

CCAAAAATAAGACCTTTCTAAGATGCGAGGCCAAGAATTATTCTGGACGTTTCACCTGCTGGT

GGCTGACGACAATCAGTACTGATTTGACATTCAGTGTCAAAAGCAGCAGAGGCTCTTCTGACC

CCCAAGGGGTGACGTGCGGAGCTGCTACACTCTCTGCAGAGAGAGTCAGAGGGGACAACAAGG

AGTATGAGTACTCAGTGGAGTGCCAGGAGGACAGTGCCTGCCCAGCTGCTGAGGAGAGTCTGC

CCATTGAGGTCATGGTGGATGCCGTTCACAAGCTCAAGTATGAAAACTACACCAGCAGCTTCT

TCATCAGGGACATCATCAAACCTGACCCACCCAAGAACTTGCAGCTGAAGCCATTAAAGAATT

CTCGGCAGGTGGAGGTCAGCTGGGAGTACCCTGACACCTGGAGTACTCCACATTCCTACTTCT

CCCTGACATTCTGCGTTCAGGTCCAGGGCAAGAGCAAGAGAGAAAAGAAAGATAGAGTCTTCA

CGGACAAGACCTCAGCCACGGTCATCTGCCGCAAAAATGCCAGCATTAGCGTGCGGGCCCAGG

ACCGCTACTATAGCTCATCTTGGAGCGAATGGGCATCTGTGCCCTGCAGTTAGTAACTCGAGT

CACCAGGCG.

Additionally, a nucleotide sequence encoding human IL-12B/p40 followed by a nucleotide sequence encoding a furin cleavage site (RAKR) followed by a nucleotide sequence encoding human IL-12A/p35 was cloned into the modified E1b-19k region of pAd1-Δ19k. The resulting plasmid is hereafter referred to as pAd1-hIL-12-furin. The nucleotide sequence encoding human IL-12B/p40 followed by the nucleotide sequence encoding the furin cleavage site followed by the nucleotide sequence encoding human IL-12A/p35 inserted into the E1b-19k region is as follows, where the IL-12B/p40 and IL-12A/p35 coding regions are capitalized, the furin cleavage site coding region is lowercase, and the flanking E1b-19k sequences including the Sa1I and XhoI restriction sites are underlined:

(SEQ ID NO: 8)

ATCTGACCTCGTCGACATGTGTCACCAGCAGTTGGTCATCTCTTGGTTTTCCCTGGTTTTTCT

GGCATCTCCCCTCGTGGCCATATGGGAACTGAAGAAAGATGTTTATGTCGTAGAATTGGATTG

GTATCCGGATGCCCCTGGAGAAATGGTGGTCCTCACCTGTGACACCCCTGAAGAAGATGGTAT

CACCTGGACCTTGGACCAGAGCAGTGAGGTCTTAGGCTCTGGCAAAACCCTGACCATCCAAGT

CAAAGAGTTTGGAGATGCTGGCCAGTACACCTGTCACAAAGGAGGCGAGGTTCTAAGCCATTC

GCTCCTGCTGCTTCACAAAAAGGAAGATGGAATTTGGTCCACTGATATTTTAAAGGACCAGAA

AGAACCCAAAAATAAGACCTTTCTAAGATGCGAGGCCAAGAATTATTCTGGACGTTTCACCTG

CTGGTGGCTGACGACAATCAGTACTGATTTGACATTCAGTGTCAAAAGCAGCAGAGGCTCTTC

TGACCCCCAAGGGGTGACGTGCGGAGCTGCTACACTCTCTGCAGAGAGAGTCAGAGGGGACAA

CAAGGAGTATGAGTACTCAGTGGAGTGCCAGGAGGACAGTGCCTGCCCAGCTGCTGAGGAGAG

TCTGCCCATTGAGGTCATGGTGGATGCCGTTCACAAGCTCAAGTATGAAAACTACACCAGCAG

CTTCTTCATCAGGGACATCATCAAACCTGACCCACCCAAGAACTTGCAGCTGAAGCCATTAAA

GAATTCTCGGCAGGTGGAGGTCAGCTGGGAGTACCCTGACACCTGGAGTACTCCACATTCCTA

CTTCTCCCTGACATTCTGCGTTCAGGTCCAGGGCAAGAGCAAGAGAGAAAAGAAAGATAGAGT

CTTCACGGACAAGACCTCAGCCACGGTCATCTGCCGCAAAAATGCCAGCATTAGCGTGCGGGC

CCAGGACCGCTACTATAGCTCATCTTGGAGCGAATGGGCATCTGTGCCCTGCAGTcgtgctaa gcgaAGAAACCTCCCCGTGGCCACTCCAGACCCAGGAATGTTCCCATGCCTTCACCACTCCCA

AAACCTGCTGAGGGCCGTCAGCAACATGCTCCAGAAGGCCAGACAAACTCTAGAATTTTACCC

-continued

```
TTGCACTTCTGAAGAGATTGATCATGAAGATATCACAAAAGATAAAACCAGCACAGTGGAGGC

CTGTTTACCATTGGAATTAACCAAGAATGAGAGTTGCCTAAATTCCAGAGAGACCTCTTTCAT

AACTAATGGGAGTTGCCTGGCCTCCAGAAAGACCTCTTTTATGATGGCCCTGTGCCTTAGTAG

TATTTATGAAGACTTGAAGATGTACCAGGTGGAGTTCAAGACCATGAATGCAAAGCTTCTGAT

GGATCCTAAGAGGCAGATCTTTCTAGATCAAAACATGCTGGCAGTTATTGATGAGCTGATGCA

GGCCCTGAATTTCAACAGTGAGACTGTGCCACAAAAATCCTCCCTTGAAGAACCGGATTTTTA

TAAAACTAAAATCAAGCTCTGCATACTTCTTCATGCTTTCAGAATTCGGGCAGTGACTATTGA

TAGAGTGATGAGCTATCTGAATGCTTCCTAACTCGAGTCACCAGGCG.
```

Additionally, a nucleotide sequence encoding human IL-12B/p40 followed by a nucleotide sequence encoding a 2A peptide followed by a nucleotide sequence encoding human IL-12A/p35 was cloned into the modified E1b-19k region of pAd1-Δ19k. The resulting plasmid is hereafter referred to as pAd1-hIL-12-2A. The nucleotide sequence encoding human IL-12B/p40 followed by the nucleotide sequence encoding the 2A peptide followed by the nucleotide sequence encoding human IL-12A/p35 inserted into the E1b-19k region is as follows, where the IL-12B/p40 and IL-12A/p35 coding regions are capitalized, the 2A coding region is lowercase, and the flanking E1b-19k sequences including the Sa1I and XhoI restriction sites are underlined:

```
(SEQ ID NO: 12)
ATCTGACCTCGTCGACATGTGTCACCAGCAGTTGGTCATCTCTTGGTTTTCCCTGGTTTTTCT

GGCATCTCCCCTCGTGGCCATATGGGAACTGAAGAAAGATGTTTATGTCGTAGAATTGGATTG

GTATCCGGATGCCCCTGGAGAAATGGTGGTCCTCACCTGTGACACCCCTGAAGAAGATGGTAT

CACCTGGACCTTGGACCAGAGCAGTGAGGTCTTAGGCTCTGGCAAAACCCTGACCATCCAAGT

CAAAGAGTTTGGAGATGCTGGCCAGTACACCTGTCACAAAGGAGGCGAGGTTCTAAGCCATTC

GCTCCTGCTGCTTCACAAAAAGGAAGATGGAATTTGGTCCACTGATATTTTAAAGGACCAGAA

AGAACCCAAAAATAAGACCTTTCTAAGATGCGAGGCCAAGAATTATTCTGGACGTTTCACCTG

CTGGTGGCTGACGACAATCAGTACTGATTTGACATTCAGTGTCAAAAGCAGCAGAGGCTCTTC

TGACCCCCAAGGGGTGACGTGCGGAGCTGCTACACTCTCTGCAGAGAGAGTCAGAGGGGACAA

CAAGGAGTATGAGTACTCAGTGGAGTGCCAGGAGGACAGTGCCTGCCCAGCTGCTGAGGAGAG

TCTGCCCATTGAGGTCATGGTGGATGCCGTTCACAAGCTCAAGTATGAAAACTACACCAGCAG

CTTCTTCATCAGGGACATCATCAAACCTGACCCACCCAAGAACTTGCAGCTGAAGCCATTAAA

GAATTCTCGGCAGGTGGAGGTCAGCTGGGAGTACCCTGACACCTGGAGTACTCCACATTCCTA

CTTCTCCCTGACATTCTGCGTTCAGGTCCAGGGCAAGAGCAAGAGAGAAAAGAAAGATAGAGT

CTTCACGGACAAGACCTCAGCCACGGTCATCTGCCGCAAAAATGCCAGCATTAGCGTGCGGGC

CCAGGACCGCTACTATAGCTCATCTTGGAGCGAATGGGCATCTGTGCCCTGCAGTcttctgaa

cttcgacctcctcaagttggcgggagacgttgagtccaaccccgggcccAGAAACCTCCCCGT

GGCCACTCCAGACCCAGGAATGTTCCCATGCCTTCACCACTCCCAAAACCTGCTGAGGGCCGT

CAGCAACATGCTCCAGAAGGCCAGACAAACTCTAGAATTTTACCCTTGCACTTCTGAAGAGAT

TGATCATGAAGATATCACAAAAGATAAAACCAGCACAGTGGAGGCCTGTTTACCATTGGAATT

AACCAAGAATGAGAGTTGCCTAAATTCCAGAGAGACCTCTTTCATAACTAATGGGAGTTGCCT

GGCCTCCAGAAAGACCTCTTTTATGATGGCCCTGTGCCTTAGTAGTATTTATGAAGACTTGAA

GATGTACCAGGTGGAGTTCAAGACCATGAATGCAAAGCTTCTGATGGATCCTAAGAGGCAGAT

CTTTCTAGATCAAAACATGCTGGCAGTTATTGATGAGCTGATGCAGGCCCTGAATTTCAACAG

TGAGACTGTGCCACAAAAATCCTCCCTTGAAGAACCGGATTTTTATAAAACTAAAATCAAGCT
```

-continued

CTGCATACTTCTTCATGCTTTCAGAATTCGGGCAGTGACTATTGATAGAGTGATGAGCTATCT

GAATGCTTCCTAACTCGAGTCACCAGGCG.

Details of the plasmids tested are shown in TABLE 1.

TABLE 1

| Plasmid | E1b-19k |
|---|---|
| pAd1-Δ19k | Deleted |
| pAd1-hIL-12-IRES | Deleted and Replaced with IL-12A/p35-IRES-IL-12B/p40 |
| pAd1-hIL-12-furin | Deleted and Replaced with IL-12B/p40-furin-IL-12A/p35 |
| pAd1-hIL-12-2A | Deleted and Replaced with IL-12B/p40-2A-IL-12A/p35 |

Plasmids were transiently transfected into HEK-293 cells. Conditioned media was collected four days after transfection, and IL-12 concentration was measured in an ELISA (Biolegend 431704) that specifically detects the heterodimer of the IL-12A/p35 and IL-12B/p40 subunits. As shown in FIG. 1, the plasmid carrying the furin cleavage site (pAd1-hIL-12-furin) elicited significantly higher heterodimeric IL-12 expression than either the plasmid utilizing the IRES (pAd1-hIL-12-IRES) or the 2A peptide (pAd1-hIL-12-2A).

Example 2: IL-12 Expressing Adenoviruses

This Example describes recombinant type 5 (Ad5) adenoviruses that express the human IL-12 subunits IL-12A/p35 and IL-12B/p40.

An adenovirus type 5 virus was constructed that carried the deletion of a nucleotide region located from −304 to −255 upstream of the E1a initiation, which renders E1a expression cancer-selective (as previously described in U.S. Pat. No. 9,073,980). The resulting virus is hereafter referred to as TAV.

TAV was further modified to carry a SalI site at the start site of the E1b-19k region and an XhoI site 200 base pairs 3' of the SalI site to facilitate insertion of therapeutic transgenes. The resulting virus is hereafter referred to as TAV-Δ19k. The nucleotide sequence of the modified E1b-19k region is as follows, with the residual bases from the fused SalI and XhoI sites underlined:

(SEQ ID NO: 10)
ATCTTGGTTACATCTGACCTCGTCGAGTCACCAGGCGCTTTTCCAA.

TAV-Δ19k carried the dl309 disruption in the E3 region. To create viruses carrying therapeutic transgenes that would otherwise render the viral genome too large to be packaged into a viral capsid, TAV-Δ19k was further modified to delete the entire RIDα, RIDβ, and 14.7k genes of the E3 region. The resulting virus is hereafter referred to as TAV-Δ19k-ΔE3. The nucleotide sequence of the modified E3 region is as follows, with the hyphen indicating the point of deletion:

(SEQ ID NO: 13)
TCTTTTCTCTTACAGTATGA-TAATAAAAAAAAATAATAAAGCATCACTT

A.

A nucleotide sequence encoding human IL-12B/p40 followed by a nucleotide sequence encoding a furin cleavage site (RAKR) followed by a nucleotide sequence encoding human IL-12A/p35 was cloned into the modified E1b-19k region of TAV-Δ19k-ΔE3. The resulting virus is hereafter referred to as TAV-hIL-12-furin. The nucleotide sequence encoding human IL-12B/p40 followed by the nucleotide sequence encoding the furin cleavage site followed by the nucleotide sequence encoding human IL-12A/p35 inserted into the E1b-19k region is as follows, where the IL-12B/p40 and IL-12A/p35 coding regions are capitalized, the furin cleavage site coding region is lowercase, and the flanking E1b-19k sequence including the SalI and XhoI restriction sites is underlined:

(SEQ ID NO: 8)
ATCTGACCTCGTCGACATGTGTCACCAGCAGTTGGTCATCTCTTGGTTTTCCCTGGTTTTTCT

GGCATCTCCCCTCGTGGCCATATGGGAACTGAAGAAAGATGTTTATGTCGTAGAATTGGATTG

GTATCCGGATGCCCCTGGAGAAATGGTGGTCCTCACCTGTGACACCCCTGAAGAAGATGGTAT

CACCTGGACCTTGGACCAGAGCAGTGAGGTCTTAGGCTCTGGCAAAACCCTGACCATCCAAGT

CAAAGAGTTTGGAGATGCTGGCCAGTACACCTGTCACAAAGGAGGCGAGGTTCTAAGCCATTC

GCTCCTGCTGCTTCACAAAAAGGAAGATGGAATTTGGTCCACTGATATTTTAAAGGACCAGAA

AGAACCCAAAAATAAGACCTTTCTAAGATGCGAGGCCAAGAATTATTCTGGACGTTTCACCTG

CTGGTGGCTGACGACAATCAGTACTGATTTGACATTCAGTGTCAAAAGCAGCAGAGGCTCTTC

TGACCCCCAAGGGGTGACGTGCGGAGCTGCTACACTCTCTGCAGAGAGAGTCAGAGGGGACAA

CAAGGAGTATGAGTACTCAGTGGAGTGCCAGGAGGACAGTGCCTGCCCAGCTGCTGAGGAGAG

TCTGCCCATTGAGGTCATGGTGGATGCCGTTCACAAGCTCAAGTATGAAAACTACACCAGCAG

CTTCTTCATCAGGGACATCATCAAACCTGACCCACCCAAGAACTTGCAGCTGAAGCCATTAAA

GAATTCTCGGCAGGTGGAGGTCAGCTGGGAGTACCCTGACACCTGGAGTACTCCACATTCCTA

-continued

CTTCTCCCTGACATTCTGCGTTCAGGTCCAGGGCAAGAGCAAGAGAGAAAAGAAAGATAGAGT

CTTCACGGACAAGACCTCAGCCACGGTCATCTGCCGCAAAAATGCCAGCATTAGCGTGCGGGC

CCAGGACCGCTACTATAGCTCATCTTGGAGCGAATGGGCATCTGTGCCCTGCAGTcgtgctaa gcgaAGAAACCTCCCCGTGGCCACTCCAGACCCAGGAATGTTCCCATGCCTTCACCACTCCCA

AAACCTGCTGAGGGCCGTCAGCAACATGCTCCAGAAGGCCAGACAAACTCTAGAATTTTACCC

TTGCACTTCTGAAGAGATTGATCATGAAGATATCACAAAAGATAAAACCAGCACAGTGGAGGC

CTGTTTACCATTGGAATTAACCAAGAATGAGAGTTGCCTAAATTCCAGAGAGACCTCTTTCAT

AACTAATGGGAGTTGCCTGGCCTCCAGAAAGACCTCTTTTATGATGGCCCTGTGCCTTAGTAG

TATTTATGAAGACTTGAAGATGTACCAGGTGGAGTTCAAGACCATGAATGCAAAGCTTCTGAT

GGATCCTAAGAGGCAGATCTTTCTAGATCAAAACATGCTGGCAGTTATTGATGAGCTGATGCA

GGCCCTGAATTTCAACAGTGAGACTGTGCCACAAAAATCCTCCCTTGAAGAACCGGATTTTTA

TAAAACTAAAATCAAGCTCTGCATACTTCTTCATGCTTTCAGAATTCGGGCAGTGACTATTGA

TAGAGTGATGAGCTATCTGAATGCTTCCTAACTCGAGTCACCAGGCG.

Additionally, a nucleotide sequence encoding human IL-12B/p40 was cloned into the modified E1b-19k region of TAV-Δ19k-ΔE3, and a nucleotide sequence encoding human IL-12A/p35 was cloned into the modified E3 region of TAV-Δ19k-ΔE3. The resulting virus is hereafter referred to as TAV-hIL-12-Separate. The nucleotide sequence encoding human IL-12B/p40 inserted into the E1b-19k region is as follows, where the flanking E1b-19k sequence including the Sa1I and XhoI restriction sites is underlined:

(SEQ ID NO: 14)

ATCTGACCTCGTCGACATGTGTCACCAGCAGTTGGTCATCTCTTGGTTTTCCCTGGTTTTTCT

GGCATCTCCCCTCGTGGCCATATGGGAACTGAAGAAAGATGTTTATGTCGTAGAATTGGATTG

GTATCCGGATGCCCCTGGAGAAATGGTGGTCCTCACCTGTGACACCCCTGAAGAAGATGGTAT

CACCTGGACCTTGGACCAGAGCAGTGAGGTCTTAGGCTCTGGCAAAACCCTGACCATCCAAGT

CAAAGAGTTTGGAGATGCTGGCCAGTACACCTGTCACAAAGGAGGCGAGGTTCTAAGCCATTC

GCTCCTGCTGCTTCACAAAAAGGAAGATGGAATTTGGTCCACTGATATTTTAAAGGACCAGAA

AGAACCCAAAAATAAGACCTTTCTAAGATGCGAGGCCAAGAATTATTCTGGACGTTTCACCTG

CTGGTGGCTGACGACAATCAGTACTGATTTGACATTCAGTGTCAAAAGCAGCAGAGGCTCTTC

TGACCCCCAAGGGGTGACGTGCGGAGCTGCTACACTCTCTGCAGAGAGAGTCAGAGGGGACAA

CAAGGAGTATGAGTACTCAGTGGAGTGCCAGGAGGACAGTGCCTGCCCAGCTGCTGAGGAGAG

TCTGCCCATTGAGGTCATGGTGGATGCCGTTCACAAGCTCAAGTATGAAAACTACACCAGCAG

CTTCTTCATCAGGGACATCATCAAACCTGACCCACCCAAGAACTTGCAGCTGAAGCCATTAAA

GAATTCTCGGCAGGTGGAGGTCAGCTGGGAGTACCCTGACACCTGGAGTACTCCACATTCCTA

CTTCTCCCTGACATTCTGCGTTCAGGTCCAGGGCAAGAGCAAGAGAGAAAAGAAAGATAGAGT

CTTCACGGACAAGACCTCAGCCACGGTCATCTGCCGCAAAAATGCCAGCATTAGCGTGCGGGC

CCAGGACCGCTACTATAGCTCATCTTGGAGCGAATGGGCATCTGTGCCCTGCAGTTAGTAACT

CGAGTCACCAGGCG.

The nucleotide sequence encoding human IL-12A/p35 inserted into the E3 region is as follows, where the flanking adenoviral sequence is underlined:

(SEQ ID NO: 15)

ATGTTCTTTTCTCTTACAGTATGATTAAATGAGACATGTGGCCCCCTGGGTCTGCCTCCCAAC

CACCGCCCTCACCTGCCGCGGCCACTGGTCTGCATCCTGCGGCTCGCCCTGTGTCCCTGCAAT

-continued

GCCGGCTCTCCATGTGTCCTGCGCGCTCCCTCCTCCTTGTGGCTACCCTGGTCCTCCTGGACC

ACCTCTCTTTGGCCCGAAACCTCCCCGTGGCCACTCCTGACCCTGGAATGTTCCCATGCCTTC

ACCACTCCCAAAACCTGCTGCGGGCCGTCTCCAACATGCTCCAAAAAGCCCGACAAACTCTTG

AATTTTACCCTTGCACTTCTGAAGAAATTGATCATGAAGATATCACAAAAGATAAAACCTCCA

CTGTGGAAGCCTGTTTACCATTGGAATTAACCAAAAATGAATCTTGCCTAAATTCCCGAGAAA

CCTCTTTCATAACTAATGGGTCTTGCCTGGCCTCCCGAAAAACCTCTTTTATGATGGCCCTGT

GCCTTTCTTCTATTTATGAAGACTTGAAAATGTACCAAGTGGAATTCAAAACCATGAATGCAA

AACTTCTGATGGATCCTAAACGGCAAATCTTTCTTGATCAAAACATGCTGGCTGTTATTGATG

AACTGATGCAAGCCCTGAATTTCAACTCTGAAACTGTGCCACAAAAATCCTCCCTTGAAGAAC

CGGATTTTTATAAAACTAAAATCAAACTCTGCATACTTCTTCATGCTTTCCGAATTCGGGCTG

TGACTATTGATCGAGTGATGTCCTATCTGAATGCTTCCTAATGAGGTCTCAAAGATCTTATTC

CCTTTAACTAATAAA.

Details of the viruses tested are shown in TABLE 2.

TABLE 2

| Virus | E1A Promoter | E1b-19k Modification | E3 (RIDα, RIDβ, and 14.7k) Modification |
|---|---|---|---|
| TAV-Δ19k | TAV-255 | Deleted | Disrupted (containing the dl309 sequence) |
| TAV-hIL-12-Separate | TAV-255 | Deleted and replaced with IL-12B/p40 | Deleted and replaced with IL-12A/p35 |
| TAV -hIL-12-furin | TAV-255 | Deleted and replaced with IL-12B/p40-furin-IL-12A/p35 | Deleted |

Figure 2:
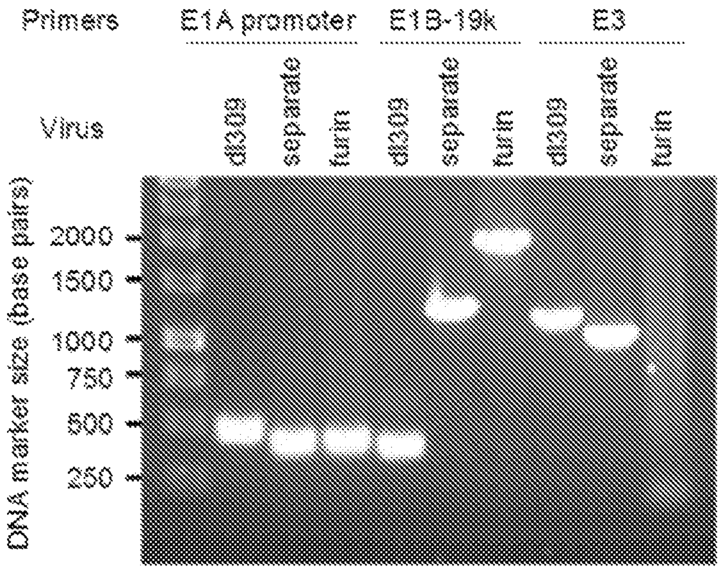
FIG. 2 is a gel depicting PCR products of DNA from the TAV-hIL-12-furin adenovirus (indicated as "furin"), the TAV-hIL-12-Separate adenovirus (indicated as "separate") and the control dl309 adenovirus, demonstrating the anticipated size products.

Viral genomic DNA from lysate of those viruses, as well as a control virus (dl309), was PCR-amplified with primers flanking the E1A promoter, with primers flanking the E1b-19k region, and with primers flanking the E3 RIDα, RIDβ, and 14.7k region to confirm presence of the desired elements. As seen in FIG. 2, the viruses had the desired features, namely, PCR products of the anticipated size. The IL-12 coding regions in both viruses were sequenced for confirmation.

Example 3: IL-23 Expressing Adenovirus

This Example describes a recombinant adenovirus type 5 (Ad5) that expresses the human IL-23 subunits IL-23A/p19 and IL-12B/p40.

A TAV-Δ19k-ΔE3 virus is generated as described in Example 2. A nucleotide sequence encoding human IL-12B/p40 followed by a nucleotide sequence encoding a furin cleavage site (RAKR) followed by a nucleotide sequence encoding human IL-23A/p19 is cloned into the modified E1b-19k region of TAV-Δ19k-ΔE3. The resulting virus is hereafter referred to as TAV-hIL-23-furin. The nucleotide sequence encoding human IL-12B/p40 followed by the nucleotide sequence encoding the furin cleavage site followed by the nucleotide sequence encoding human IL-23A/p19 inserted into the E1b-19k region is as follows, where the IL-12B/p40 and IL-23A/p19 coding regions are capitalized, the furin cleavage site coding region is lowercase, and the flanking E1b-19k sequence including the Sa1I and XhoI restriction sites is underlined:

(SEQ ID NO: 9)

ATCTGACCTCGTCGACATGTGTCACCAGCAGTTGGTCATCTCTTGGTTTTCCCTGGTTTTTCT

GGCATCTCCCCTCGTGGCCATATGGGAACTGAAGAAAGATGTTTATGTCGTAGAATTGGATTG

GTATCCGGATGCCCCTGGAGAAATGGTGGTCCTCACCTGTGACACCCCTGAAGAAGATGGTAT

CACCTGGACCTTGGACCAGAGCAGTGAGGTCTTAGGCTCTGGCAAAACCCTGACCATCCAAGT

CAAAGAGTTTGGAGATGCTGGCCAGTACACCTGTCACAAAGGAGGCGAGGTTCTAAGCCATTC

GCTCCTGCTGCTTCACAAAAAGGAAGATGGAATTTGGTCCACTGATATTTTAAAGGACCAGAA

AGAACCCAAAAATAAGACCTTTCTAAGATGCGAGGCCAAGAATTATTCTGGACGTTTCACCTG

CTGGTGGCTGACGACAATCAGTACTGATTTGACATTCAGTGTCAAAAGCAGCAGAGGCTCTTC

TGACCCCCAAGGGGTGACGTGCGGAGCTGCTACACTCTCTGCAGAGAGAGTCAGAGGGGACAA

CAAGGAGTATGAGTACTCAGTGGAGTGCCAGGAGGACAGTGCCTGCCCAGCTGCTGAGGAGAG

TCTGCCCATTGAGGTCATGGTGGATGCCGTTCACAAGCTCAAGTATGAAAACTACACCAGCAG

CTTCTTCATCAGGGACATCATCAAACCTGACCCACCCAAGAACTTGCAGCTGAAGCCATTAAA

-continued

```
GAATTCTCGGCAGGTGGAGGTCAGCTGGGAGTACCCTGACACCTGGAGTACTCCACATTCCTA

CTTCTCCCTGACATTCTGCGTTCAGGTCCAGGGCAAGAGCAAGAGAGAAAAGAAAGATAGAGT

CTTCACGGACAAGACCTCAGCCACGGTCATCTGCCGCAAAAATGCCAGCATTAGCGTGCGGGC

CCAGGACCGCTACTATAGCTCATCTTGGAGCGAATGGGCATCTGTGCCCTGCAGTcgtgctaa

gcgaATGCTGGGGAGCAGAGCTGTAATGCTGCTGTTGCTGCTGCCCTGGACAGCTCAGGGCAG

AGCTGTGCCTGGGGGCAGCAGCCCTGCCTGGACTCAGTGCCAGCAGCTTTCACAGAAGCTCTG

CACACTGGCCTGGAGTGCACATCCACTAGTGGGACACATGGATCTAAGAGAAGAGGGAGATGA

AGAGACTACAAATGATGTTCCCCATATCCAGTGTGGAGATGGCTGTGACCCCCAAGGACTCAG

GGACAACAGTCAGTTCTGCTTGCAAAGGATCCACCAGGGTCTGATTTTTTATGAGAAGCTGCT

AGGATCGGATATTTTCACAGGGGAGCCTTCTCTGCTCCCTGATAGCCCTGTGGGCCAGCTTCA

TGCCTCCCTACTGGGCCTCAGCCAACTCCTGCAGCCTGAGGGTCACCACTGGGAGACTCAGCA

GATTCCAAGCCTCAGTCCCAGCCAGCCATGGCAGCGTCTCCTTCTCCGCTTCAAAATCCTTCG

CAGCCTCCAGGCCTTTGTGGCTGTAGCCGCCCGGGTCTTTGCCCATGGAGCAGCAACCCTGAG

TCCCTAACTCGAGTCACCAGGCG.
```

Example 4: IL-12 Expressing Adenovirus

This Example describes a recombinant adenovirus type 5 (Ad5) that expresses the mouse IL-12 subunits IL-12A and IL-12B using an IRES.

TAV, TAV-Δ19k, and TAV-Δ19k-ΔE3 viruses were generated, as described in Example 2. A nucleotide sequence encoding mouse IL-12A followed by an EMCV IRES followed by a nucleotide sequence encoding mouse IL-12B was cloned into the modified E1b-19k region of TAV-Δ19k-ΔE3. The resulting virus is hereafter referred to as TAV-mIL-12-IRES. The nucleotide sequence encoding mouse IL-12A followed by the EMCV IRES followed by the nucleotide sequence encoding mouse IL-12B inserted into the E1b-19k region is as follows, where the mouse IL-12B and IL-12A coding regions are capitalized, the IRES is lowercase, and the flanking restriction sites and adenoviral sequences are underlined:

(SEQ ID NO: 23)

```
CTGACCTCGTCGACATGTGTCAATCACGCTACCTCCTCTTTTTGGCCACCCTTGCCCTCCTAA

ACCACCTCAGTTTGGCCAGAGTGATCCCTGTGTCCGGCCCTGCCAGATGCCTGAGCCAGAGCA

GAAACCTGCTGAAAACCACCGACGACATGGTGAAAACCGCCAGAGAGAAGCTGAAGCACTACA

GCTGCACAGCCGAGGACATCGACCACGAGGACATCACCCGGGACCAGACCTCCACCCTGAAAA

CCTGCCTGCCCCTGGAACTGCATAAGAACGAGAGCTGCCTGGCCACCCGCGAGACAAGCAGCA

CCACCAGAGGCAGCTGTCTGCCCCCCCAGAAAACCAGCCTGATGATGACCCTGTGCCTGGGCA

GCATCTACGAGGACCTGAAGATGTACCAGACCGAGTTCCAGGCCATCAACGCCGCCCTGCAGA

ACCACAACCACCAGCAGATCATCCTGGACAAGGGCATGCTGGTGGCCATCGACGAGCTGATGC

AGAGCCTGAACCACAACGGCGAAACCCTGAGACAGAAACCCCCCGTGGGCGAGGCCGACCCCT

ACAGAGTGAAGATGAAGCTGTGCATCCTGCTGCACGCCTTCAGCACCAGAGTGGTGACAATCA

ACAGAGTGATGGGCTACCTGAGCAGCGCCTGAtaacgttactggccgaagccgcttggaataa

ggccggtgtgcgtttgtctatatgttattttccaccatattgccgtcttttggcaatgtgagg

gcccggaaacctggccctgtcttcttgacgagcattcctaggggtctttcccctctcgccaaa

ggaatgcaaggtctgttgaatgtcgtgaaggaagcagttcctctggaagcttcttgaagacaa

acaacgtctgtagcgaccctttgcaggcagcggaaccccccacctggcgacaggtgcctctgc

ggccaaaagccacgtgtataagatacacctgcaaaggcggcacaaccccagtgccacgttgtg

agttggatagttgtggaaagagtcaaatggctctcctcaagcgtattcaacaaggggctgaag

gatgcccagaaggtaccccattgtatgggatctgatctggggcctcggtgcacatgctttaca

tgtgtttagtcgaggttaaaaaacgtctaggccccccgaaccacggggacgtggttttccttt
```

-continued gaaaaacacgatgataatATGTGCCCCCAGAAGCTGACCATCAGTTGGTTCGCCATCGTGCTG

CTGGTGTCCCCCCTGATGGCCATGTGGGAGCTGGAAAAGGACGTGTACGTGGTGGAAGTGGAC

TGGACCCCCGACGCCCCTGGCGAGACAGTGAACCTGACCTGCGACACCCCCGAAGAGGACGAC

ATCACCTGGACCAGCGACCAGAGACACGGCGTGATCGGCAGCGGCAAGACCCTGACAATCACC

GTGAAAGAGTTTCTGGACGCCGGCCAGTACACCTGTCACAAGGGCGGCGAGACACTGAGCCAC

TCCCATCTGCTGCTGCACAAGAAAGAGAACGGCATCTGGTCCACCGAGATCCTGAAGAACTTC

AAGAACAAGACCTTCCTGAAGTGCGAGGCCCCCAACTACAGCGGCAGATTCACCTGTAGCTGG

CTGGTGCAGAGAAACATGGACCTGAAGTTCAACATCAAGAGCAGCAGCAGCTCCCCCGACAGC

AGAGCCGTGACCTGTGGCATGGCCAGCCTGAGCGCCGAGAAAGTGACCCTGGACCAGAGAGAC

TACGAGAAGTACAGCGTGTCCTGCCAGGAAGATGTCACCTGCCCCACCGCCGAGGAAACCCTG

CCTATCGAGCTGGCCCTGGAAGCCAGACAGCAGAACAAATACGAGAACTACTCTACCAGCTTC

TTCATCCGGGACATCATCAAGCCCGACCCCCCCAAGAACCTGCAGATGAAGCCCCTGAAGAAC

AGCCAGGTGGAAGTGTCCTGGGAGTACCCCGACAGCTGGTCCACCCCCCACAGCTACTTCAGC

CTGAAGTTCTTCGTGCGGATCCAGCGCAAGAAAGAAAAGATGAAGGAAACCGAGGAAGGCTGC

AACCAGAAAGGCGCTTTCCTGGTGGAAAAGACCAGCACCGAGGTGCAGTGCAAGGGCGGCAAC

GTGTGCGTGCAGGCCCAGGACCGGTACTACAACAGCAGCTGCAGCAAGTGGGCCTGCGTGCCC

TGTAGAGTGCGCTCTTGACTCGAGTCACCAGGCGCTT.

Figure 3:
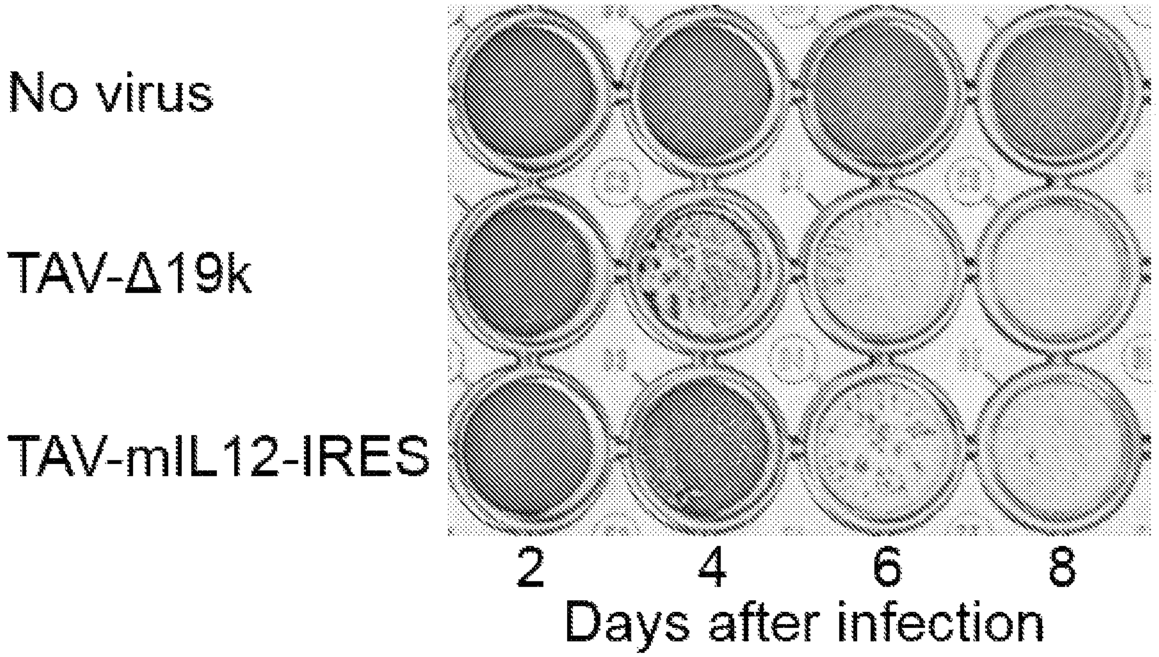
FIG. 3 depicts crystal violet staining of ADS-12 cells at the indicated time points following infection with the indicated virus. Crystal violet stains viable cells purple.

Cytotoxic activity of TAV-mIL-12-IRES was tested. ADS-12 (mouse lung cancer) cells were infected at a multiplicity of infection (MOI) of 10 with TAV-mIL12-IRES, TAV-Δ19k virus, or no virus, and stained with crystal violet, which stains viable cells purple. As depicted in FIG. 3, TAV-mIL12-IRES retained cytotoxic activity, although at a lower level than the control TAV-Δ19k virus.

Figure 4:
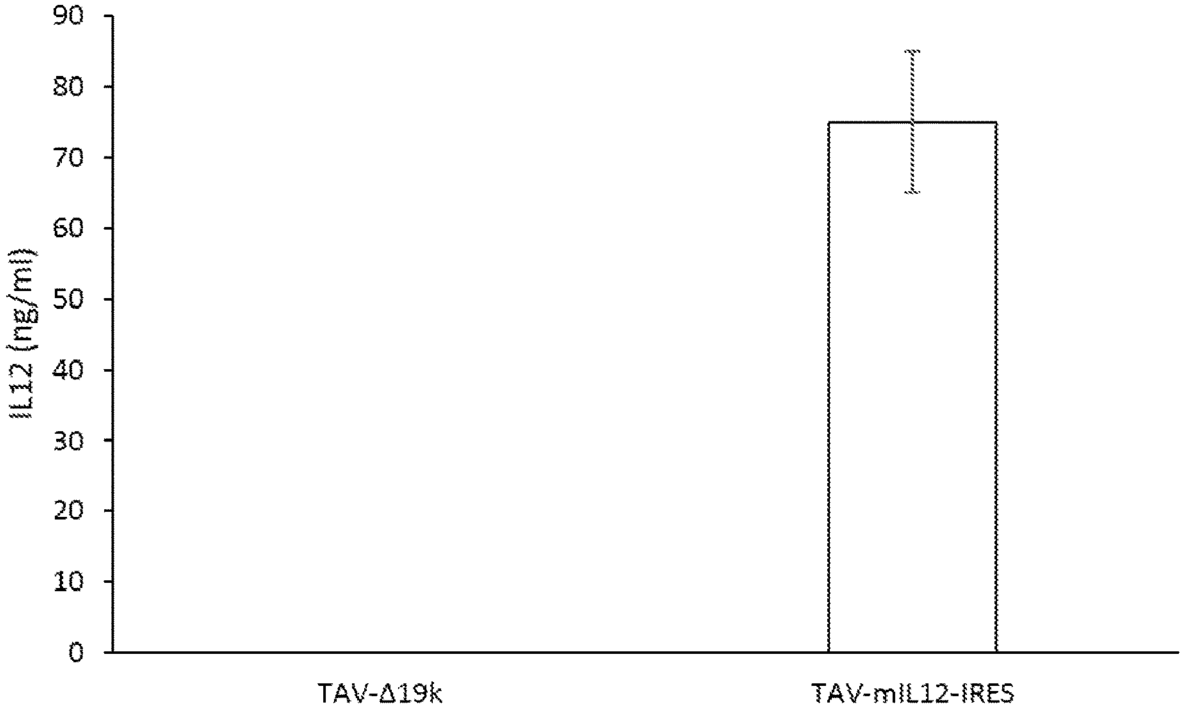
FIG. 4 is a bar graph depicting IL-12 expression from ADS-12 cells infected with TAV-Δ19k and TAV-mIL12-IRES, as determined by ELISA. Error bars represent standard deviation.

IL-12 expression from TAV-mIL-12-IRES was tested. ADS-12 cells were infected at an MOI of 5 with TAV-Δ19k or TAV-mIL-12-IRES. Conditioned media was collected five days after infection and IL-12 concentration was measured with an ELISA specific for the IL-12 heterodimer. As depicted in FIG. 4, there was no detectable expression from cells infected with TAV-Δ19k while cells infected with TAV-mIL-12-IRES expressed 67 ng/ml of the IL-12 heterodimer.

Figure 5:
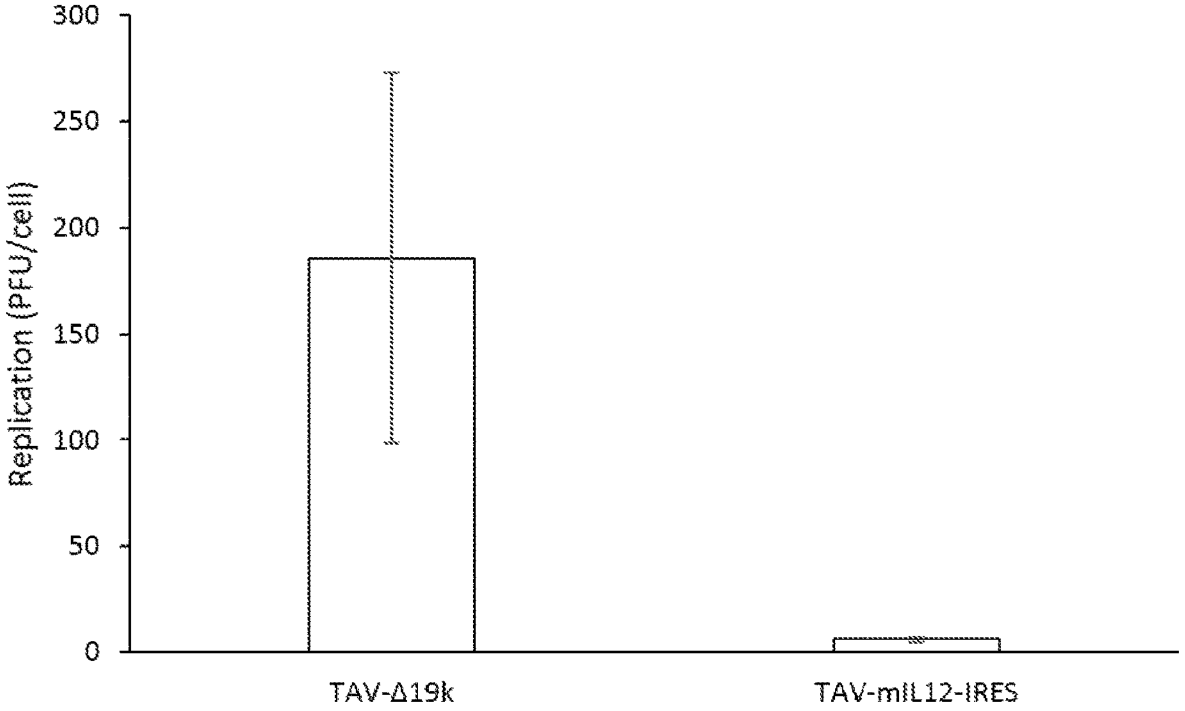
FIG. 5 is a bar graph depicting viral replication of TAV-Δ19k and TAV-mIL-12-IRES in ADS-12 cells. Error bars represent standard deviation.

Viral replication of TAV-mIL-12-IRES was tested. ADS-12 cells were infected at an MOI of 5 with TAV-mIL12-IRES or TAV-Δ19k. Media and cell lysate were harvested five days after infection and titered. Viral replication was assayed by measuring the number of plaque-forming units (PFU) of virus per infected ADS-12 cell. As depicted in FIG. 5, TAV-mIL-12-replicated at lower levels in ADS-12 cells compared to TAV-Δ19k.

Example 5: IL-12 Expressing Adenoviruses

This Example describes recombinant adenoviruses that expresses the human IL-12 subunits IL-12A and IL-12B using an IRES and recombinant adenoviruses that expresses the human IL-12 subunits IL-12A and IL-12B using a furin cleavage site.

TAV, TAV-Δ19k, TAV-Δ19k-ΔE3, and TAV-hIL-12-furin viruses were generated, as described in Example 2. Additionally, a nucleotide sequence encoding human IL-12A/p35 followed by an EMCV IRES followed by a nucleotide sequence encoding human IL-12B/p40 was cloned into the modified E1b-19k region of TAV-Δ19k-ΔE3. The resulting adenovirus is hereafter referred to as TAV-hIL-12-IRES. The nucleotide sequence encoding human IL-12A/p35 followed by the EMCV IRES followed by the nucleotide sequence encoding human IL-12B/p40 inserted into the E1b-19k region is as follows, where the IL-12A/p35 and IL-12B/p40 coding regions are capitalized, the IRES is lowercase, and the flanking E1b-19k sequence including the Sa1I and XhoI restriction sites is underlined:

(SEQ ID NO: 11)

ATCTGACCTCGTCGACATGTGGCCCCCTGGGTCAGCCTCCCAGCCACCGCCCTCACCTGCCGC

GGCCACAGGTCTGCATCCAGCGGCTCGCCCTGTGTCCCTGCAGTGCCGGCTCAGCATGTGTCC

AGCGCGCAGCCTCCTCCTTGTGGCTACCCTGGTCCTCCTGGACCACCTCAGTTTGGCCAGAAA

CCTCCCCGTGGCCACTCCAGACCCAGGAATGTTCCCATGCCTTCACCACTCCCAAAACCTGCT

GAGGGCCGTCAGCAACATGCTCCAGAAGGCCAGACAAACTCTAGAATTTTACCCTTGCACTTC

TGAAGAGATTGATCATGAAGATATCACAAAAGATAAAACCAGCACAGTGGAGGCCTGTTTACC

ATTGGAATTAACCAAGAATGAGAGTTGCCTAAATTCCAGAGAGACCTCTTTCATAACTAATGG

-continued

```
GAGTTGCCTGGCCTCCAGAAAGACCTCTTTTATGATGGCCCTGTGCCTTAGTAGTATTTATGA

AGACTTGAAGATGTACCAGGTGGAGTTCAAGACCATGAATGCAAAGCTTCTGATGGATCCTAA

GAGGCAGATCTTTCTAGATCAAAACATGCTGGCAGTTATTGATGAGCTGATGCAGGCCCTGAA

TTTCAACAGTGAGACTGTGCCACAAAAATCCTCCCTTGAAGAACCGGATTTTTATAAAACTAA

AATCAAGCTCTGCATACTTCTTCATGCTTTCAGAATTCGGGCAGTGACTATTGATAGAGTGAT

GAGCTATCTGAATGCTTCCTAATAAtaacgttactggccgaagccgcttggaataaggccggt

gtgcgtttgtctatatgttattttccaccatattgccgtcttttggcaatgtgagggcccgga

aacctggccctgtcttcttgacgagcattcctaggggtctttcccctctcgccaaaggaatgc

aaggtctgttgaatgtcgtgaaggaagcagttcctctggaagcttcttgaagacaaacaacgt

ctgtagcgaccctttgcaggcagcggaaccccccacctggcgacaggtgcctctgcggccaaa

agccacgtgtataagatacacctgcaaaggcggcacaaccccagtgccacgttgtgagttgga

tagttgtggaaagagtcaaatggctctcctcaagcgtattcaacaaggggctgaaggatgccc

agaaggtaccccattgtatgggatctgatctggggcctcggtgcacatgctttacatgtgttt

agtcgaggttaaaaaacgtctaggccccccgaaccacggggacgtggttttcctttgaaaaac

acgatgataatATGTGTCACCAGCAGTTGGTCATCTCTTGGTTTTCCCTGGTTTTTCTGGCAT

CTCCCCTCGTGGCCATATGGGAACTGAAGAAAGATGTTTATGTCGTAGAATTGGATTGGTATC

CGGATGCCCCTGGAGAAATGGTGGTCCTCACCTGTGACACCCCTGAAGAAGATGGTATCACCT

GGACCTTGGACCAGAGCAGTGAGGTCTTAGGCTCTGGCAAAACCCTGACCATCCAAGTCAAAG

AGTTTGGAGATGCTGGCCAGTACACCTGTCACAAAGGAGGCGAGGTTCTAAGCCATTCGCTCC

TGCTGCTTCACAAAAAGGAAGATGGAATTTGGTCCACTGATATTTTAAAGGACCAGAAAGAAC

CCAAAAATAAGACCTTTCTAAGATGCGAGGCCAAGAATTATTCTGGACGTTTCACCTGCTGGT

GGCTGACGACAATCAGTACTGATTTGACATTCAGTGTCAAAAGCAGCAGAGGCTCTTCTGACC

CCCAAGGGGTGACGTGCGGAGCTGCTACACTCTCTGCAGAGAGAGTCAGAGGGGACAACAAGG

AGTATGAGTACTCAGTGGAGTGCCAGGAGGACAGTGCCTGCCCAGCTGCTGAGGAGAGTCTGC

CCATTGAGGTCATGGTGGATGCCGTTCACAAGCTCAAGTATGAAAACTACACCAGCAGCTTCT

TCATCAGGGACATCATCAAACCTGACCCACCCAAGAACTTGCAGCTGAAGCCATTAAAGAATT

CTCGGCAGGTGGAGGTCAGCTGGGAGTACCCTGACACCTGGAGTACTCCACATTCCTACTTCT

CCCTGACATTCTGCGTTCAGGTCCAGGGCAAGAGCAAGAGAGAAAAGAAAGATAGAGTCTTCA

CGGACAAGACCTCAGCCACGGTCATCTGCCGCAAAAATGCCAGCATTAGCGTGCGGGCCCAGG

ACCGCTACTATAGCTCATCTTGGAGCGAATGGGCATCTGTGCCCTGCAGTTAGTAACTCGAGT

CACCAGGCG.
```

Figure 6:
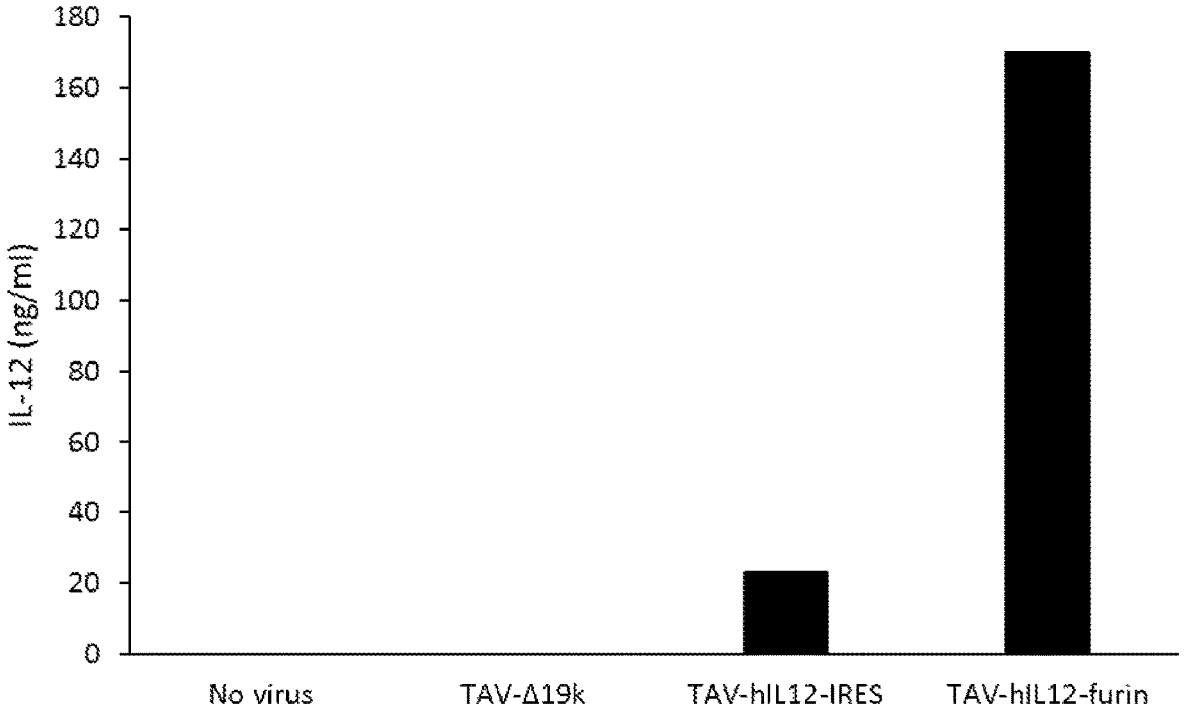
FIG. 6 is a bar graph depicting IL-12 expression from A549 cells infected with TAV-Δ19k, TAV-hIL-12-IRES, TAV-hIL-12-furin, or no virus, as determined by ELISA.

IL-12 expression from TAV-hIL-12-furin and TAV-hIL-12-IRES were tested. A549 cells were infected at an MOI of 5 with TAV-Δ19k, TAV-hIL-12-IRES, TAV-hIL-12-furin, or no virus. Conditioned media was collected four days after infection and IL-12 concentration was measured by ELISA (Biolegend 431704). As depicted in FIG. 6, expression from TAV-hIL-12-furin (170 ng/ml) was higher than from TAV-hIL-12-IRES (23 ng/ml).

Figure 7:
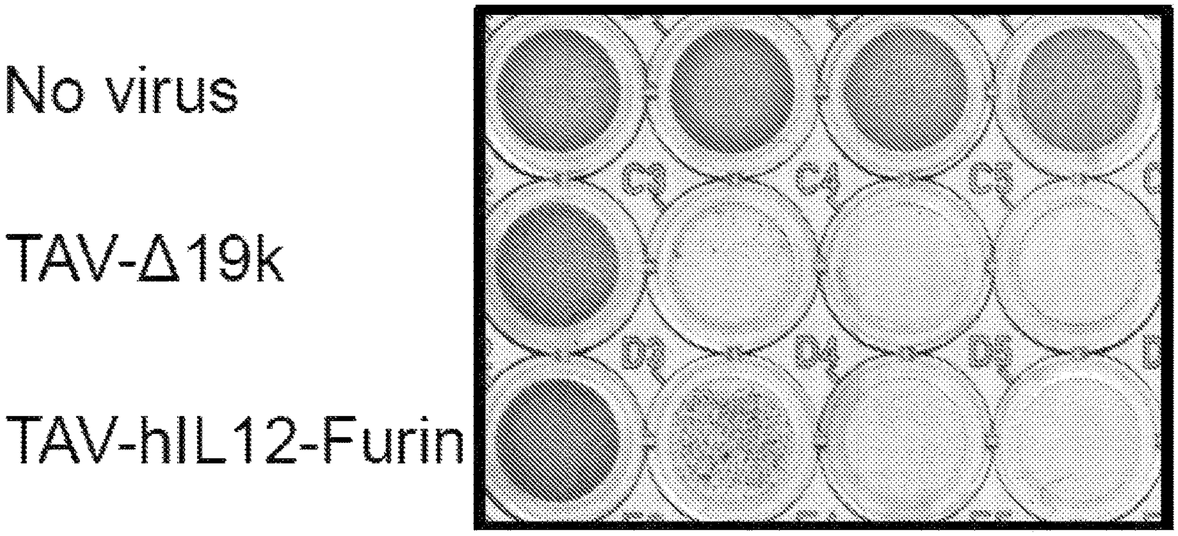
FIG. 7 depicts crystal violet staining of A549 cells at the indicated time points following infection with the indicated virus. Crystal violet stains viable cells purple.

Cytotoxic activity of TAV-hIL-12-furin was tested. A549 cells were infected at an MOI of 5 with TAV-Δ19k, TAV-hIL12-furin, or no virus, and stained with crystal violet, which stains viable cells purple. As depicted in FIG. 7, TAV-hIL12-furin retained cytotoxic activity at a similar level to the control TAV-Δ19k virus.

Viral replication of TAV-hIL-12-furin and TAV-hIL-12-IRES were tested. A549 cells were infected at an MOI of 5 with TAV-hIL-12-furin, TAV-hIL-12-IRES, or TAV-Δ19k.

Figure 8:
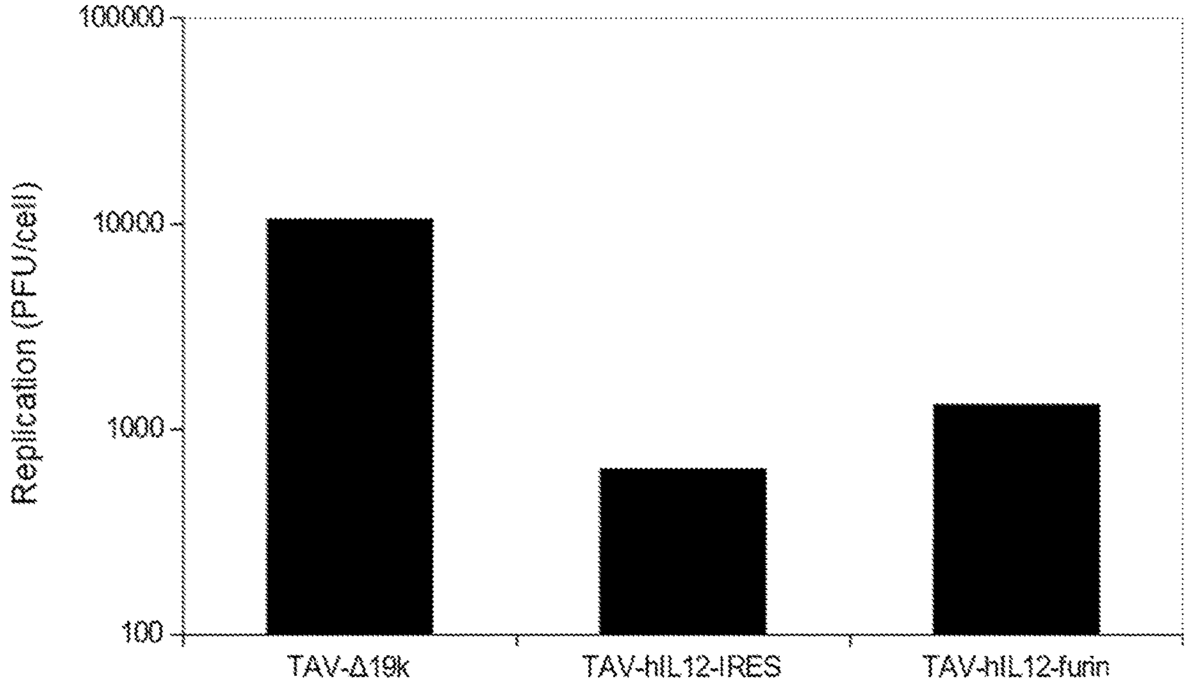
FIG. 8 is bar graph a depicting viral replication of TAV-A19k, TAV-hIL-12-IRES, and TAV-hIL-12-furin in A549 cells.

Media and cell lysate were harvested six days after infection and titered. Viral replication was assayed by measuring the number of plaque-forming units (PFU) of virus per infected A549 cell. As depicted in FIG. 8, TAV-hIL-12-furin replicated more efficiently than TAV-hIL-12-IRES.

Example 6: IL-12, IL-23, and IL-27 Expressing Adenoviruses

This Example describes recombinant adenoviruses that expresses the two subunits of mouse IL-12, IL-23, and IL-27 using a furin cleavage site.

TAV, TAV-Δ19k, and TAV-Δ19k-ΔE3 viruses were generated, as described in Example 2. A nucleotide sequence encoding mouse IL-12B followed by a nucleotide sequence encoding a furin cleavage site (RAKR) followed by a nucleotide sequence encoding mouse IL-12A was cloned into the modified E1b-19k region of TAV-Δ19k-ΔE3. The resulting virus is hereafter referred to as TAV-mIL-12-furin. The nucleotide sequence encoding mouse IL-12B followed by the nucleotide sequence encoding the furin cleavage site followed by the nucleotide sequence encoding mouse IL-12A inserted into the E1b-19k region is as follows, where the IL-12B and IL-12A coding regions are capitalized, the furin cleavage site coding region is lowercase, and the flanking E1b-19k sequence including the Sa1I and XhoI restriction sites is underlined:

(SEQ ID NO: 24)

```
ATCTGACCTCGTCGACATGTGTCCTCAGAAGCTAACCATCTCCTGGTTTGCCATCGTTTTGCT
GGTGTCTCCACTCATGGCCATGTGGGAGCTGGAGAAAGACGTTTATGTTGTAGAGGTGGACTG
GACTCCCGATGCCCCTGGAGAAACAGTGAACCTCACCTGTGACACGCCTGAAGAAGATGACAT
CACCTGGACCTCAGACCAGAGACATGGAGTCATAGGCTCTGGAAAGACCCTGACCATCACTGT
CAAAGAGTTTCTAGATGCTGGCCAGTACACCTGCCACAAAGGAGGCGAGACTCTGAGCCACTC
ACATCTGCTGCTCCACAAGAAGGAAAATGGAATTTGGTCCACTGAAATTTTAAAAAATTTCAA
AAACAAGACTTTCCTGAAGTGTGAAGCACCAAATTACTCCGGACGGTTCACGTGCTCATGGCT
GGTGCAAAGAAACATGGACTTGAAGTTCAACATCAAGAGCAGTAGCAGTTCCCCTGACTCTCG
GGCAGTGACATGTGGAATGGCGTCTCTGTCTGCAGAGAAGGTCACACTGGACCAAAGGGACTA
TGAGAAGTATTCAGTGTCCTGCCAGGAGGATGTCACCTGCCCAACTGCCGAGGAGACCCTGCC
CATTGAACTGGCGTTGGAAGCACGGCAGCAGAATAAATATGAGAACTACAGCACCAGCTTCTT
CATCAGGGACATCATCAAACCAGACCCGCCCAAGAACTTGCAGATGAAGCCTTTGAAGAACTC
ACAGGTGGAGGTCAGCTGGGAGTACCCTGACTCCTGGAGCACTCCCCATTCCTACTTCTCCCT
CAAGTTCTTTGTTCGAATCCAGCGCAAGAAAGAAAAGATGAAGGAGACAGAGGAGGGGTGTAA
CCAGAAAGGTGCGTTCCTCGTAGAGAAGACATCTACCGAAGTCCAATGCAAAGGCGGGAATGT
CTGCGTGCAAGCTCAGGATCGCTATTACAATTCCTCATGCAGCAAGTGGGCATGTGTTCCCTG
CAGGGTCCGATCCcgtgctaagcgaAGGGTCATTCCAGTCTCTGGACCTGCCAGGTGTCTTAG
CCAGTCCCGAAACCTGCTGAAGACCACAGATGACATGGTGAAGACGGCCAGAGAAAAACTGAA
ACATTATTCCTGCACTGCTGAAGACATCGATCATGAAGACATCACACGGGACCAAACCAGCAC
ATTGAAGACCTGTTTACCACTGGAACTACACAAGAACGAGAGTTGCCTGGCTACTAGAGAGAC
TTCTTCCACAACAAGAGGGAGCTGCCTGCCCCCACAGAAGACGTCTTTGATGATGACCCTGTG
CCTTGGTAGCATCTATGAGGACTTGAAGATGTACCAGACAGAGTTCCAGGCCATCAACGCAGC
ACTTCAGAATCACAACCATCAGCAGATCATTCTAGACAAGGGCATGCTGGTGGCCATCGATGA
GCTGATGCAGTCTCTGAATCATAATGGCGAGACTCTGCGCCAGAAACCTCCTGTGGGAGAAGC
AGACCCTTACAGAGTGAAAATGAAGCTCTGCATCCTGCTTCACGCCTTCAGCACCCGCGTCGT
GACCATCAACAGGGTGATGGGCTATCTGAGCTCCGCCTGACTCGAGTCACCAGGCG.
```

Additionally, a nucleotide sequence encoding mouse IL-12B followed by a nucleotide sequence encoding a furin cleavage site (RAKR) followed by a nucleotide sequence encoding mouse IL-23A was cloned into the modified E1b-19k region of TAV-Δ19k-ΔE3. The resulting virus is hereafter referred to as TAV-mIL-23-furin. The nucleotide sequence encoding mouse IL-12B followed by the nucleotide sequence encoding the furin cleavage site followed by the nucleotide sequence encoding mouse IL-23A inserted into the E1b-19k region is as follows, where the IL-12B and IL-23A coding regions are capitalized, the furin cleavage site coding region is lowercase, and the flanking E1b-19k sequence including the Sa1I and XhoI restriction sites is underlined:

(SEQ ID NO: 25)

ATCTGACCTCGTCGACATGTGTCCTCAGAAGCTAACCATCTCCTGGTTTGCCATCGTTTTGCT
GGTGTCTCCACTCATGGCCATGTGGGAGCTGGAGAAAGACGTTTATGTTGTAGAGGTGGACTG
GACTCCCGATGCCCCTGGAGAAACAGTGAACCTCACCTGTGACACGCCTGAAGAAGATGACAT
CACCTGGACCTCAGACCAGAGACATGGAGTCATAGGCTCTGGAAAGACCCTGACCATCACTGT
CAAAGAGTTTCTAGATGCTGGCCAGTACACCTGCCACAAAGGAGGCGAGACTCTGAGCCACTC
ACATCTGCTGCTCCACAAGAAGGAAAATGGAATTTGGTCCACTGAAATTTTAAAAAATTTCAA
AAACAAGACTTTCCTGAAGTGTGAAGCACCAAATTACTCCGGACGGTTCACGTGCTCATGGCT
GGTGCAAAGAAACATGGACTTGAAGTTCAACATCAAGAGCAGTAGCAGTTCCCCTGACTCTCG
GGCAGTGACATGTGGAATGGCGTCTCTGTCTGCAGAGAAGGTCACACTGGACCAAAGGGACTA
TGAGAAGTATTCAGTGTCCTGCCAGGAGGATGTCACCTGCCCAACTGCCGAGGAGACCCTGCC
CATTGAACTGGCGTTGGAAGCACGGCAGCAGAATAAATATGAGAACTACAGCACCAGCTTCTT
CATCAGGGACATCATCAAACCAGACCCGCCCAAGAACTTGCAGATGAAGCCTTTGAAGAACTC
ACAGGTGGAGGTCAGCTGGGAGTACCCTGACTCCTGGAGCACTCCCCATTCCTACTTCTCCCT
CAAGTTCTTTGTTCGAATCCAGCGCAAGAAAGAAAAGATGAAGGAGACAGAGGAGGGGTGTAA
CCAGAAAGGTGCGTTCCTCGTAGAGAAGACATCTACCGAAGTCCAATGCAAAGGCGGGAATGT
CTGCGTGCAAGCTCAGGATCGCTATTACAATTCCTCATGCAGCAAGTGGGCATGTGTTCCCTG
CAGGGTCCGATCCcgtgctaagcgaGTGCCTAGGAGTAGCAGTCCTGACTGGGCTCAGTGCCA
GCAGCTCTCTCGGAATCTCTGCATGCTAGCCTGGAACGCACATGCACCAGCGGGACATATGAA
TCTACTAAGAGAAGAAGAGGATGAAGAGACTAAAAATAATGTGCCCCGTATCCAGTGTGAAGA
TGGTTGTGACCCACAAGGACTCAAGGACAACAGCCAGTTCTGCTTGCAAAGGATCCGCCAAGG
TCTGGCTTTTTATAAGCACCTGCTTGACTCTGACATCTTCAAAGGGGAGCCTGCTCTACTCCC
TGATAGCCCCATGGAGCAACTTCACACCTCCCTACTAGGACTCAGCCAACTCCTCCAGCCAGA
GGATCACCCCCGGGAGACCCAACAGATGCCCAGCCTGAGTTCTAGTCAGCAGTGGCAGCGCCC
CCTTCTCCGTTCCAAGATCCTTCGAAGCCTCCAGGCCTTTTTGGCCATAGCTGCCCGGGTCTT
TGCCCACGGAGCAGCAACTCTGACTGAGCCCTTAGTGCCAACAGCTTAACTCGAGTCACCAGG
CG.

Additionally, a nucleotide sequence encoding mouse IL-27B followed by a nucleotide sequence encoding a furin cleavage site (RAKR) followed by a nucleotide sequence encoding mouse IL-27A was cloned into the modified E1b-19k region of TAV-Δ19k-ΔE3. The resulting virus is hereafter referred to as TAV-mIL-27-furin. The nucleotide sequence encoding mouse IL-27B followed by the nucleotide sequence encoding the furin cleavage site followed by the nucleotide sequence encoding mouse IL-27A inserted into the E1b-19k region is as follows, where the IL-27B and IL-27A coding regions are capitalized, the furin cleavage site coding region is lowercase, and the flanking E1b-19k sequence including the Sa1I and XhoI restriction sites is underlined:

(SEQ ID NO: 26)

```
ATCTGACCTCGTCGACATGTCCAAGCTGCTCTTCCTGTCACTTGCCCTCTGGGCCAGCCGCTC

CCCTGGTTACACTGAAACAGCTCTCGTGGCTCTAAGCCAGCCCAGAGTGCAATGCCATGCTTC

TCGGTATCCCGTGGCCGTGGACTGCTCCTGGACTCCTCTCCAGGCTCCCAACTCCACCAGATC

CACGTCCTTCATTGCCACTTACAGGCTCGGTGTGGCCACCCAGCAGCAGAGCCAGCCCTGCCT

ACAACGGAGCCCCCAGGCCTCCCGATGCACCATCCCCGACGTGCACCTGTTCTCCACGGTGCC

CTACATGCTAAATGTCACTGCAGTGCACCCAGGCGGCGCCAGCAGCAGCCTCCTAGCCTTTGT

GGCTGAGCGAATCATCAAGCCGGACCCTCCGGAAGGCGTGCGCCTGCGCACAGCGGGACAGCG

CCTGCAGGTGCTCTGGCATCCCCCTGCTTCCTGGCCCTTCCCGGACATCTTCTCTCTCAAGTA

CCGACTCCGCTACCGGCGCCGAGGAGCCTCTCACTTCCGCCAGGTGGGACCCATTGAAGCCAC

GACTTTCACCCTCAGGAACTCGAAACCCCATGCCAAGTATTGCATCCAGGTGTCAGCTCAGGA

CCTCACAGATTATGGGAAACCAAGTGACTGGAGCCTCCCTGGGCAAGTAGAAAGTGCACCCCA

TAAGCCCcgtgctaagcgaTTCCCAACAGACCCCCTGAGCCTTCAAGAGCTGCGCAGGGAATT

CACAGTCAGCCTGTACCTTGCCAGGAAGCTGCTCTCTGAGGTTCAGGGCTATGTCCACAGCTT

TGCTGAATCTCGATTGCCAGGAGTGAACCTGGACCTCCTGCCCCTGGGATACCATCTTCCCAA

TGTTTCCCTGACTTTCCAGGCATGGCATCACCTCTCTGACTCTGAGAGACTCTGCTTCCTCGC

TACCACACTTCGGCCCTTCCCTGCCATGCTGGGAGGGCTGGGGACCCAGGGGACCTGGACCAG

CTCAGAGAGGGAGCAGCTGTGGGCCATGAGGCTGGATCTCCGGGACCTGCACAGGCACCTCCG

CTTTCAGGTGCTGGCTGCAGGATTCAAATGTTCAAAGGAAGAGGAAGACAAGGAGGAAGAGGA

AGAGGAGGAAGAAGAAGAAAAGAAGCTGCCCCTAGGGGCTCTGGGTGGCCCCAATCAGGTGTC

ATCCCAAGTGTCCTGGCCCCAGCTGCTCTATACCTACCAGCTCCTTCACTCCCTGGAGCTTGT

CCTGTCTCGGGCTGTTCGGGACCTGCTGCTGCTGTCCCTGCCCAGGCGCCCAGGCTCAGCCTG

GGATTCCTAACTCGAGTCACCAGGCG.
```

Figure 9:
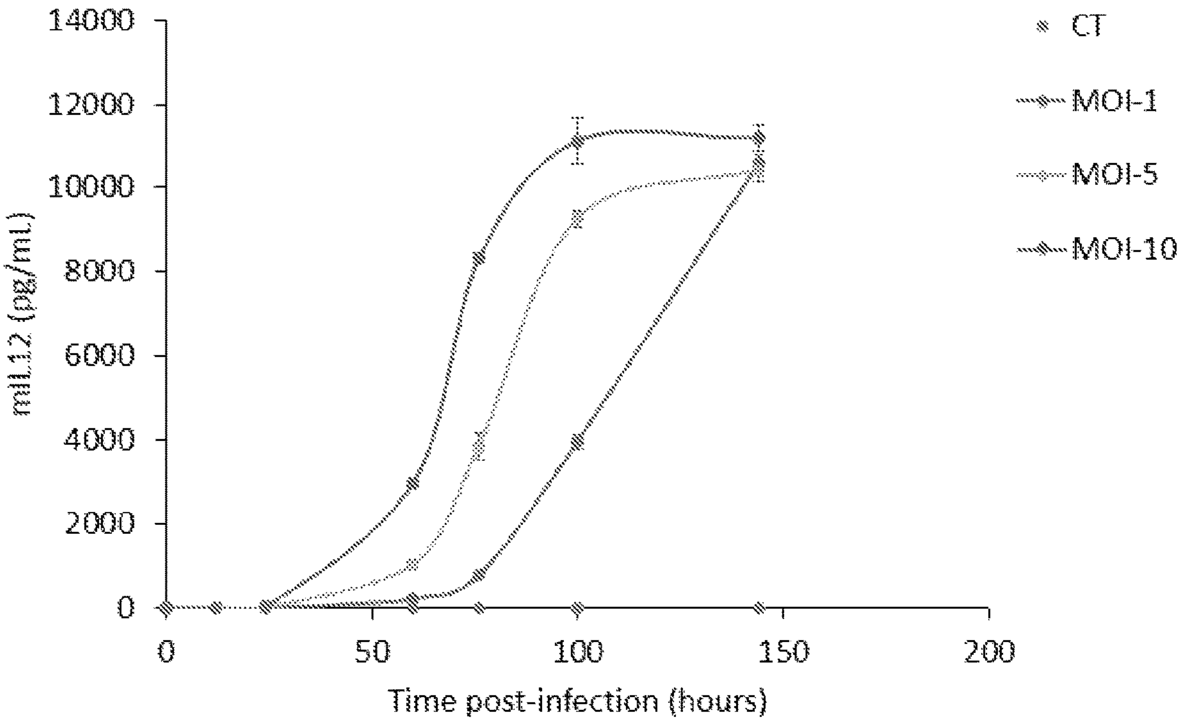
FIG. 9 is a line graph depicting expression of IL-12 from the virus TAV-mIL-12-furin. A549 cells were infected at the indicated MOI, and IL-12 concentration in conditioned media was measured at the indicated timepoints by ELISA. CT indicates control non-infected cells.

IL-12 expression from TAV-mIL-12-furin was tested. A549 cells were infected at an MOI of 1, 5, or 10 with TAV-mIL-12-furin or no virus. Conditioned media was collected at various times after infection and IL-12 concentration was measured by ELISA. As depicted in FIG. 9, IL-12 was expressed in a dose-dependent and time-dependent manner.

Figure 10:
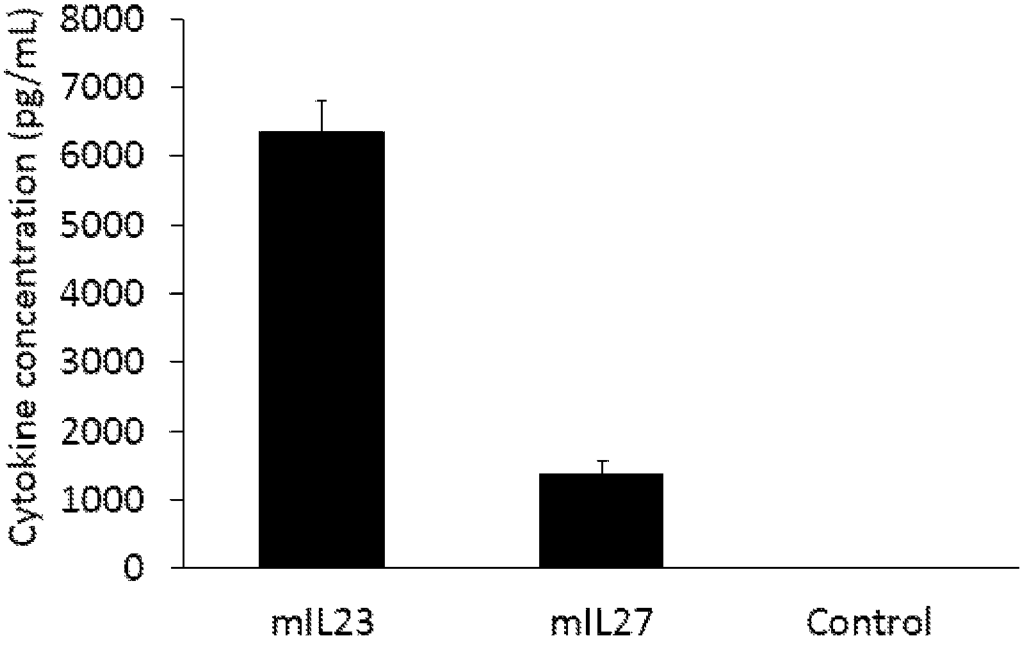
FIG. 10 is a bar graph depicting expression of IL-23 from the virus TAV-mIL-23-furin and IL-27 from the virus TAV-mIL-27-furin. A549 cells were infected at an MOI of 5 and the concentration of the corresponding cytokine for each virus in conditioned media was measured four days after infection by ELISA.

IL-23 and IL-27 expression from TAV-mIL-23-furin and TAV-mIL-27-furin were tested. A549 cells were infected at an MOI 5 with TAV-mIL-23-furin, TAV-mIL-27-furin, or no virus. Conditioned media was collected four days after infection and IL-23 and IL-27 concentrations were measured by ELISA. As depicted in FIG. 10, both viruses expressed the corresponding heterodimeric cytokine.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. An oncolytic adenovirus comprising
   a first nucleotide sequence encoding a first therapeutic transgene,
   a second nucleotide sequence encoding a second therapeutic transgene, and
   a third nucleotide sequence encoding a proteolytic cleavage site comprising a furin cleavage site disposed between the first nucleotide sequence and the second nucleotide sequence,
   wherein the first nucleotide sequence, the third nucleotide sequence, and the second nucleotide sequence comprise SEQ ID NOs: 8 or 9.

2. The oncolytic adenovirus of claim 1, wherein the first, second, and third nucleotide sequences are inserted into an E1b-19k insertion site located between the start site of E1b-19K and the stop site of E1b-19K or the start site of E1b-55K,
   the E1b-19K insertion site comprises a deletion of about 200 nucleotides, of 202 nucleotides, or of 203 nucleotides, adjacent the start site of E1b-19K, and/or
   the first nucleotide sequence, the third nucleotide sequence, and the second nucleotide sequence are inserted between CTGACCTC (SEQ ID NO: 2) and TCACCAGG (SEQ ID NO: 3) or the oncolytic adenovirus comprises, in a 5' to 3' orientation, CTGACCTC (SEQ ID NO: 2), the first nucleotide sequence, the third nucleotide sequence, the second nucleotide sequence, and TCACCAGG (SEQ ID NO: 3).

3. The oncolytic adenovirus of claim 1, wherein the oncolytic adenovirus comprises
   (a) an E1 a promoter having a deletion of a functional Pea3 binding site or a deletion of nucleotides in the oncolytic adenovirus genome that correspond to nucleotides 195-244 of SEQ ID NO: 1 when the oncolytic adenovirus genome is aligned to SEQ ID NO: 1, and/or the E1a promoter comprises the sequence GGTGTTTTGG (SEQ ID NO: 4), and/or
   (b) the Ela promoter having a deletion of a functional TATA box or deletion of the entire TATA box.

4. The oncolytic adenovirus of claim 1, wherein the oncolytic adenovirus comprises an E1a promoter having a deletion of a functional CAAT box or deletion of the entire CAAT box.

5. The oncolytic adenovirus of claim 1, wherein the oncolytic adenovirus further comprises an E3 deletion, wherein the E3 deletion is located between the stop site of pVIII and the start site of Fiber or between the stop site of E3-10.5K and the stop site of E3-14.7K, wherein the E3 deletion comprises deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or from about 3000 to about 3185 nucleotides; deletion of from about 500 to about 1551, from about 500 to about 1500, from about 500 to about 1000, from about 1000 to about 1551, from about 1000 to about 1500, or from about 1500 to about 1551 nucleotides adjacent the stop site of E3-10.5K;

deletion of about 1050 nucleotides adjacent the stop site of E3-10.5K; deletion of 1063 nucleotides adjacent the stop site of E3-10.5K; deletion of 1064 nucleotides adjacent the stop site of E3-10.5K; or a deletion of nucleotides in the oncolytic adenovirus genome that correspond to nucleotides 29773-30836 of SEQ ID NO: 1 when the oncolytic adenovirus genome is aligned to SEQ ID NO: 1, and/or wherein the E3 deletion is located between the stop site of E3-19K and the stop site of E3-14.7K, wherein the E3 deletion comprises deletion of from about 500 to about 1824, from about 500 to about 1500, from about 500 to about 1000, from about 1000 to about 1824, from about 1000 to about 1500, or from about 1500 to about 1824 nucleotides adjacent the stop site of E3-gp19K; deletion of about 1600 nucleotides adjacent the stop site of E3-19K; deletion of 1622 nucleotides adjacent the stop site of E3-gp19K; and/or deletion corresponding to nucleotides 29218-30839 of the Ad5 genome (SEQ ID NO: 1).

6. The oncolytic adenovirus of claim 1, wherein the oncolytic adenovirus further comprises an E4 deletion, wherein the E4 deletion is located between the start site of E4-ORF6/7 and right inverted terminal repeat (ITR) or between the start site of E4-ORF6/7 and the start site of E4-ORF1, wherein the E4 deletion comprises deletion of from about 500 to about 2500, from about 500 to about 2000, from about 500 to about 1500, from about 500 to about 1000, from about 1000 to about 2500, from about 1000 to about 2000, from about 1000 to about 1500, from about 1500 to about 2500, from about 1500 to about 2000, or from about 2000 to about 2500 nucleotides; deletion of from about 250 to about 1500, from about 250 to about 1250, from about 250 to about 1000, from about 250 to about 750, from about 250 to about 500, from 500 to about 1500, from about 500 to about 1250, from about 500 to about 1000, from about 500 to about 750, from 750 to about 1500, from about 750 to about 1250, from about 750 to about 1000, from about 1000 to about 1500, from about 1000 to about 1250, or from about 1250 to about 1500 nucleotides adjacent the start site of E4-ORF6/7; deletion of about 1450 nucleotides adjacent the start site of E4-ORF6/7; deletion of 1449 nucleotides adjacent the start site of E4-ORF6/7; and/or a deletion corresponding to nucleotides 34078-35526 of the Ad5 genome (SEQ ID NO: 1).

7. The oncolytic adenovirus of claim 1, wherein the first and second therapeutic transgenes are not operably linked to an exogenous promoter sequence.

8. The oncolytic adenovirus of claim 1, wherein the combined size of the first and second therapeutic transgenes comprises from about 500 to about 5000, from about 500 to about 4000, from about 500 to about 3000, from about 500 to about 2000, from about 500 to about 1000, from about 1000 to about 5000, from about 1000 to about 4000, from about 1000 to about 3000, from about 1000 to about 2000, from about 2000 to about 5000, from about 2000 to about 4000, from about 2000 to about 3000, from about 3000 to about 5000, from about 3000 to about 4000, or from about 4000 to 5000 nucleotides; from about 500 to about 7000, from about 500 to about 6000, from about 500 to about 5000, from about 500 to about 4000, from about 500 to about 3000, from about 500 to about 2000, from about 500 to about 1000, from about 1000 to about 7000, from about 1000 to about 6000, from about 1000 to about 5000, from about 1000 to about 4000, from about 1000 to about 3000, from about 1000 to about 2000, from about 2000 to about 7000, from about 2000 to about 6000, from about 2000 to about 5000, from about 2000 to about 4000, from about 2000 to about 3000, from about 3000 to about 7000, from about 3000 to about 6000, from about 3000 to about 5000, from about 3000 to about 4000, from about 4000 to about 7000, from about 4000 to about 6000, from about 4000 to about 5000 nucleotides, from about 5000 to about 7000, from about 5000 to about 6000, or from about 6000 to about 7000 nucleotides; at least from about 500 to about 5000, from about 500 to about 4000, from about 500 to about 3000, from about 500 to about 2000, from about 500 to about 1000, from about 1000 to about 5000, from about 1000 to about 4000, from about 1000 to about 3000, from about 1000 to about 2000, from about 2000 to about 5000, from about 2000 to about 4000, from about 2000 to about 3000, from about 3000 to about 5000, from about 3000 to about 4000, or from about 4000 to 5000 nucleotides; at least from about 500 to about 7000, from about 500 to about 6000, from about 500 to about 5000, from about 500 to about 4000, from about 500 to about 3000, from about 500 to about 2000, from about 500 to about 1000, from about 1000 to about 7000, from about 1000 to about 6000, from about 1000 to about 5000, from about 1000 to about 4000, from about 1000 to about 3000, from about 1000 to about 2000, from about 2000 to about 7000, from about 2000 to about 6000, from about 2000 to about 5000, from about 2000 to about 4000, from about 2000 to about 3000, from about 3000 to about 7000, from about 3000 to about 6000, from about 3000 to about 5000, from about 3000 to about 4000, from about 4000 to about 7000, from about 4000 to about 6000, from about 4000 to about 5000 nucleotides, from about 5000 to about 7000, from about 5000 to about 6000, or from about 6000 to about 7000 nucleotides; at least about 500, about 1000, about 2000, about 3000, about 4000, or about 5000 nucleotides; at least about 500, about 1000, about 2000, about 3000, about 4000, about 5000 nucleotides, about 6000, or about 7000 nucleotides; about 1600 nucleotides; about 1650 nucleotides; or about 3100 nucleotides.

9. The oncolytic adenovirus of claim 1, wherein the oncolytic adenovirus selectively replicates in a hyperproliferative cell.

10. The oncolytic adenovirus of claim 1, wherein the oncolytic adenovirus selectively expresses the first and/or the second therapeutic transgene in a hyperproliferative cell or a cancer cell.

11. A pharmaceutical composition comprising the oncolytic adenovirus of claim 1 and at least one pharmaceutically acceptable carrier or diluent.

12. A method of expressing two therapeutic transgenes in a target cell comprising exposing the cell to an effective amount of the oncolytic adenovirus of claim 1 to express the two therapeutic transgenes, wherein the two therapeutic transgenes, when expressed, produce a single polypeptide chain and the single polypeptide chain is cleaved posttranslationally into two polypeptide chains.

13. A method of inhibiting proliferation of a tumor cell, inhibiting tumor growth in a subject in need thereof, or of treating cancer in the subject in need thereof comprising exposing the cell to or administering to the subject an effective amount of the oncolytic adenovirus of claim 1 to inhibit proliferation of the tumor cell, to inhibit growth of the tumor, or to treat cancer in the subject, wherein the cancer is selected from (a) anal cancer, basal cell carcinoma, bladder cancer, bone cancer, brain cancer, breast cancer, carcinoma, cholangiocarcinoma, cervical cancer, colon cancer, colorectal cancer, endometrial cancer, gastroesophageal cancer, gastrointestinal (GI) cancer, gastrointestinal stromal tumor, hepatocellular carcinoma, gynecologic cancer, head and neck cancer, hematologic cancer, kidney cancer, leukemia, liver cancer, lung cancer, lymphoma, melanoma, merkel cell carcinoma, mesothelioma, neuroendocrine cancer, non-small cell lung cancer, ovarian cancer, pancreatic cancer, pediatric cancer, prostate cancer, renal cell carcinoma, sarcoma, skin cancer, small cell lung cancer, squamous cell carcinoma of the skin, stomach cancer, testicular cancer and thyroid cancer, or (b) melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, hepatocellular carcinoma, cholangiocarcinoma, brain cancer, endometrial cancer, neuroendocrine cancer, merkel cell carcinoma, gastrointestinal stromal tumors, a sarcoma, and pancreatic cancer, wherein the oncolytic recombinant adenovirus is administered in combination with one or more therapies selected from surgery, radiation, chemotherapy, immunotherapy, hormone therapy, and virotherapy, wherein the effective amount of the oncolytic adenovirus is $10^2$-$10^{15}$ aque forming units (pfus), and/or wherein the subject is a human or a pediatric human.

* * * * *